US011840572B2

(12) United States Patent
Apgar et al.

(10) Patent No.: US 11,840,572 B2
(45) Date of Patent: Dec. 12, 2023

(54) THERAPEUTIC ANTIBODIES AND THEIR USES

(71) Applicant: PFIZER INC., New York, NY (US)

(72) Inventors: James Reasoner Apgar, Newton, MA (US); Andrea Therese Hooper, Port Chester, NY (US); Malgorzata Agnieszka Nocula-Lugowska, Brighton, MA (US); Lei Wu, New York, NY (US)

(73) Assignee: Pfizer Inc., New York, NY (US)

( * ) Notice: Subject to any disclaimer, the term of this patent is extended or adjusted under 35 U.S.C. 154(b) by 124 days.

(21) Appl. No.: 17/378,377

(22) Filed: Jul. 16, 2021

(65) Prior Publication Data

US 2022/0017622 A1    Jan. 20, 2022

Related U.S. Application Data

(60) Provisional application No. 63/053,243, filed on Jul. 17, 2020.

(51) Int. Cl.
*C07K 16/28* (2006.01)
*A61P 35/00* (2006.01)
*A61K 39/00* (2006.01)

(52) U.S. Cl.
CPC .......... *C07K 16/2827* (2013.01); *A61P 35/00* (2018.01); *C07K 16/2809* (2013.01); *A61K 2039/505* (2013.01); *C07K 2317/31* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 9,969,809 B2 | 5/2018 | Kuo et al. |
| 11,434,292 B2 | 9/2022 | Apgar et al. |

FOREIGN PATENT DOCUMENTS

| EP | 3492591 A1 | 6/2019 |
| WO | 2014/159835 A1 | 10/2014 |
| WO | 2016040724 A1 | 3/2016 |
| WO | 2018/195302 A1 | 10/2018 |
| WO | 2019/040780 A1 | 2/2019 |
| WO | 2019/224716 A2 | 11/2019 |

OTHER PUBLICATIONS

Iizuka et al. 2019 (A T-cell-engaging B7-H4/CD3-bispecific Fab-scFv Antibody Targets Human Breast Cancer, Clin Cancer Res (2019) 25 (9): 2925-2934). (Year: 2019).*
Brinkmann, U., et al., "The making of bispecific antibodies," MABS, 2017, 182-212, vol. 9, No. 2.
International Search Report for International Appln. No. PCT/IB2021/056346 completed Nov. 17, 2021.
Wang, F., et al., "Design and characterization of mouse IgG1 and IgG2a bispecific antibodies for use in syngeneic models," MABS, 2019, 1-12, vol. 12, No. 1.
Written Opinion of the International Searching Authority for International Appln. No. PCT/IB2021/056346 completed on Nov. 17, 2021.

* cited by examiner

*Primary Examiner* — Misook Yu
*Assistant Examiner* — Sarah A Alsomairy
(74) *Attorney, Agent, or Firm* — Austin W. Zhang

(57) ABSTRACT

The present invention relates to antibodies that specifically bind to B7-H4 (B7 Homology 4, encoded by gene VTCN1) and bispecific antibodies that specifically bind to both B7-H4 and CD3 (Cluster of Differentiation 3), and polynucleotides, pharmaceutical compositions and methods and uses thereof.

21 Claims, 4 Drawing Sheets

Specification includes a Sequence Listing.

FIG. 1

Alignment of anti-B7-H4, anti-CD3, and wildtype human IgG2, IgG1 and IgG4 heavy chain constant regions with EU numbering scheme

```
          118        128        138        148        158        168
B7-H4  ASTKGPSVFP LAPCSRSTSE STAALGCLVK DYFPEPVTVS WNSGALTSGV HTFPAVLQSS
CD3    ASTKGPSVFP LAPCSRSTSE STAALGCLVK DYFPEPVTVS WNSGALTSGV HTFPAVLQSS
IgG2   ASTKGPSVFP LAPCSRSTSE STAALGCLVK DYFPEPVTVS WNSGALTSGV HTFPAVLQSS
IgG1   ASTKGPSVFP LAPSSKSTSG GTAALGCLVK DYFPEPVTVS WNSGALTSGV HTFPAVLQSS
IgG4   ASTKGPSVFP LAPCSRSTSE STAALGCLVK DYFPEPVTVS WNSGALTSGV HTFPAVLQSS 178        188        198        208        218   223 225 228  231    237
B7-H4  GLYSLSSVVT VPSSNFGTQT YTCNVDHKPS NTKVDKTVER KC--- EV  ECP ECP  APPVA- GPSVF
CD3    GLYSLSSVVT VPSSNFGTQT YTCNVDHKPS NTKVDKTVER KC--- RV  RCP RCP  APPVA- GPSVF
IgG2   GLYSLSSVVT VPSSNFGTQT YTCNVDHKPS NTKVDKTVER KC--- CV  ECP PCP  APPVA- GPSVF
IgG1   GLYSLSSVVT VPSSSLGTQT YICNVNHKPS NTKVDKKVEP KSCDK TH  TCP PCP  APELLG GPSVF
IgG4   GLYSLSSVVT VPSSSLGTKT YTCNVDHKPS NTKVDKRVES KY--- GP  PCP SCP  APEFLG GPSVF 242        252        265        272        282        292
B7-H4  LFPPKPKDTL MISRTPEVTC VVVAVSHEDP EVQFNWYVDG VEVHNAKTKP REEQFNSTFR
CD3    LFPPKPKDTL MISRTPEVTC VVVAVSHEDP EVQFNWYVDG VEVHNAKTKP REEQFNSTFR
IgG2   LFPPKPKDTL MISRTPEVTC VVVDVSHEDP EVQFNWYVDG VEVHNAKTKP REEQFNSTFR
IgG1   LFPPKPKDTL MISRTPEVTC VVVDVSHEDP EVKFNWYVDG VEVHNAKTKP REEQYNSTYR
IgG4   LFPPKPKDTL MISRTPEVTC VVVDVSQEDP EVQFNWYVDG VEVHNAKTKP REEQFNSTYR 302        312        322    330/331     342        352
B7-H4  VVSVLTVVHQ DWLNGKEYKC KVSNKGLPSS IEKTISKTKG QPREPQVYTL PPSREEMTKN
CD3    VVSVLTVVHQ DWLNGKEYKC KVSNKGLPSS IEKTISKTKG QPREPQVYTL PPSREEMTKN
IgG2   VVSVLTVVHQ DWLNGKEYKC KVSNKGLPAP IEKTISKTKG QPREPQVYTL PPSREEMTKN
IgG1   VVSVLTVLHQ DWLNGKEYKC KVSNKALPAP IEKTISKAKG QPREPQVYTL PPSRDELTKN
IgG4   VVSVLTVLHQ DWLNGKEYKC KVSNKGLPSS IEKTISKAKG QPREPQVYTL PPSQEEMTKN 362        372        382        392        402  409  412
B7-H4  QVSLTCEVKG FYPSDIAVEW ESNGQPENNY KTTPPMLDSD GSFFLYSKLT VDKSRWQQGN
CD3    QVSLTCLVKG FYPSDIAVEW ESNGQPENNY KTTPPMLDSD GSFFLYSRLT VDKSRWQQGN
IgG2   QVSLTCLVKG FYPSDIAVEW ESNGQPENNY KTTPPMLDSD GSFFLYSKLT VDKSRWQQGN
IgG1   QVSLTCLVKG FYPSDIAVEW ESNGQPENNY KTTPPVLDSD GSFFLYSKLT VDKSRWQQGN
IgG4   QVSLTCLVKG FYPSDIAVEW ESNGQPENNY KTTPPVLDSD GSFFLYSRLT VDKSRWQEGN 4         22         432        442
B7-H4  VFSCSVMHEA LHNHYTQKSL SLSPGK     SEQ ID NO: 177
CD3    VFSCSVMHEA LHNHYTQKSL SLSPGK     SEQ ID NO: 178
IgG2   VFSCSVMHEA LHNHYTQKSL SLSPGK     SEQ ID NO: 208
IgG1   VFSCSVMHEA LHNHYTQKSL SLSPGK     SEQ ID NO: 209
IgG4   VFSCSVMHEA LHNHYTQKSL SLSLGK     SEQ ID NO: 210
```

Double underline: heterodimer stabilization mutations

Single underline: Fc effector mutations

Crystal structure of B7-H4 antibody 0052 scFv complexed with B7-H4 ECD

Crystal structure of B7-H4 antibody 0058 Fab complexed with B7-H4 ECD

Crystal structure of B7-H4 antibody 1114 Fab complexed with B7-H4 ECD

US 11,840,572 B2

THERAPEUTIC ANTIBODIES AND THEIR USES

CROSS REFERENCE TO RELATED APPLICATIONS

This application claims the benefit of U.S. Provisional Application No. 63/053,243, filed Jul. 17, 2020, the disclosure of which is hereby incorporated by reference in its entirety.

REFERENCE TO SEQUENCE LISTING

This application is being filed electronically via EFS-Web and includes an electronically submitted sequence listing in .txt form. The .txt file contains a sequence listing entitled "PC72604A_SEQListing_ST25.tex" created on Jun. 24, 2021 and having a size of 173 KB. The sequence listing contained in this .txt file is part of the specification and is incorporated herein by reference it its entirety.

FIELD

The present invention relates to antibodies that specifically bind to B7-H4 (B7 Homology 4), compositions comprising the B7-H4 antibodies and the methods and uses thereof. The invention also relates to bispecific antibodies that specifically bind to B7-H4 and CD3 (Cluster of Differentiation 3), compositions comprising the bispecific B7-H4 antibodies, and methods of using the bispecific B7-H4 antibodies for treating conditions associated with cells expressing B7-H4 (e.g., cancer or autoimmune disease). Methods for producing and purifying such bispecific antibodies, and their use in diagnostics and therapeutics are also provided.

BACKGROUND

B7-H4 (B7 Homology 4, encoded by gene VTCN1), also known as B7x, B7S1 or VTCN1, is a type I transmembrane protein and a member of the B7 family proteins. B7-H4 was first identified more than a decade and a half ago (Sica G L, et al. *Immunity.* 2003; 18:849-861). Since then, it has been found that B7-H4 is overexpressed in breast and ovarian cancers (Salceda S, et al., *Exp Cell Res.* 2005; 306:128-141) and many other cancer cells. It has also been found that that B7-H4 protein expression within tumors are related to shorter life expectancy and disease severity (Podojil, J. R., Miller, S. D., Immunological Reviews 2017; 276:40-51) Although B7-H4 is a B7 family molecule, it does not bind to any of the known B7-family receptors, i.e. CTLA-4, ICOS, PD-1 or CD28. Efforts to identify a B7-H4 specific receptor have revealed that such a receptor is expressed on activated T cells and the binding of B7-H4 fusion protein to its putative receptor on T cells was found to significantly inhibit T cell proliferation and cytokine (IL-2, IFN-gamma, and IL17) production. (Podojil, J. R., Miller, S. D., Immunological Reviews 2017; 276:40-51).

There remains a need for molecules and/or compositions which can specifically target and specifically bind to breast, ovarian, and other types of cancer cells. There is a need for improved methods of treating individuals who are suspected of suffering from cancer.

SUMMARY

Antibodies that specifically bind to B7-H4, and bispecific antibodies that specifically bind to both B7-H4 and CD3 (hereinafter "B7-H4×CD3 bispecific antibodies") are provided. It is demonstrated that some of the antibodies disclosed herein, including the bispecific antibodies, have efficacy in vivo to prevent and/or to treat cancer.

In one aspect, the present invention provides an isolated antibody that specifically binds to B7-H4, comprising (a) a heavy chain variable region (VH) complementarity determining region (CDR) one (CDR1), a VH CDR2 and a VH CDR3 of a VH having an amino acid sequence selected from the group consisting of SEQ ID NO: 23, SEQ ID NO:155, SEQ ID NO: 156, SEQ ID NO: 157, SEQ ID NO: 159, SEQ ID NO:161, SEQ ID NO:163, SEQ ID NO:165, SEQ ID NO:169, SEQ ID NO: 171, SEQ ID NO: 172, SEQ ID NO: 173, SEQ ID NO: 174, SEQ ID NO: 175 and SEQ ID NO: 176; and (B) a light chain variable region (VL) complementarity determining region one (CDR1), a VL CDR2 and a VL CDR3 of a VL having an amino acid sequence selected from the group consisting of SEQ ID NO:27, SEQ ID NO: 139, SEQ ID NO:141, SEQ ID NO:167, SEQ ID NO:168, SEQ ID NO:169 and SEQ ID NO:170.

In some embodiments, the antibody is such that (a) the VH having the amino acid sequence of SEQ ID NO:161; and the VL having the amino acid sequence of SEQ ID NO:167; (b) the VH having the amino acid sequence of SEQ ID NO:172; and the VL having the amino acid sequence of SEQ ID NO:139; (c) the VH having the amino acid sequence of SEQ ID NO:155; and the VL having the amino acid sequence of SEQ ID NO:139; (d) the VH having the amino acid sequence of SEQ ID NO:156; and the VL having the amino acid sequence of SEQ ID NO:139; (e) the VH having the amino acid sequence of SEQ ID NO:157; and the VL having the amino acid sequence of SEQ ID NO:141; (f) the VH having the amino acid sequence of SEQ ID NO:155; and the VL having the amino acid sequence of SEQ ID NO:141; (g) the VH having the amino acid sequence of SEQ ID NO:156; and the VL having the amino acid sequence of SEQ ID NO:141; (h) the VH having the amino acid sequence of SEQ ID NO:159; and the VL having the amino acid sequence of SEQ ID NO:27; (i) the VH having the amino acid sequence of SEQ ID NO:161; and the VL having the amino acid sequence of SEQ ID NO:27; (j) the VH having the amino acid sequence of SEQ ID NO:163; and the VL having the amino acid sequence of SEQ ID NO:27; (k) the VH having the amino acid sequence of SEQ ID NO:165; and the VL having the amino acid sequence of SEQ ID NO:27; (l) the VH having the amino acid sequence of SEQ ID NO:23; and the VL having the amino acid sequence of SEQ ID NO:167; (m) the VH having the amino acid sequence of SEQ ID NO:171; and the VL having the amino acid sequence of SEQ ID NO:141; (n) the VH having the amino acid sequence of SEQ ID NO:172; and the VL having the amino acid sequence of SEQ ID NO:141; (o) the VH having the amino acid sequence of SEQ ID NO:171; and the VL having the amino acid sequence of SEQ ID NO:139; (p) the VH having the amino acid sequence of SEQ ID NO:173; and the VL having the amino acid sequence of SEQ ID NO:139; (q) the VH having the amino acid sequence of SEQ ID NO:174; and the VL having the amino acid sequence of SEQ ID NO:139; (r) the VH having the amino acid sequence of SEQ ID NO:175; and the VL having the amino acid sequence of SEQ ID NO:139; (s) the VH having the amino acid sequence of SEQ ID NO:161; and the VL having the amino acid sequence of SEQ ID NO:168; (t) the VH having the amino acid sequence of SEQ ID NO:161; and the VL having the amino acid sequence of SEQ ID NO:169; (u) the VH having the amino acid sequence of SEQ ID NO:161; and the VL having the amino acid sequence of SEQ ID NO:170;

or (v) the VH having the amino acid sequence of SEQ ID NO:172; and the VL having the amino acid sequence of SEQ ID NO:139.

In some embodiments, the antibody comprises (a) a VH CDR1 having the amino acid sequence of SEQ ID NO: 20; a VH CDR2 having the amino acid sequence of SEQ ID NO:21, a VH CDR3 having the amino acid sequence of SEQ ID NO:160, a VL CDR1 having the amino acid sequence of SEQ ID NO: 166, a VL CDR2 having the amino acid sequence of SEQ ID NO:25 and a VL CDR3 having the amino acid sequence of SEQ ID NO:153; (b) a VH CDR1 having the amino acid sequence of SEQ ID NO: 205; a VH CDR2 having the amino acid sequence of SEQ ID NO:21, a VH CDR3 having the amino acid sequence of SEQ ID NO:160, a VL CDR1 having the amino acid sequence of SEQ ID NO: 166, a VL CDR2 having the amino acid sequence of SEQ ID NO:25 and a VL CDR3 having the amino acid sequence of SEQ ID NO:153; (c) a VH CDR1 having the amino acid sequence of SEQ ID NO: 206; a VH CDR2 having the amino acid sequence of SEQ ID NO:207, a VH CDR3 having the amino acid sequence of SEQ ID NO:160, a VL CDR1 having the amino acid sequence of SEQ ID NO: 166, a VL CDR2 having the amino acid sequence of SEQ ID NO:25 and a VL CDR3 having the amino acid sequence of SEQ ID NO:153; (d) a VH CDR1 having the amino acid sequence of SEQ ID NO: 5; a VH CDR2 having the amino acid sequence of SEQ ID NO:6, a VH CDR3 having the amino acid sequence of SEQ ID NO:7, a VL CDR1 having the amino acid sequence of SEQ ID NO: 9, a VL CDR2 having the amino acid sequence of SEQ ID NO:10 and a VL CDR3 having the amino acid sequence of SEQ ID NO:138; (e) a VH CDR1 having the amino acid sequence of SEQ ID NO: 199; a VH CDR2 having the amino acid sequence of SEQ ID NO:6, a VH CDR3 having the amino acid sequence of SEQ ID NO:7, a VL CDR1 having the amino acid sequence of SEQ ID NO: 9, a VL CDR2 having the amino acid sequence of SEQ ID NO:10 and a VL CDR3 having the amino acid sequence of SEQ ID NO:138; (f) a VH CDR1 having the amino acid sequence of SEQ ID NO: 200; a VH CDR2 having the amino acid sequence of SEQ ID NO:201, a VH CDR3 having the amino acid sequence of SEQ ID NO:7, a VL CDR1 having the amino acid sequence of SEQ ID NO: 9, a VL CDR2 having the amino acid sequence of SEQ ID NO:10 and a VL CDR3 having the amino acid sequence of SEQ ID NO:138; (g) a VH CDR1 having the amino acid sequence of SEQ ID NO: 20; a VH CDR2 having the amino acid sequence of SEQ ID NO:21, a VH CDR3 having the amino acid sequence of SEQ ID NO:160, a VL CDR1 having the amino acid sequence of SEQ ID NO: 152, a VL CDR2 having the amino acid sequence of SEQ ID NO:41 and a VL CDR3 having the amino acid sequence of SEQ ID NO:153; (h) a VH CDR1 having the amino acid sequence of SEQ ID NO: 5; a VH CDR2 having the amino acid sequence of SEQ ID NO:6, a VH CDR3 having the amino acid sequence of SEQ ID NO:7, a VL CDR1 having the amino acid sequence of SEQ ID NO: 9, a VL CDR2 having the amino acid sequence of SEQ ID NO:10 and a VL CDR3 having the amino acid sequence of SEQ ID NO:138; or (i) a VH CDR1 having the amino acid sequence of SEQ ID NO: 5; a VH CDR2 having the amino acid sequence of SEQ ID NO:130, a VH CDR3 having the amino acid sequence of SEQ ID NO:7, a VL CDR1 having the amino acid sequence of SEQ ID NO: 9, a VL CDR2 having the amino acid sequence of SEQ ID NO:10 and a VL CDR3 having the amino acid sequence of SEQ ID NO:138.

In one aspect, the invention provides an isolated antibody that specifically binds to B7-H4, comprising a VH CDR1 having the amino acid sequence of SEQ ID NO: 20; a VH CDR2 having the amino acid sequence of SEQ ID NO:21, a VH CDR3 having the amino acid sequence of SEQ ID NO:160, a VL CDR1 having the amino acid sequence of SEQ ID NO: 166, a VL CDR2 having the amino acid sequence of SEQ ID NO:25 and a VL CDR3 having the amino acid sequence of SEQ ID NO:153;

In some embodiments, the antibody comprises (a) a VH having the amino acid sequence of SEQ ID NO:161; and a VL having the amino acid sequence of SEQ ID NO:167; (b) a VH having the amino acid sequence of SEQ ID NO:172; and a VL having the amino acid sequence of SEQ ID NO:139; (c) a VH having the amino acid sequence of SEQ ID NO:155; and a VL having the amino acid sequence of SEQ ID NO:139; (d) a VH having the amino acid sequence of SEQ ID NO:156; and a VL having the amino acid sequence of SEQ ID NO:139; (e) a VH having the amino acid sequence of SEQ ID NO:157; and a VL having the amino acid sequence of SEQ ID NO:141; (f) a VH having the amino acid sequence of SEQ ID NO:155; a VL having the amino acid sequence of SEQ ID NO:141; (g) a VH having the amino acid sequence of SEQ ID NO:156; and a VL having the amino acid sequence of SEQ ID NO:141; (h) a VH having the amino acid sequence of SEQ ID NO:159; and a VL having the amino acid sequence of SEQ ID NO:27; (i) a VH having the amino acid sequence of SEQ ID NO:161; and a VL having the amino acid sequence of SEQ ID NO:27; (j) a VH having the amino acid sequence of SEQ ID NO:163; and a VL having the amino acid sequence of SEQ ID NO:27; (k) a VH having the amino acid sequence of SEQ ID NO:165; and a VL having the amino acid sequence of SEQ ID NO:27; (l) a VH having the amino acid sequence of SEQ ID NO:23; and a VL having the amino acid sequence of SEQ ID NO:167; (m) a VH having the amino acid sequence of SEQ ID NO:171; and a VL having the amino acid sequence of SEQ ID NO:141; (n) a VH having the amino acid sequence of SEQ ID NO:172; and a VL having the amino acid sequence of SEQ ID NO:141; (o) a VH having the amino acid sequence of SEQ ID NO:171; and a VL having the amino acid sequence of SEQ ID NO:139; (p) a VH having the amino acid sequence of SEQ ID NO:173; and a VL having the amino acid sequence of SEQ ID NO:139; (q) a VH having the amino acid sequence of SEQ ID NO:174; and a VL having the amino acid sequence of SEQ ID NO:139; (r) a VH having the amino acid sequence of SEQ ID NO:175; and a VL having the amino acid sequence of SEQ ID NO:139; (s) a VH having the amino acid sequence of SEQ ID NO:161; and a VL having the amino acid sequence of SEQ ID NO:168; (t) a VH having the amino acid sequence of SEQ ID NO:161; and a VL having the amino acid sequence of SEQ ID NO:169; (u) a VH having the amino acid sequence of SEQ ID NO:161; and a VL having the amino acid sequence of SEQ ID NO:170; or (v) a VH having the amino acid sequence of SEQ ID NO:172; and a VL having the amino acid sequence of SEQ ID NO:139.

In one aspect, the invention provides an isolated antibody that specifically binds to B7-H4, comprising a VH having the amino acid sequence of SEQ ID NO:161; and a VL having the amino acid sequence of SEQ ID NO:167.

In one aspect, the invention provides an isolated antibody that specifically binds to B7-H4, comprising a VH having the amino acid sequence of SEQ ID NO:172; and a VL having the amino acid sequence of SEQ ID NO:139 In some embodiments, the antibody further comprises a constant region. In some embodiments, constant region is an isotype of IgG1 or IgG2. In some embodiments, the antibody is a human IgG2 comprising one or more substitutions selected from the group consisting of A330S, P331S, D265A, C223E, P228E, L368E, C223R, E225R, P228R, and K409R, wherein the numbering is according to human IgG2 wild-type and the EU numbering scheme, and as shown in FIG. 1. In some embodiments, the antibody comprises the substitutions C223E, P228E and L368E.

In one aspect, the invention provides an isolated antibody that specifically binds to B7-H4, comprising a heavy chain having the amino acid sequence of SEQ ID NO: 190, and a light chain having the amino acid sequence of SEQ ID NO: 191.

In one aspect, the invention provides an isolated antibody that specifically binds to B7-H4, comprising a heavy chain having the amino acid sequence of SEQ ID NO:186, and a light chain having the amino acid sequence of SEQ ID NO: 187.

In some embodiments, the present invention provides an isolated antibody that specifically binds to B7-H4, comprising a heavy chain comprising the amino acid sequence of the full-length polypeptide encoded by the open reading frame (ORF) of the polynucleotide deposited under ATCC Accession No. PTA-126779, and a light chain comprising the amino acid sequence of the full-length polypeptide encoded by the open reading frame (ORF) of the polynucleotide deposited under with ATCC Accession No. PTA-126781.

In some embodiments, each of the VH CDR1, the VH CDR2, the VH CDR3, the VL CDR1, the VL CDR2 and the VL CDR3 is defined in accordance with the Kabat definition, the Chothia definition, the AbM definition, or the contact definition of CDR.

In one aspect, the present invention provides an isolated first antibody that specifically binds to B7-H4, that competes for binding with B7-H4 with a second antibody comprising (a) VH having the amino acid sequence of SEQ ID NO:8, and a VL having the amino acid sequence of SEQ ID NO:13; (b) a VH having the amino acid sequence of SEQ ID NO:8, and a VL having the amino acid sequence of SEQ ID NO:13; (c) a VH having the amino acid sequence of SEQ ID NO:39, and a VL having the amino acid sequence of SEQ ID NO:43; (d) a VH having the amino acid sequence of SEQ ID NO:46, and a VL having the amino acid sequence of SEQ ID NO:49; (e) a VH having the amino acid sequence of SEQ ID NO:52, and a VL having the amino acid sequence of SEQ ID NO:54; (f) a VH having the amino acid sequence of SEQ ID NO:57, and a VL having the amino acid sequence of SEQ ID NO:60; (g) a VH having the amino acid sequence of SEQ ID NO:16, and a VL having the amino acid sequence of SEQ ID NO:19; (h) a VH having the amino acid sequence of SEQ ID NO:64, and a VL having the amino acid sequence of SEQ ID NO:67; (i) a VH having the amino acid sequence of SEQ ID NO:69, and a VL having the amino acid sequence of SEQ ID NO:70; (j) a VH having the amino acid sequence of SEQ ID NO:74, and a VL having the amino acid sequence of SEQ ID NO:77; (k) a VH having the amino acid sequence of SEQ ID NO:80, and a VL having the amino acid sequence of SEQ ID NO:84; (l) a VH having the amino acid sequence of SEQ ID NO:87, and a VL having the amino acid sequence of SEQ ID NO:90; (m) a VH having the amino acid sequence of SEQ ID NO:23, and a VL having the amino acid sequence of SEQ ID NO:27; (n) a VH having the amino acid sequence of SEQ ID NO:94, and a VL having the amino acid sequence of SEQ ID NO:96; (o) a VH having the amino acid sequence of SEQ ID NO:100, and a VL having the amino acid sequence of SEQ ID NO:77; or (p) a VH having the amino acid sequence of SEQ ID NO:104, and a VL having the amino acid sequence of SEQ ID NO:67; wherein the first antibody has a $K_D$ to human B7-H4 of between about 1 micromolar and 0.1 nanomolar. In some embodiments, the first antibody and the second antibody each comprise a full length IgG1 constant region. in some embodiments, the first antibody and second antibody are both F(ab')2 fragment antibodies.

In another aspect, the invention provides an isolated antibody that specifically binds to B7-H4, wherein the antibody binds to an epitope on human B7-H4 comprising at least two at least three, at least four, at least five, at least six, at least seven, at least eight, at least nine, at least ten, at least eleven or at least twelve amino acid residues selected from the group consisting of L44, K45, E46, G47, V48, L49, G50, L51, E64, D66, M68, T99 and K101 of the B7-H4 extracellular domain having the amino acid sequence of SEQ ID NO: 1. In some embodiments, the epitope comprises at least one, at least two, at least three, at least four, at least five, at least six or at least seven amino acid residues selected from the group consisting of L44, K45, E46, G47, V48, L49, G50 and L51, and at least one, at least two, at least three or at least four amino acid residues selected from the group consisting of E64, D66, M68, T99 and K101. In some embodiments, the epitope comprises or consists of the amino acid residues of L44, K45, E46, G47, V48, L49, G50, L51, E64, D66, M68, T99 and K101.

In another aspect, the invention provides an isolated antibody that specifically binds to B7-H4, wherein the antibody binds to an epitope on human B7-H4 comprising at least two, at least three, at least four, at least five, at least six, at least seven, at least eight, at least nine, at least ten, at least eleven, at least twelve, or at least thirteen amino acid residues selected from the group consisting of V129, Y131, N132, S134, S135, E136, L138, V189, I191, V212, E214, S215, E216 and I217 of the B7-H4 extracellular domain having the amino acid sequence of SEQ ID NO: 1. In some embodiments, the epitope comprises at least one, at least two, at least three, at least four, at least five or at least six amino acid residues selected from the group consisting of V129, Y131, N132, S134, S135, E136 and L138, and at least one at least two, at least three, at least four, at least five, at least six or at least seven amino acid residues from the group consisting of, V189, I191, V212, E214, S215, E216 and I217. In some embodiments, the epitope comprises or consists of the amino acid residues V129, Y131, N132, S134, S135, E136, L138, V189, I191, V212, E214, S215, E216 and I217.

In another aspect, the present invention provides a pharmaceutical composition comprising a therapeutically effective amount of the B7-H4 antibody of the present invention or an antigen binding fragment thereof and a pharmaceutically acceptable carrier.

In another aspect, the present invention provides an an isolated polynucleotide encoding the B7-H4 antibody of the present invention.

In another aspect, the present invention provides an isolated polynucleotide encoding (i) a heavy chain variable region of the B7-H4 antibodies of the present invention or (ii) a light chain variable region of any of the B7-H4 antibodies of the present invention.

In another aspect, the present invention provides an isolated polynucleotide encoding (i) a heavy chain of the B7-H4 antibodies of the present invention or (ii) a light chain of any of the B7-H4 antibodies of the present invention.

In another aspect, the present invention provides a vector comprising any of the polynucleotides of the present invention.

In another aspect, the present invention provides an isolated host cell that recombinantly produces the antibody of the present invention.

In another aspect, the present invention provides a method of producing an B7-H4 antibody of the present invention, comprising culturing the host cell of the present invention under conditions that result in production of the antibody, and isolating the antibody from the host cell or culture.

In another aspect, the present invention provides a method of treating a condition associated with cells expressing B7-H4 in a subject comprising administering to a subject in need thereof an effective amount of the pharmaceutical composition of the present invention. In some embodiments, the condition is cancer. In some embodiments, the cancer is breast cancer, ovarian cancer, bladder cancer, cancer of the uterus or cancer of the bile duct.

In another aspect, the present invention provides a method of inhibiting tumor growth or progression in a subject who has malignant cells expressing B7-H4, comprising administering to the subject in need thereof an effective amount of the pharmaceutical composition of the present invention to the subject.

In another aspect, the present invention provides a method of inhibiting metastasis of malignant cells expressing B7-H4 in a subject, comprising administering to the subject in need thereof an effective amount of the pharmaceutical composition of the present invention to the subject.

In another aspect, the present invention provides a method of inducing tumor regression in a subject who has malignant cells expressing B7-H4, comprising administering to the subject in need thereof an effective amount of the pharmaceutical composition of the present invention to the subject.

In another aspect, the present invention provides a bispecific antibody that specifically binds to both B7-H4 and CD3, comprising a first heavy chain and a first light chain, and a second heavy chain and a second light chain, wherein the first heavy chain and the first light chain form a first arm which comprises a first antigen binding domain that binds to B7-H4, and the second heavy chain and the second light chain forms a second arm which comprises a second antigen binding domain that binds to CD3, wherein (a) the first heavy chain comprises a VH CDR1 having the amino acid sequence of SEQ ID NO: 20; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153; (b) the first heavy chain comprises a VH CDR1 having the amino acid sequence of SEQ ID NO: 205; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153; (c) the first heavy chain comprises a VH CDR1 having the amino acid sequence of SEQ ID NO: 206; a VH CDR2 having the amino acid sequence of SEQ ID NO:207, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153; (d) the first heavy chain comprises a VH CDR1 having the amino acid sequence of SEQ ID NO: 5; a VH CDR2 having the amino acid sequence of SEQ ID NO:6, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138; (e) the first heavy chain comprises a VH CDR1 having the amino acid sequence of SEQ ID NO: 200; a VH CDR2 having the amino acid sequence of SEQ ID NO:201, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138; (f) the first heavy chain comprises a VH CDR1 having the amino acid sequence of SEQ ID NO: 199; a VH CDR2 having the amino acid sequence of SEQ ID NO:6, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138; (g) the first heavy chain comprises a VH CDR1 having the amino acid sequence of SEQ ID NO: 20; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 152, a VL CDR2 having the amino acid sequence of SEQ ID NO:41 and a VL CDR3 having the amino acid sequence of SEQ ID NO:153; (h) the first heavy chain comprises a VH CDR1 having the amino acid sequence of SEQ ID NO: 5; a VH CDR2 having the amino acid sequence of SEQ ID NO:6, a VH CDR3 having the amino acid sequence of SEQ ID NO:7, a VL CDR1 having the amino acid sequence of SEQ ID NO: 9, and the first light chain comprises a VL CDR2 having the amino acid sequence of SEQ ID NO:10 and a VL CDR3 having the amino acid sequence of SEQ ID NO:138; or (i) the first heavy chain comprises a VH CDR1 having the amino acid sequence of SEQ ID NO: 5; a VH CDR2 having the amino acid sequence of SEQ ID NO:130, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138.

In some embodiments of the bispecific antibody, (a) the first heavy chain comprises a VH having the amino acid sequence of SEQ ID NO:161, and the first light chain comprises a VL having the amino acid sequence of SEQ ID NO:167; (b) the first heavy chain comprises a VH having the amino acid sequence of SEQ ID NO:172, and the first light chain comprises a VL having the amino acid sequence of SEQ ID NO:139; (c) the first heavy chain comprises a VH having the amino acid sequence of SEQ ID NO:155; and the first light chain comprises a VL having the amino acid sequence of SEQ ID NO:139; (d) the first heavy chain comprises a VH having the amino acid sequence of SEQ ID NO:156; and the first light chain comprises a VL having the amino acid sequence of SEQ ID NO:139; (e) the first heavy chain comprises a VH having the amino acid sequence of SEQ ID NO:157; and the first light chain comprises a VL having the amino acid sequence of SEQ ID NO:141; (f) the first heavy chain comprises a VH having the amino acid sequence of SEQ ID NO:155; and the first light chain comprises a VL having the amino acid sequence of SEQ ID NO:141; (g) the first heavy chain comprises a VH having the amino acid sequence of SEQ ID NO:156; and the first light chain comprises a VL having the amino acid sequence of SEQ ID NO:141; (h) the first heavy chain comprises a VH having the amino acid sequence of SEQ ID NO:159; and the first light chain comprises a VL having the amino acid sequence of SEQ ID NO:27; (i) the first heavy chain comprises a VH having the amino acid sequence of SEQ ID NO:161; and the first light chain comprises a VL having the amino acid sequence of SEQ ID NO:27; (j) the first heavy chain comprises a VH having the amino acid sequence of SEQ ID NO:163; and the first light chain comprises a VL having the amino acid sequence of SEQ ID NO:27; (k) the first heavy chain comprises a VH having the amino acid sequence of SEQ ID NO:165; and the first light chain comprises a VL having the amino acid sequence of SEQ ID NO:27; (l) the first heavy chain comprises a VH having the amino acid sequence of SEQ ID NO:23; and the first light chain comprises a VL having the amino acid sequence of SEQ ID NO:167; (m) the first heavy chain comprises a VH having the amino acid sequence of SEQ ID NO:171; and the first light chain comprises a VL having the amino acid sequence of SEQ ID NO:141; (n) the first heavy chain comprises a VH having the amino acid sequence of SEQ ID NO:172; and the first light chain comprises a VL having the amino acid sequence of SEQ ID NO:141; (o) the first heavy chain comprises a VH having the amino acid sequence of SEQ ID NO:171; and the first light chain comprises a VL having the amino acid sequence of SEQ ID NO:139; (p) the first heavy chain comprises a VH having the amino acid sequence of SEQ ID NO:173; and the first light chain comprises a VL having the amino acid sequence of SEQ ID NO:139; (q) the first heavy chain comprises a VH having the amino acid sequence of SEQ ID NO:174; and the first light chain comprises a VL having the amino acid sequence of SEQ ID NO:139; (r) the first heavy chain comprises a VH having the amino acid sequence of SEQ ID NO:175; and the first light chain comprises a VL having the amino acid sequence of SEQ ID NO:139; (s) the first heavy chain comprises a VH having the amino acid sequence of SEQ ID NO:161; and a VL having the amino acid sequence of SEQ ID NO:168; (t) the first heavy chain comprises a VH having the amino acid sequence of SEQ ID NO:161; and the first light chain comprises a VL having the amino acid sequence of SEQ ID NO:169; (u) the first heavy chain comprises a VH having the amino acid sequence of SEQ ID NO:161; and the first light chain comprises a VL having the amino acid sequence of SEQ ID NO:170; or (v) the first heavy chain comprises a VH having the amino acid sequence of SEQ ID NO:172; and the first light chain comprises a VL having the amino acid sequence of SEQ ID NO:139.

In some embodiments of the bispecific antibody, (a) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34; (b) the second heavy chain comprises a VH CDR1 having the amino acid sequence of SEQ ID NO: 202, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34; (c) the second heavy chain comprises a VH CDR1 having the amino acid sequence of SEQ ID NO: 203, a VH CDR2 having the amino acid sequence of SEQ ID NO:204, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34; (d) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:116; (e) the second heavy chain comprises a VH CDR1 having the amino acid sequence of SEQ ID NO: 28, a VH CDR2 having the amino acid sequence of SEQ ID NO:109, a VH CDR3 having the amino acid sequence of SEQ ID NO:30, and the second light chain comprises a VL CDR1 having the amino acid sequence of SEQ ID NO: 111, a VL CDR2 having the amino acid sequence of SEQ ID NO:112 and a VL CDR3 having the amino acid sequence of SEQ ID NO:34; or (f) the second heavy chain comprises a VH CDR1 having the amino acid sequence of SEQ ID NO: 28, a VH CDR2 having the amino acid sequence of SEQ ID NO:29, a VH CDR3 having the amino acid sequence of SEQ ID NO:30, and the second light chain comprises a VL CDR1 having the amino acid sequence of SEQ ID NO: 32, a VL CDR2 having the amino acid sequence of SEQ ID NO:33 and a VL CDR3 having the amino acid sequence of SEQ ID NO:34.

In some embodiments of the bispecific antibody, (a) the second heavy chain comprises a VH having the amino acid sequence of SEQ ID NO: 106, and the second light chain comprises a VL having the amino acid sequence of SEQ ID NO: 108; (b) the second heavy chain comprises a VH having the amino acid sequence of SEQ ID NO: 115, and the second light chain comprises a VL having the amino acid sequence of SEQ ID NO: 117; (c) the second heavy chain comprises a VH having the amino acid sequence of SEQ ID NO: 110, and the second light chain comprises a VL having the amino acid sequence of SEQ ID NO: 113; or (d) the second heavy chain comprises a VH having the amino acid sequence of SEQ ID NO: 31, and the second light chain comprises a VL having the amino acid sequence of SEQ ID NO: 35.

In some embodiments of the bispecific antibody, (a) the first heavy chain comprises a VH CDR1 having the amino acid sequence of SEQ ID NO: 20; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153; and (b) second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34.

In some embodiments of the bispecific antibody, (a) the first heavy chain comprises a VH CDR1 having the amino acid sequence of SEQ ID NO: 5; a VH CDR2 having the amino acid sequence of SEQ ID NO:6, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138; and (b) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34.

In some embodiments of the bispecific antibody, (a) the first heavy chain comprises a VH having the amino acid sequence of SEQ ID NO:161, and the first light chain comprises a VL having the amino acid sequence of SEQ ID NO:167; and (b) the second heavy chain comprises a VH having the amino acid sequence of SEQ ID NO: 106, and the second light chain comprises a VL having the amino acid sequence of SEQ ID NO:108.

In some embodiments of the bispecific antibody, (a) the first heavy chain comprises a VH having the amino acid sequence of SEQ ID NO:172, and the first light chain comprises a VL having the amino acid sequence of SEQ ID NO:139; and (b) the second heavy chain comprises a VH having the amino acid sequence of SEQ ID NO: 106, and the second light chain comprises a VL having the amino acid sequence of SEQ ID NO:108.

In some embodiments, the bispecific antibody further comprises a constant region. In some embodiments, the constant region is an IgG1. In some embodiments, the constant region is human IgG2, comprising one or more substitutions selected from the group consisting of A330S, P331S, D265A, C223E, P228E, L368E, C223R, E225R, P228R, and K409R, wherein the numbering is according to human IgG2 wildtype and the EU numbering scheme, and as shown in FIG. 1.

In some embodiments of the bispecific antibody, the first arm further comprises a constant region of a hIgG2ΔA constant region with substitutions D265A, C223E, P228E, and L368E, the second arm further comprises a human IgG2ΔA constant region with substitutions D265A, C223R, E225R, P228R, and K409R, wherein the numbering is according to the human wildtype IgG2 and EU numbering schemes, and as shown in FIG. 1.

In one aspect, the invention provides a bispecific antibody that specifically binds to both B7-H4 and CD3, comprising a first heavy chain and a first light chain, and a second heavy chain and a second light chain, wherein the first heavy chain and the first light chain form a first antibody arm which comprises a first antigen binding domain that binds to B7-H4, and the second heavy chain and the second light chain form a second antigen binding domain that binds to CD3, wherein (a) the first heavy chain having the amino acid sequence of SEQ ID NO: 190; and the first light chain having the amino acid sequence of SEQ ID NO:191; and (b) the second heavy chain having the amino acid sequence of SEQ ID NO:188, and the second light chain having the amino acid sequence of 189.

In another aspect, the invention provides a bispecific antibody that specifically binds to both B7-H4 and CD3, comprising a first heavy chain and a first light chain, and a second heavy chain and a second light chain, wherein the first heavy chain and the first light chain form a first antibody arm which comprises a first antigen binding domain that binds to B7-H4, and the second heavy chain and the second light chain form a second antigen binding domain that binds to CD3, wherein (a) the first heavy chain having the amino acid sequence of SEQ ID NO: 186; and the first light chain having the amino acid sequence of SEQ ID NO: 187; and (b) the second heavy chain having the amino acid sequence of SEQ ID NO:188, and the second light chain having the amino acid sequence of 189.

In another aspect, the invention provides a bispecific antibody that specifically binds to B7-H4 and CD3, comprising a first heavy chain and a first light chain, and a second heavy chain and a second light chain, wherein the first heavy chain and the first light chain form a first antibody arm which comprises a first antigen binding domain that binds to B7-H4, and the second heavy chain and the second light chain form a second antigen binding domain that binds to CD3, wherein (a) the first heavy chain comprises the amino acid sequence of the full-length polypeptide encoded by the open reading frame (ORF) deposited under ATCC Accession No. PTA-126779, and the first light chain comprises the amino acid sequence of the full-length polypeptide encoded by the open reading frame (ORF) deposited under ATCC Accession No. PTA-126781; and (b) the second heavy chain comprises the amino acid sequence of the full-length polypeptide encoded by the open reading frame (ORF) deposited under ATCC Accession No. PTA-126780, and the second light chain comprises the amino acid sequence of the full-length polypeptide encoded by the open reading frame (ORF) deposited under ATCC Accession No. PTA-126782.

In another aspect, the invention provides a bispecific antibody that specifically binds to both B7-H4 and CD3, wherein the antibody binds to an epitope on human B7-H4 comprising at least two at least three, at least four, at least five, at least six, at least seven, at least eight, at least nine, at least ten, at least eleven, at least twelve, or at least thirteen amino acid residues from the group consisting of L44, K45, E46, G47, V48, L49, G50, L51, S63, E64, D66, M68, T99 and K101 of the B7-H4 amino acid sequence of SEQ ID NO: 1. In some embodiments, epitope comprises at least one, at least two, at least three, at least four, at least five, at least six or at least seven amino acid residues from the group consisting of L44, K45, E46, G47, V48, L49, G50 and L51, and at least one amino, at least two, at least three, at least four or at least five acid residues from the group consisting of S63, E64, D66, M68, T99 and K101. In some embodiments, the epitope comprises or consists of the amino acid residues of L44, K45, E46, G47, V48, L49, G50, L51, S63, E64, D66, M68, T99 and K101.

In another aspect, the invention provides a bispecific antibody that specifically binds to both B7-H4 and CD3, wherein the antibody binds to an epitope on human B7-H4 comprising at least two, at least three, at least four, at least five, at least six, at least seven, at least eight, at least nine, at least ten, at least eleven, at least twelve, or at least thirteen amino acid residue from the group consisting of V129, Y131, N132, S134, S135, E136, L138, V189, I191, V212, E214, S215, E216 and I217 of the B7-H4 amino acid sequence of SEQ ID NO: 1. In some embodiments, the epitope comprises at least one, at least two, at least three, at least four, at least five, or at least six amino acid residue from the group consisting of V129, Y131, N132, S134, S135, E136 and L138, and at least one, cat least two, at least three, at least four, at least five or at least six amino acid residue from the group consisting of V189, I191, V212, E214, S215, E216 and I217. In some embodiments, epitope comprises or consists of the amino acid residues of V129, Y131, N132, S134, S135, E136, L138, V189, I191, V212, E214, S215, E216 and I217.

In another aspect, the invention provides a polynucleotide encoding a bispecific antibody of the present invention.

In another aspect, the invention provides a polynucleotide encoding (i) a heavy chain of the bispecific antibody of the present invention or (ii) a light chain of the bispecific antibody of the present invention.

In another aspect, the invention provides a vector comprising a polynucleotide of the present invention.

In another aspect, the invention provides a host cell comprising a polynucleotide disclosed herein or a vector disclosed herein.

In another aspect, the present invention provides a bispecific antibody disclosed herein for use as a medicament. In some embodiments, the medicament can be for the treatment of cancer.

In another aspect, the present invention provides a method of treating cancer in a subject in need comprising administering to the subject a bispecific antibody disclosed herein.

In another aspect, the present invention provides a pharmaceutical composition comprising a bispecific antibody disclosed herein.

In another aspect, the present invention provides a method of treating a condition associated with malignant cells expressing B7-H4 in a subject comprising administering to the subject in need thereof a therapeutically effective amount of a pharmaceutical composition disclosed herein.

In another aspect, the present invention provides a B7-H4 antibody, a bispecific antibody, a pharmaceutical composition, a polynucleotide, a vector, or a host cell as disclosed herein, for use as a medicament.

In another aspect, the present invention provides a use of a B7-H4 antibody, a bispecific antibody, a pharmaceutical composition, a polynucleotide, a vector, or a host cell as disclosed herein, in the manufacture of a medicament.

In some embodiments, the condition is a cancer. In some embodiments, the cancer is breast cancer, ovarian cancer, cancer of the uterus, bladder cancer or cancer of the bile duct. In some embodiments, the method or use can further comprise administering an effective amount of a second therapeutic agent. In some embodiments, the second therapeutic agent is an anti-PD-1 or anti-PD-L1 antibody, or palbociclib. In some embodiments, the anti-PD-1 antibody is RN888.

In another aspect, the present invention provides a method of inhibiting tumor growth or progression in a subject who has malignant cells expressing B7-H4, comprising administering to the subject in need thereof a therapeutically effective amount of a pharmaceutical composition disclosed herein.

In another aspect, the present invention provides a B7-H4 antibody, a bispecific antibody, a pharmaceutical composition, a polynucleotide, a vector, or a host cell as disclosed herein, for use in inhibiting tumor growth or progression in a subject who has malignant cells expressing B7-H4

In another aspect, the present invention provides a use of a B7-H4 antibody, a bispecific antibody, a pharmaceutical composition, a polynucleotide, a vector, or a host cell as disclosed herein, in the manufacture of a medicament for inhibiting tumor growth or progression in a subject who has malignant cells expressing B7-H4.

In some embodiments, the method or use can further comprise administering an effective amount of a second therapeutic agent. In some embodiments, the second therapeutic agent is an anti-PD-1 or anti-PD-L1 antibody, or palbociclib. In some embodiments, the anti-PD-1 antibody is RN888.

In another aspect, the present invention provides a method of inducing tumor regression in a subject who has malignant cells expressing B7-H4, comprising administering to the subject in need thereof an effective amount of a pharmaceutical composition disclosed herein.

In another aspect, the present invention provides a B7-H4 antibody, a bispecific antibody, a pharmaceutical composition, a polynucleotide, a vector, or a host cell as disclosed herein, for use in inducing tumor regression in a subject who has malignant cells expressing B7-H4 In another aspect, the present invention provides a use of a B7-H4 antibody, a pharmaceutical composition, a polynucleotide, a vector, or a host cell as disclosed herein, in the manufacture of a medicament for inducing tumor regression in a subject who has malignant cells expressing B7-H4.

In some embodiments, the method or use can further comprise administering an effective amount of a second therapeutic agent. In some embodiments, the second therapeutic agent is an anti-PD-1 or anti-PD-L1 antibody, or palbociclib. In some embodiments, the anti-PD-1 antibody is RN888.

In some embodiments, the antibody or the bispecific antibody of the present invention demonstrates a lower EC50 value in the presence of increased B7-H4 receptor density levels. Preferably, the EC50 value is between 0.0001 nM and 100 nM, between 0.0001 nM and 10 nM, 0.0001 nM and 1 nm, 0.0001 nM and 0.1 nm, between 0.0001 nM and 0.0010 nM, between 0.001 nM and 100 nM, 0.01 nM and 100 nM, 0.1 nM and 100 nM, between 0.001 nM and 10 nM, between 0.001 nM and 1 nM, between 0.01 nM and 1 nM, or between 0.001 nM and 0.1 nM. Preferably, the EC50 value is less than 10 nM, less than 1 nM, less than 0.5 nM, less than 0.1 nM, less than 0.01 nM or less than 0.001 nm.

In some embodiments, the antibody or the bispecific antibody of the present invention is capable of activating a cytolytic T cell response.

BRIEF DESCRIPTION OF THE FIGURES/DRAWINGS

FIG. 1 depicts the amino acid sequences of exemplary IgG2 constant regions of the bispecific antibodies provided herein with modifications at various positions in the constant region, numbered according to the human IgG2 wildtype sequence and using the EU numbering scheme. Human IgG1 and IgG4 wildtype sequences and numbering are also provided in FIG. 1.

DETAILED DESCRIPTION

Figure 2A:
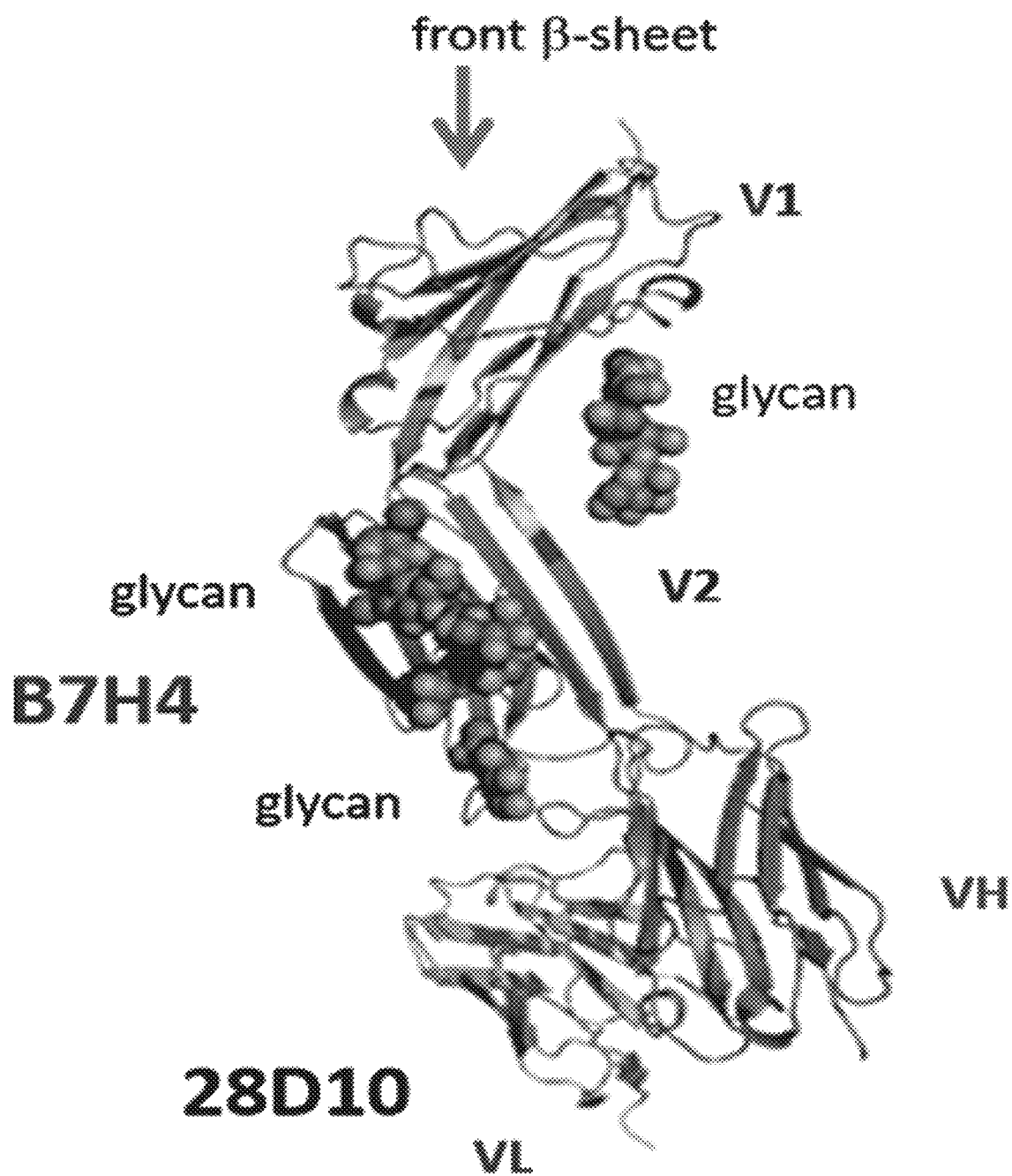
FIG. 2A depicts the co-crystal structure of B7-H4 antibody 0052 scFv and human B7-H4 extracellular domain.

Disclosed herein are antibodies that specifically bind to B7-H4, including bispecific antibodies that specifically bind to B7-H4 and CD3 ("B7-H4×CD3 bispecific antibodies"), methods of making such antibodies, and methods of using such antibodies, including to inhibit tumor progression and to treat and/or prevent cancer.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen binding fragments thereof such as, for example, Fab, Fab', F(ab')$_2$, Fv, single chain (ScFv) and domain antibodies (including, for example, shark and camelid antibodies), fusion proteins comprising an antibody (including, for example without limitation, a chimeric antigen receptor (CAR), or an antibody-cytokine fusion protein), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy chain constant regions that correspond to the different classes of immunoglobulins are called alpha, delta, epsilon, gamma, and mu, respectively. The subunit structures and three-dimensional configurations of different classes of immunoglobulins are well known.

An "isolated antibody" refers to an antibody that is substantially free of other proteins and cellular materials.

The term "antigen binding fragment" or "antigen binding portion" of an antibody, as used herein, refers to one or more fragments of an intact antibody that retain the ability to specifically bind to a given antigen (e.g., B7-H4 or CD3). Antigen binding functions of an antibody can be performed by fragments of an intact antibody. Examples of binding fragments encompassed within the term "antigen binding fragment" of an antibody include, without limitation, Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., B7-H4 protein or CD3 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a B7-H4 epitope or CD3 epitope is an antibody that binds this epitope with greater affinity, avidity, more readily, and/or with greater duration than it binds to other B7-H4 epitopes, non-B7-H4 epitopes, CD3 epitopes, or non-CD3 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" refers to antibodies in which the variable region sequences are derived from one species and the constant region sequences are derived from another species, such as an antibody in which the variable region sequences are derived from a mouse antibody and the constant region sequences are derived from a human antibody.

The term "B7-H4" when using as a noun and by itself, refers to any forms of the B7 Homology 4 protein encoded by gene VTCN1, and variants thereof that retains at least part of the activity of the B7 Homology 4 protein. One exemplary human B7-H4 sequence is provided under UniProt identifier Q7Z7D3-1. The displayed sequence in Q7Z7D3-1 is further processed into a mature form.

The term "B7-H4 antibody", refers to an antibody that specifically binds to B7-H4.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention, for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "monospecific antibody" comprises two identical antigen binding sites per molecule (e.g. IgG) such that the two binding sites bind identical epitope on the antigen. Thus, they compete with each other on binding to one antigen molecule. Most antibodies found in nature are monospecific. In some instances, a monospecific antibody can also be a monovalent antibody (e.g. Fab)

A "bivalent antibody" comprises two antigen binding sites per molecule (e.g., IgG). In some instances, the two binding sites have the same antigen specificities. However, bivalent antibodies may be bispecific.

The term "bispecific antibody" or "dual-specific antibody" as used herein refers to a hybrid antibody having two different binding specificities, e.g., two different heavy/light chain pairs, giving rise to two antigen binding sites with specificity for different antigens.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., *Protein Science* (1997), 6:407-415; Humphreys et al., *J. Immunol. Methods* (1997), 209:193-202.

The "immunoglobulin-like hinge region," "immunoglobulin-like hinge sequence," and variations thereof, as used herein, refer to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

The term "immune effector cell" or "effector cell as used herein refers to a cell within the natural repertoire of cells in the human immune system which can be activated to affect the viability of a target cell. The viability of a target cell can include cell survival, proliferation, and/or ability to interact with other cells.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, remission of a B7-H4 associated disease (e.g., cancer or autoimmune disease), decreasing symptoms resulting from a B7-H4 associated disease (e.g., cancer or autoimmune disease), increasing the quality of life of those suffering from a B7-H4 associated disease (e.g., cancer or autoimmune disease), decreasing the dose of other medications required to treat a B7-H4 associated disease (e.g., cancer or autoimmune disease), delaying the progression of a B7-H4 associated disease (e.g., cancer or autoimmune disease), curing a B7-H4 associated disease (e.g., cancer or autoimmune disease), and/or prolong survival of patients having a B7-H4 associated disease (e.g., cancer or autoimmune disease).

"Ameliorating" means a lessening or improvement of one or more symptoms as compared to not administering a B7-H4 antibody or a B7-H4 antibody conjugate. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various B7-H4-associated diseases or conditions (such as cancer), decreasing the dose of other medications required to treat the disease, enhancing the effect of another medication, and/or delaying the progression of the B7-H4-associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

The term "$k_{on}$" or "$k_a$", as used herein, refers to the rate constant for association of an antibody to an antigen. Specifically, the rate constants ($k_{on}/k_a$ and $k_{off}/k_d$) and equilibrium dissociation constants are measured using whole antibody (i.e. bivalent) and monomeric B7-H4 proteins.

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

General Method in Making Antibodies

General techniques for production of human and mouse antibodies that specifically binds to a target antigen, for example in the present invention, B7-H4, are known in the art and/or are described herein.

Phage Display:

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Hybridoma Technology:

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the B7-H4 monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for the target antigen, e.g. B7-H4, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with an antigen, e.g. a B7-H4 polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

Recombinant Antibodies

If desired, the antibody (monoclonal or polyclonal) of interest, e.g., an antibody generated under the hybridoma technology, may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, CA) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for a target antigen, e.g. B7-H4.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity to the target antigen, e.g. B7-H4.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

Recombinant Antibodies—Affinity Maturation

Antibodies can be modified by a method generally known as affinity maturation. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Kinexa™ biosensor analysis, and selection using any method known in the art for selection, including phage display, yeast display, and ribosome display.

To express the antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The amino acid sequence of the antibody can be modified to comprise functionally equivalent variable regions and/or CDRs which do not significantly affect properties of the antibody as well as variants which have enhanced or decreased activity and/or affinity. Examples of such modifications include conservative substitutions of amino acid residues, one or more deletions or additions of amino acids which do not significantly deleteriously change the functional activity of the antibody, or which mature (enhance) the affinity of the antibody to its target antigen.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and (6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody to B7-H4, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an B7-H4 antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. In some embodiments, no more than one to five conservative amino acid substitutions are made within the framework region or constant region. In other embodiments, no more than one to three conservative amino acid substitutions are made within the framework region or constant region. According to the invention, a single antibody may have mutations in any one or more of the CDRs or framework regions of the variable domain or in the constant region.

Recombinant Antibodies—Glycosylation Modification:

Modifications of the antibodies provided herein also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, orxylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

Recombinant Antibodies—Germlining:

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Recombinant Antibodies—Removing Liability Sites:

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an antibody of the invention can be cleaved. In various embodiments of the invention, the heavy and light chains of the antibodies may optionally include a signal sequence.

Recombinant Antibodies—Various Forms:

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$, which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to the target antigen, e.g. B7-H4, and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

A fusion antibody may be made that comprises all or a portion of a monoclonal antibody linked to another polypeptide. In some embodiment, only the variable domains of an antibody are linked to the other polypeptide. In another embodiment, the VH domain of an antibody is linked to a first polypeptide, while the VL domain of an antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the other polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

A fusion antibody can be created by methods known in the art, for example, synthetically or recombinantly. Typically, the fusion antibody are made by preparing and expressing a polynucleotide encoding them using recombinant methods described herein, although they may also be prepared by other means known in the art, including, for example, chemical synthesis.

In other embodiments, other modified antibodies may be prepared using antibody encoding nucleic acid molecules. For instance, "Kappa bodies" (III et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

Bispecific Antibodies

Methods for making bispecific antibodies are known in the art (see, e.g., Suresh et al., 1986, Methods in Enzymology 121:210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins."

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

Antibodies Conjugated to an Agent for Coupling to a Solid Support

This invention also provides compositions comprising antibodies conjugated (for example, linked) to an agent that facilitate coupling to a solid support (such as biotin or avidin). For simplicity, reference will be made generally to antibodies with the understanding that these methods apply to any of the antibody embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the lung, heart, or heart valve.

An antibody or polypeptide of this invention may be linked to a labeling agent such as a fluorescent molecule, a radioactive molecule or any other labels known in the art. Labels are known in the art which generally provide (either directly or indirectly) a signal.

B7-H4 Antibodies

The present invention provides antibodies that specifically bind to B7-H4 ("B7-H4 antibodies"). A B7-H4 antibody of the present invention should exhibit any one of the following characteristics: (a) binds to a plate bound B7-H4 in an ELISA assay; (b) binds to a B7-H4 expressing tumor cell in a cell based assay; (c) exhibit activity in T cell mediated tumor cell killing where the tumor cells express B7-H4; (d) inhibit tumor growth or progression in a subject that has a malignant tumor expressing B7-H4; (e) treat, prevent, ameliorate one or more symptoms of a condition associated with malignant cells expressing B7-H4 in a subject.

The B7-H4 antibodies may be made by any method known in the art. Table 2 describes exemplary B7-H4 antibodies of the present invention. Each of the VH CDR1 (heavy chain variable region CDR1) listed in Table 2 is according to the AbM CDR definition. Each of the VH CDR2 (heavy chain variable region CDR2), VH CDR3 (heavy chain variable region CDR3), VLCDR1 (light chain variable region CDR1), VL CDR2 (light chain variable region CDR2), VLCDR3 (light chain variable region CDR3) sequences listed in Table 2 is according to the Kabat CDR definition.

Accordingly, in some embodiments, the invention provides any one of the B7-H4 antibodies described in Table 2.

In some embodiments, the invention provides a B7-H4 antibody, or a variant thereof that binds to B7-H4, or an antigen binding fragment thereof that binds to B7-H4, wherein the B7-H4 antibody comprising a VH and a VL having the same amino acid sequence of that of the VH and VL of an antibody described in Table 2.

In some embodiments, the invention provides a B7-H4 antibody, or a variant thereof that binds to B7-H4, or an antigen binding fragment thereof that binds to B7-H4, wherein the B7-H4 antibody comprising
(i) a VH CDR1, a VH CDR2, a VH CDR3, a VL CDR1, a VL CDR2 and a VL CDR3, wherein the six CDRs each having the same amino acid sequence as the corresponding CDR of the VH and VL of an antibody described in Table 2,
(ii) three CDRs of the VH of any of the antibodies described in Table 2, or
(iii) three CDRs of the VL of any of the antibodies described in Table 2, wherein the CDRs are defined according to the Kabat definition, the Chothia definition. the AbM definition, or a combination of the Kabat and Chothia CDR (also termed "combined CDRs" or "extended CDRs").

In some embodiments, the invention provides a B7-H4 antibody, or a variant thereof that binds to B7-H4, or an antigen binding fragment thereof that binds to B7-H4, wherein the B7-H4 antibody comprises a VH CDR1, a VH CDR2, a VH CDR3, a VL CDR1, a VL CDR2 and a VL CDR3, each of which having the same amino acid sequence as the corresponding CDR listed in Table 2 of any of the antibody described in Table 2.

In some embodiments, the invention provides a B7-H4 antibody that competes for binding to B7-H4 with any one of the antibodies described in Table 2.

TABLE 2

SEQ ID NOs of the Exemplary B7-H4 Antibodies

Antibody Portion Sequence Identifier (SEQ ID NO:)

| Antibody Name | VH CDR1 | VH CDR2 | VH CDR3 | VL CDR1 | VL CDR2 | VL CDR3 | CH | CL | VH | VL |
|---|---|---|---|---|---|---|---|---|---|---|
| 0001 | 5 | 6 | 7 | 9 | 10 | 11 | 177 | 12 | 8 | 13 |
| 0007 | 5 | 14 | 15 | 9 | 17 | 18 | 177 | 12 | 16 | 19 |
| 0013 | 20 | 21 | 22 | 24 | 25 | 26 | 177 | 12 | 23 | 27 |
| 0047 | 5 | 6 | 7 | 9 | 10 | 11 | 179 | 12 | 8 | 13 |
| 0048 | 36 | 37 | 38 | 40 | 41 | 42 | 179 | 12 | 39 | 43 |
| 0049 | 20 | 44 | 45 | 47 | 41 | 48 | 179 | 12 | 46 | 49 |
| 0050 | 5 | 50 | 51 | 9 | 10 | 53 | 179 | 12 | 52 | 54 |
| 0051 | 20 | 55 | 56 | 47 | 58 | 59 | 179 | 12 | 57 | 60 |
| 0052 | 5 | 14 | 15 | 9 | 17 | 18 | 179 | 12 | 16 | 19 |
| 0053 | 61 | 62 | 63 | 47 | 65 | 66 | 179 | 12 | 64 | 67 |
| 0054 | 5 | 6 | 68 | 9 | 10 | 11 | 179 | 12 | 69 | 70 |
| 0055 | 71 | 72 | 73 | 75 | 33 | 76 | 179 | 12 | 74 | 77 |
| 0056 | 78 | 44 | 79 | 81 | 82 | 83 | 179 | 12 | 80 | 84 |
| 0057 | 20 | 85 | 86 | 88 | 41 | 89 | 179 | 12 | 87 | 90 |
| 0058 | 20 | 21 | 22 | 24 | 25 | 26 | 179 | 12 | 23 | 27 |
| 0059 | 91 | 92 | 93 | 75 | 33 | 95 | 179 | 12 | 94 | 96 |
| 0060 | 97 | 98 | 99 | 75 | 33 | 76 | 179 | 12 | 100 | 77 |
| 0061 | 101 | 102 | 103 | 47 | 65 | 66 | 179 | 12 | 104 | 67 |
| 0119 | 20 | 21 | 22 | 24 | 25 | 26 | 179 | 12 | 23 | 118 |
| 0185 | 5 | 14 | 15 | 9 | 17 | 18 | 179 | 12 | 16 | 119 |
| 0267 | 5 | 14 | 15 | 9 | 17 | 18 | 179 | 121 | 120 | 19 |
| 0270 | 5 | 14 | 15 | 9 | 17 | 18 | 179 | 121 | 16 | 122 |
| 0274 | 20 | 21 | 22 | 24 | 25 | 26 | 179 | 121 | 23 | 123 |
| 0277 | 5 | 6 | 7 | 9 | 10 | 11 | 179 | 121 | 124 | 13 |
| 0279 | 5 | 6 | 7 | 9 | 10 | 11 | 179 | 121 | 125 | 13 |
| 0283 | 5 | 6 | 7 | 9 | 10 | 11 | 179 | 121 | 8 | 126 |
| 0350 | 127 | 6 | 7 | 9 | 10 | 11 | 179 | 12 | 128 | 13 |
| 0352 | 5 | 6 | 7 | 9 | 10 | 11 | 179 | 12 | 129 | 13 |
| 0362 | 5 | 130 | 7 | 9 | 10 | 11 | 179 | 12 | 131 | 13 |
| 0364 | 5 | 6 | 7 | 9 | 10 | 11 | 179 | 12 | 132 | 13 |
| 0368 | 5 | 6 | 7 | 9 | 10 | 11 | 179 | 12 | 133 | 13 |
| 0376 | 5 | 134 | 7 | 9 | 10 | 11 | 179 | 12 | 135 | 13 |
| 0380 | 5 | 6 | 136 | 9 | 10 | 11 | 179 | 12 | 137 | 13 |
| 0383 | 5 | 6 | 7 | 9 | 10 | 138 | 179 | 12 | 8 | 139 |
| 0384 | 5 | 6 | 7 | 9 | 10 | 140 | 179 | 12 | 8 | 141 |
| 0385 | 5 | 6 | 7 | 9 | 10 | 142 | 179 | 12 | 8 | 143 |
| 0386 | 5 | 6 | 7 | 9 | 10 | 144 | 179 | 12 | 8 | 145 |
| 0388 | 5 | 6 | 7 | 9 | 10 | 146 | 179 | 12 | 8 | 147 |
| 0390 | 5 | 6 | 7 | 9 | 10 | 148 | 179 | 12 | 8 | 149 |
| 0391 | 5 | 6 | 7 | 9 | 10 | 150 | 179 | 12 | 8 | 151 |
| 0414 | 20 | 21 | 22 | 152 | 25 | 153 | 179 | 12 | 23 | 154 |
| 0538 | 5 | 130 | 7 | 9 | 10 | 138 | 179 | 12 | 155 | 139 |
| 0540 | 5 | 130 | 136 | 9 | 10 | 138 | 179 | 12 | 156 | 139 |
| 0542 | 5 | 130 | 136 | 9 | 10 | 140 | 179 | 12 | 157 | 141 |
| 0544 | 5 | 130 | 7 | 9 | 10 | 140 | 179 | 12 | 155 | 141 |
| 0546 | 5 | 130 | 136 | 9 | 10 | 140 | 179 | 12 | 156 | 141 |
| 0562 | 20 | 158 | 22 | 24 | 25 | 26 | 179 | 12 | 159 | 27 |

TABLE 2-continued

SEQ ID NOs of the Exemplary B7-H4 Antibodies

Antibody Portion Sequence Identifier (SEQ ID NO:)

| Antibody Name | VH CDR1 | VH CDR2 | VH CDR3 | VL CDR1 | VL CDR2 | VL CDR3 | CH | CL | VH | VL |
|---|---|---|---|---|---|---|---|---|---|---|
| 0563 | 20 | 21 | 160 | 24 | 25 | 26 | 179 | 12 | 161 | 27 |
| 0564 | 20 | 21 | 162 | 24 | 25 | 26 | 179 | 12 | 163 | 27 |
| 0565 | 20 | 21 | 164 | 24 | 25 | 26 | 179 | 12 | 165 | 27 |
| 0567 | 20 | 21 | 22 | 166 | 25 | 153 | 179 | 12 | 23 | 167 |
| 0570 | 20 | 21 | 22 | 152 | 41 | 153 | 179 | 12 | 23 | 168 |
| 0571 | 20 | 21 | 22 | 152 | 41 | 153 | 179 | 12 | 23 | 169 |
| 0572 | 20 | 21 | 22 | 152 | 41 | 153 | 179 | 12 | 23 | 170 |
| 0911 | 5 | 6 | 7 | 9 | 10 | 140 | 179 | 12 | 171 | 141 |
| 0934 | 5 | 6 | 7 | 9 | 10 | 140 | 179 | 12 | 172 | 141 |
| 1070 | 5 | 6 | 7 | 9 | 10 | 138 | 181 | 12 | 172 | 139 |
| 1080 | 5 | 6 | 7 | 9 | 10 | 138 | 179 | 12 | 171 | 139 |
| 1081 | 5 | 130 | 7 | 9 | 10 | 138 | 179 | 12 | 173 | 139 |
| 1082 | 5 | 6 | 7 | 9 | 10 | 138 | 179 | 12 | 174 | 139 |
| 1083 | 5 | 6 | 7 | 9 | 10 | 138 | 179 | 12 | 175 | 139 |
| 1103 | 5 | 6 | 7 | 9 | 10 | 138 | 179 | 12 | 172 | 139 |
| 1113 | 20 | 21 | 160 | 152 | 25 | 153 | 179 | 12 | 161 | 154 |
| 1114 | 20 | 21 | 160 | 166 | 25 | 153 | 179 | 12 | 161 | 167 |
| 1115 | 20 | 21 | 160 | 152 | 41 | 153 | 179 | 12 | 161 | 168 |
| 1116 | 20 | 21 | 160 | 152 | 41 | 153 | 179 | 12 | 161 | 169 |
| 1117 | 20 | 21 | 160 | 152 | 41 | 153 | 179 | 12 | 161 | 170 |
| 1124 | 20 | 21 | 160 | 166 | 25 | 153 | 181 | 12 | 161 | 167 |
| 1174 | 5 | 6 | 7 | 9 | 10 | 138 | 177 | 12 | 172 | 139 |
| 1177 | 20 | 21 | 160 | 166 | 25 | 153 | 177 | 12 | 161 | 167 |

Table 3 shows the sequences, with corresponding sequence identifiers, of the exemplary antibodies of this invention, including the B7-H4 antibodies listed in Table 2, the CD3 antibodies listed in Table 4 and the B7-H4×CD3 bispecific antibodies listed in Table 5, and the sequences of the B7-H4 extracellular domains that were used to either generate or test the antibodies of the current invention. Kabat CDRs of several VH and VL sequences, namely, SEQ ID NOs 106, 108, 139, 161, 167 and 172 are marked as underlined amino acid sequences, and the Chothia CDRs are marked as bolded amino acid sequences. Besides the sequences described in Table 2, Table 4 and Table 5, below are the descriptions of some additional sequences included in Table 3.

SEQ ID NO: 1 is the amino acid sequence of the extracellular domain of the human B7-H4 protein.

SEQ ID NO: 2 is the amino acid sequence of the extracellular domain of the cyno B7-H4 protein.

SEQ ID NO: 3 is the amino acid sequence of the extracellular domain of the mouse B7-H4 protein.

SEQ ID NO: 4 is the amino acid sequence of the extracellular domain of the rat B7-H4 protein.

Antibody 1156 and antibody 1167 are B7-H4×CD3 bispecific antibodies; both are described in Table 5.

SEQ ID NOs: 186 and 187 respectively are the amino acid sequences of the full-length heavy chain and full-length light chain of the first arm (B7-H4 arm) of bispecific antibody 1156.

SEQ ID NOs: 188 and 189 respectively are the amino acid sequence of the full-length heavy chain and full-length light chain respectively of the second arm (CD3 arm) of bispecific antibody 1156, and bispecific antibody 1167.

SEQ ID NOs: 190 and 191 respectively are the amino acid sequence of the full-length heavy chain and full-length light chain respectively of the first arm (B7-H4 arm) of bispecific antibody 1167;

SEQ ID NO: 192 is a nucleotide sequence that encodes the full-length heavy chain of the first arm (B7-H4 arm) of bispecific antibody 1156.

SEQ ID NO: 193 is a nucleotide sequence that encodes the full-length light chain of the first arm (B7-H4 arm) of bispecific antibody 1156.

SEQ ID NO: 194 is a nucleotide sequence that encodes the full-length heavy chain of the second arm (CD3 arm) of bispecific antibodies 1156 and 1167

SEQ ID NO: 195 is a nucleotide sequence that encodes the full-length light chain of the second arm (CD3 arm) of bispecific antibodies 1156 and 1167.

SEQ ID NO: 196 is a nucleotide sequence that encodes the full-length heavy chain of the first arm (B7-H4 arm) of bispecific antibody 1167.

SEQ ID NO: 197 is a nucleotide sequence that encodes the full-length light chain of the first arm (B7-H4 arm) of bispecific antibody 1167.

SEQ ID NO: 198 is the amino acid sequence of the (GGGGS)$_3$ peptide linker described in the General Method of Making Antibodies herein.

SEQ ID NO: 199 is the sequence of the Kabat VH CDR1 of the first arm (B7-H4 arm) of bispecific antibody 1156.

SEQ ID NO: 200 is the sequence of the Chothia VH CDR1 of the first arm (B7-H4 arm) of bispecific antibody 1156.

SEQ ID NO: 201 is the sequence of the Chothia VH CDR2 of the first arm (B7-H4 arm) of bispecific antibody 1156.

SEQ ID NO: 202 is the sequence of the Kabat VH CDR1 of the second arm (CD3 arm) of bispecific antibody 1156 and bispecific antibody 1167.

SEQ ID NO: 203 is the sequence of the Chothia VH CDR1 of the second arm (CD3 arm) of bispecific antibody 1156 and bispecific antibody 1167.

SEQ ID NO: 204 is the sequence of the Chothia VH CDR2 of the second arm (CD3 arm) of bispecific antibody 1156 and bispecific antibody 1167.

SEQ ID NO: 205 is the sequence of the Kabat VH CDR1 of the first arm (B7-H4 arm) of bispecific antibody 1167.

SEQ ID NO: 206 is the sequence of the Chothia VH CDR1 of the first arm (B7-H4 arm) of bispecific antibody 1167.

SEQ ID NO: 207 is the sequence of the Chothia VH CDR2 of the first arm (B7-H4 arm) of bispecific antibody 1167.

SEQ ID NO: 208 is the amino acid sequence of constant region 1 (CH1) hinge, CH2, and CH3 regions of a human IgG2 wild type IGHG*01.

SEQ ID NO: 209 is the amino acid sequence of CH1, hinge, CH2 and CH3 regions of a human IgG1 wild type IGHG1*01.

SEQ ID NO: 210 is the amino acid sequence of CH1, hinge, CH2 and CH3 regions a human IgG4 wild type IGHG4*01.

IGHG2*01, IGHG1*01 and IGHG4*01 are according to the human IGHC group of the IMGT/Gene-DB (Giudicelli, V. et al. Nucleic Acids Res., 33: D256-D261 (2005))

TABLE 3

SEQ ID NO Sequences

| SEQ ID NO | SEQUENCES |
|---|---|
| 1 | FGISGRHSIT VTTVASAGNI GEDGILSCTF EPDIKLSDIV IQWLKEGVLG LVHEFKEGKD ELSEQDEMFR GRTAVFADQV IVGNASLRLK NVQLTDAGTY KCYIITSKGK GNANLEYKTG AFSMPEVNVD YNASSETLRC EAPRWFPQPT VVWASQVDQG ANFSEVSNTS FELNSENVTM KVVSVLYNVT INNTYSCMIE NDIAKATGDI KVTESEIKRR SHLQLLNSKA |
| 2 | FGISGRHSIT VTTVASAGNI GEDGILSCTF EPDIKLSDIV IQWLKEGVIG LVHEFKEGKD ELSEQDEMFR GRTAVFADQV IVGNASLRLK NVQLTDAGTY KCYIITSKGK GNANLEYKTG AFSMPEVNVD YNASSETLRC EAPRWFPQPT VVWASQVDQG ANFSEVSNTS FELNSENVTM KVVSVLYNVT INNTYSCMIE NDIAKATGDI KVTESEIKRR SHLQLLNSKA |
| 3 | FGISGKHFIT VTTFTSAGNI GEDGTLSCTF EPDIKLNGIV IQWLKEGIKG LVHEFKEGKD DLSQQHEMFR GRTAVFADQV VVGNASLRLK NVQLTDAGTY TCYIRTSKGK GNANLEYKTG AFSMPEINVD YNASSESLRC EAPRWFPQPT VAWASQVDQG ANFSEVSNTS FELNSENVTM KVVSVLYNVT INNTYSCMIE NDIAKATGDI KVTDSEVKRR SQLQLLNSGP |
| 4 | FGISGKHFIT VTTFTSAGNI GEDGTLSCTF EPDIKLNGIV IQWLKEGIKG LVHEFKEGKD DLSQQHEMFR GRTAVFADQV VVGNASLRLK NVQLTDAGTY TCYIHTSKGK GNANLEYKTG AFSMPEINVD YNASSESLRC EAPRWFPQPT VAWASQVDQG ANFSEVSNTS FELNSENVTM KVVSVLYNVT INNTYSCMIE NDIAKATGDI KVTDSEVKRR SQLELLNSG |
| 5 | GGSFSGYYWN |
| 6 | EINHSGSATY NPSLKS |
| 7 | GLYNWNVDH |
| 8 | QVQLQQWGAG LLKPSETLPL TCAVYGGSFS GYYWNWIRQP PGKGLEWIGE INHSGSATYN PSLKSRVTIS VDTSKNHFSL KLSSVTAADT AVYFCARGLY NWNVDHWGQG TLVTVSS |
| 9 | RASQGIRNDL G |
| 10 | AASSLQS |
| 11 | LQHNSYPRT |
| 12 | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 13 | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPRTFGG GTKVEIK |
| 14 | EINHSGSTKY NPSLKS |
| 15 | GLYNWNVDS |
| 16 | QVQLQQWGAG LLKPSETLSL TCAVYGGSFS GYYWNWIRQP PGKGLEWIGE INHSGSTKYN PSLKSRVTIS GDTSKNQFSL KLNSVTAADT AVYYCVRGLY NWNVDSWGQG TLVTVSS |
| 17 | VASSLQS |
| 18 | LQHNSYPYT |
| 19 | DIQMTQSPSS LSASVGDRVT ITCRASQGIR NDLGWYQQKP GKAPKRLIYV ASSLQSGVPS RFSGSGSGTE FTLTISSLQP EDFATYYCLQ HNSYPYTFGQ GTKLEIK |

TABLE 3-continued

SEQ ID NO Sequences

| SEQ ID NO | SEQUENCES |
|---|---|
| 20 | GFTFSSYAMS |
| 21 | AISGGGGSTY YADSVKG |
| 22 | DIQWFGESTL FDY |
| 23 | EVQLLESGGG LVQPGGSLRL SCAASGFTFS SYAMSWVRQA PGKGLEWVSA ISGGGGSTYY ADSVKGRFTI SRDNSKNTLY LQMNSLRAED TAVYYCARDI QWFGESTLFD YWGQGTLVTV SS |
| 24 | RASQSIRSWL A |
| 25 | KASSLEG |
| 26 | QQYNSYSRT |
| 27 | DIQLTQSPST LSASVGDRVT ITCRASQSIR SWLAWFQQKP GKAPKLLIYK ASSLEGGVPS RFSGSGSGTE FTLTISSLQP DDFATYYCQQ YNSYSRTFGQ GTKVEIK |
| 28 | GFTFSDYYMT |
| 29 | FIRNRARGYT SDHNPSVKG |
| 30 | DRPSYYVLDY |
| 31 | EVQLVESGGG LVQPGGSLRL SCAASGFTFS DYYMTWVRQA PGKGLEWVAF IRNRARGYTS DHNPSVKGRF TISRDNAKNS LYLQMNSLRA EDTAVYYCAR DRPSYYVLDY WGQGTTVTVS S |
| 32 | KSSQSLFNVR SRKNYLA |
| 33 | WASTRES |
| 34 | KQSYDLFT |
| 35 | DIVMTQSPDS LAVSLGERAT INCKSSQSLF NVRSRKNYLA WYQQKPGQPP KLLISWASTR ESGVPDRFSG SGSGTDFTLT ISSLQAEDVA VYYCKQSYDL FTFGSGTKLE IK |
| 36 | GFTFSSYAMK |
| 37 | TTSGSGGTTY YADSVKG |
| 38 | AGWAAAFDY |
| 39 | EVQLLESGGG LVQPGGSLRL SCAASGFTFS SYAMKWVRQA PGKGLEWVST TSGSGGTTYY ADSVKGRFTI SRDNSKNTLY LQMNSLRAED TAVYYCAKAG WAAAFDYWGQ GTLVTVSS |
| 40 | RASQSISDWL A |
| 41 | KASSLES |
| 42 | QQCNSYWT |
| 43 | DIQLTQFPST LSASVGDRIT ITCRASQSIS DWLAWYQQKP GKAPKLLIYK ASSLESGVPS RFSGSGSGTE FTLTISSLQP DDFATYYCQQ CNSYWTFGQG TKVEIK |
| 44 | AISGSGGSTY YADSVKG |
| 45 | DIQWFGESVF DY |
| 46 | EVQLLESGGG LVQPGGSLRL SCAASGFTFS SYAMSWVRQA PGKGLEWVSA ISGGGGSTYY ADSVKGRFTI SRDNSKNTLF LHMNSLRAED TAVYYCARDI QWFGESVFDY WGQGTLVTVS S |
| 47 | RASQSISSWL A |
| 48 | QYYNSYSRT |

TABLE 3-continued

SEQ ID NO Sequences

| SEQ ID NO | SEQUENCES |
|---|---|
| 49 | DIQMTQSPST LSASVGDRVT ITCRASQSIS SWLAWYQQKP GKAPKLLIYK ASSLESGVPS RFSGNGSGTE FTLTISSLQP DDLATYYCQY YNSYSRTFGQ GTKVEIK |
| 50 | EINHSGSANY NPSLKS |
| 51 | GLYNWNVDR |
| 52 | QVQLQQWGAG LLKPSETLSL TCALYGGSFS GYYWNWIRQP PGKGLEWIGE INHSGSANYN PSLKSRVTIS VDTSKNQFSL RLSSVTAADT AVYYCARGLY NWNVDRWGQG TLVTVSS |
| 53 | LQHNSYPLT |
| 54 | DIQMTQSPSS LSASVGDRVT ITCRASQGIR NDLGWYQQKP GKAPKRLIYA ASSLQSGVPS RFSGSGSGTE FTLTISSLQP EDFATYYCLQ HNSYPLTFGG GTKVEIK |
| 55 | SISGNGGSTY YADSVKG |
| 56 | VGWRTGDY |
| 57 | EVQLLESGGG LVQPGGSLRL SCAASGFTFS SYAMSWVRQA PGKGLEWVSS ISGNGGSTYY ADSVKGRFTI SRDNSKNTLS LQMNSLRAED TAVYYCAKVG WRTGDYWGQG TLVTVSS |
| 58 | KASDLES |
| 59 | QQYNSYSWT |
| 60 | DIQLTQSPST LSASVGDRVT ITCRASQSIS SWLAWYQQKA GKAPKLLIYK ASDLESGVPS RFSGSGSGIE FTLTISSLQP DDFATYYCQQ YNSYSWTFGQ GTKVEIK |
| 61 | GGPFSGYFWS |
| 62 | EINHSGNTNY NPSLKS |
| 63 | AGGDYGFYYY YGMDV |
| 64 | QVQLQQWGAG LLKPSETLSL TCAVYGGPFS GYFWSWIRQP PGKGLEWIGE INHSGNTNYN PSLKSRVTIS VDTSKNQFSL KLSSVTAADT AVYYCARAGG DYGFYYYGM DVWGQGTTVT VSS |
| 65 | KASRLES |
| 66 | QQYNSY |
| 67 | DIQLTQSPST LSASVGDRVT ITCRASQSIS SWLAWYQQKP GKAPELLVYK ASRLESGVPS RFSGSGSGTE FTLTISSLQP DDFATYYCQQ YNSYFGGGTK VEIK |
| 68 | GLYNWNVDC |
| 69 | QVQLQQWGAG LLKPSETLSL TCAVYGGSFS GYYWNWIRQP PGKGLEWIGE INHSGSATYN PSLKSRVTIS VDTSKNHFSL KLNSVTAAGT AVYFCARGLY NWNVDCWGQG TLVTVSS |
| 70 | DIQMTQSPSS LSASVGDRVT ITCRASQGIR NDLGWYQQKP GKAPKRLIYA ASSLQSGVPS RFSGSGSGTE FSLTISSLQP EDFATYYCLQ HNSYPRTFGG GTKVEIK |
| 71 | GGSISSSSYY WG |
| 72 | TIYFSGNTYY NPSLKS |
| 73 | LRVTMVRGVI IGVFDY |
| 74 | QVQLQESGPG LVKPSETLSL TCTVSGGSIS SSSYYWGWIR QPPGKGLEWI GTIYFSGNTY YNPSLKSRVT ISVDTSKSQL SLKLNSVTAA DTAVYYCARL RVTMVRGVII GVFDYWGQGT LVTVSS |
| 75 | KSSQSVLYSS NNKNYLA |

TABLE 3-continued

SEQ ID NO Sequences

| SEQ ID NO | SEQUENCES |
|---|---|
| 76 | QQYYSTPPT |
| 77 | DIVMTQSPDS LAVSLGERAT INCKSSQSVL YSSNNKNYLA WYQQKPGQPP KLLIYWASTR ESGVPDRFSG SGSGTDFTLT ISSLQAEDVA VYYCQQYYST PPTFGQGTKV EIK |
| 78 | GFTFSTYAMN |
| 79 | VDVVARYYGM DV |
| 80 | EVQLLESGGG LVQPGGSLRL SCAASGFTFS TYAMNWVRQA PGKGLAWVSA ISGSGGSTYY ADSVKGRFTI SRDDSKNTLY LQMNSLRAED TAVYYCAKVD VVARYYGMDV WGQGTTVTVS S |
| 81 | RASQSISGWL A |
| 82 | EASSLES |
| 83 | QQYKSYSWT |
| 84 | DIQMTQSPST LSASVGDRVT ITCRASQSIS GWLAWYQQKP GKAPKLLIYE ASSLESGVPS RFSGSGSGTE FTLTISSLQP DDFATYYCQQ YKSYSWTFGQ GTKVEIK |
| 85 | AISGRGGSTY YTDSVKG |
| 86 | DLQWFGESTL FDY |
| 87 | EVQLLESGGG LVQPGGSLRL SCAASGFTFS SYAMSWVRQA PGKGLEWVSA ISGRGGSTYY TDSVKGRFTI SRDNSRNTLY LQMNILRAED TAVYYCARDL QWFGESTLFD YWGQGTLVTV SS |
| 88 | RASQSISAWL A |
| 89 | QQYNSYSRS |
| 90 | DIQLTQSPST LSASVGDRVT ITCRASQSIS AWLAWFQQKP GKAPKLLIYK ASSLESGVPS RFSGSGSGTE FTLTISSLQP DDFATYYCQQ YNSYSRSFGQ GTKLEIK |
| 91 | GFTFSSYALS |
| 92 | TINVGGVDTN YAGSVKG |
| 93 | ARITMVRGVI IPLFDY |
| 94 | EVQLLESGGG LVQPGGSLRL SCAASGFTFS SYALWVRQA PGKGLEWVST INVGGVDTNY AGSVKGRFTI SRDNPKNTLC LQMNSLRAED TAVYHCAKAR ITMVRGVIIP LFDYWGQGTL VTVAS |
| 95 | QQFYSTPVT |
| 96 | DIVMTQSPDS LAVSLGERAT INCKSSQSVL YSSNNKNYLA WYQQKPGQPP KLLIYWASTR ESGVPDRFSG SGSGTDFTLT ISSLQAEDVA VYYCQQFYST PVTFGGGTKV EIK |
| 97 | TGSISSSSYY WG |
| 98 | TIYFSGSTYY NPSLKS |
| 99 | LRVTMVRGVI IGVFDF |
| 100 | QVQLQESGPG LVKPSETLSL TCTVSTGSIS SSSYYWGWIR QPPGKGLEWI GTIYFSGSTY YNPSLKSRVT ISVDTSKNQF SLKLTSVTAA DTAVYYCARL RVTMVRGVII GVFDFWGQGT LVTVSS |
| 101 | GGSFSGYFWS |
| 102 | EFNHSGGTNS NPSLKS |
| 103 | AGGDYGFYYY YGLDV |
| 104 | QVQLQQWGAG LLKPSETLSL TCAVYGGSFS GYFWSWIRQP PGKGLEWIGE FNHSGGTNSN PSLKSRVTMS VDTSKNQFSL KLSSVTAADT AVYFCARAGG DYGFYYYGL DVWGQGTTVT VSS |

TABLE 3-continued

SEQ ID NO Sequences

| SEQ ID NO | SEQUENCES |
|---|---|
| 105 | FIRNQARGYT SDHNPSVKG |
| 106 | EVQLVESGGG LVQPGGSLRL SCAASGFTFS DYYMTWVRQA PGKGLEWVAF IRNQARGYTS DHNPSVKGRF TISRDNAKNS LYLQMNSLRA EDTAVYYCAR DRPSYYVLDY WGQGTTVTVS S |
| 107 | TSSQSLFNVR SQKNYLA |
| 108 | DIQMTQSPSS LSASVGDRVT ITCTSSQSLF NVRSQKNYLA WYQQKPGKAP KLLIYWASTR ESGVPSRFSG SGSGTDFTLT ISSLQPEDFA TYYCKQSYDL FTFGGGTKVE IK |
| 109 | FIRNQDRGYT SDHQPSVKG |
| 110 | EVQLVESGGG LVQPGGSLRL SCAASGFTFS DYYMTWVRQA PGKGLEWVAF IRNQDRGYTS DHQPSVKGRF TISRDNAKNS LYLQMNSLRA EDTAVYYCAR DRPSYYVLDY WGQGTTVTVS S |
| 111 | TSDQSLFNVR SGKNYLA |
| 112 | WASDRES |
| 113 | DIQMTQSPSS LSASVGDRVT ITCTSDQSLF NVRSGKNYLA WYQQKPGKAP KLLIYWASDR ESGVPSRFSG SGSGTDFTLT ISSLQPEDFA TYYCKQSYDL FTFGGGTKVE IK |
| 114 | DRHSYYVLDY |
| 115 | EVQLVESGGG LVQPGGSLRL SCAASGFTFS DYYMTWVRQA PGKGLEWVAF IRNQARGYTS DHNPSVKGRF TISRDNAKNS LYLQMNSLRA EDTAVYYCAR DRHSYYVLDY WGQGTTVTVS S |
| 116 | KQSYYLFT |
| 117 | DIQMTQSPSS LSASVGDRVT ITCTSSQSLF NVRSQKNYLA WYQQKPGKAP KLLIYWASTR ESGVPSRFSG SGSGTDFTLT ISSLQPEDFA TYYCKQSYYL FTFGGGTKVE IK |
| 118 | DIQMTQSPSS LSASVGDRVT ITCRASQSIR SWLAWYQQKP GKAPKLLIYK ASSLEGGVPS RFSGSGSGTD FTLTISSLQP EDFATYYCQQ YNSYSRTFGQ GTKVEIK |
| 119 | DIQMTQSPSS LSASVGDRVT ITCRASQGIR NDLGWYQQKP GKAPKLLIYV ASSLQSGVPS RFSGSGSGTD FTLTISSLQP EDFATYYCLQ HNSYPYTFGQ GTKLEIK |
| 120 | EVQLVESGGG LVQPGGSLRL SCAASGGSFS GYYWNWVRQA PGKGLEWIGE INHSGSTKYN PSLKSRFTIS GDNAKNSFYL QMNSLRAEDT AVYYCVRGLY NWNVDSWGQG TLVTVSS |
| 121 | RADAAPTVSI FPPSSEQLTS GGASVVCFLN NFYPKDINVK WKIDGSERQN GVLNSWTDQD SKDSTYSMSS TLTLTKDEYE RHNSYTCEAT HKTSTSPIVK SFNRNEC |
| 122 | DIQMTQSPSS LSASVGDRVT ITCRASQGIR NDLGWYQQKP GKAPKRLIYV ASSLQSGVPS RFSGSGSGTD FTLTISSLQP EDFATYYCLQ HNSYPYTFGQ GTKLEIK |
| 123 | DIQMTQSPSS LSASVGDRVT ITCRASQSIR SWLAWFQQKP GKAPKLLIYK ASSLEGGVPS RFSGSGSGTD FTLTISSLQP EDFATYYCQQ YNSYSRTFGQ GTKVEIK |
| 124 | EVQLVESGGG LVQPGGSLRL SCAASGGSFS GYYWNWVRQA PGKGLEWVAE INHSGSATYN PSLKSRFTIS RDNAKNSLYL QMNSLRAEDT AVYYCARGLY NWNVDHWGQG TLVTVSS |
| 125 | EVQLVESGGG LVQPGGSLRL SCAVSGGSFS GYYWNWVRQA PGKGLEWIGE INHSGSATYN PSLKSRFTIS VDTAKNSFYL QMNSLRAEDT AVYYCARGLY NWNVDHWGQG TLVTVSS |
| 126 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HNSYPRTFGG GTKVEIK |

TABLE 3-continued

SEQ ID NO Sequences

| SEQ ID NO | SEQUENCES |
|---|---|
| 127 | GGSFSGYYWS |
| 128 | EVQLVESGGG LVQPGGSLRL SCAVSGGSFS GYYWSWVRQP PGKGLEWIGE INHSGSATYN PSLKSRFTIS VDTAKNSFYL QMNSLRAEDT AVYYCARGLY NWNVDHWGQG TLVTVSS |
| 129 | EVQLVESGGG LVQPGGSLRL SCAVSGGSFS GYYWNWIRQP PGKGLEWIGE INHSGSATYN PSLKSRFTIS VDTAKNSFYL QMNSLRAEDT AVYYCARGLY NWNVDHWGQG TLVTVSS |
| 130 | EIDHQGSTKY NPSLKS |
| 131 | EVQLVESGGG LVQPGGSLRL SCAVSGGSFS GYYWNWVRQA PGKGLEWIGE IDHQGSTKYN PSLKSRFTIS VDTAKNSFYL QMNSLRAEDT AVYYCARGLY NWNVDHWGQG TLVTVSS |
| 132 | EVQLVESGGG LVQPGGSLRL SCAVSGGSFS GYYWNWVRQA PGKGLEWIGE INHSGSATYN PSLKSRVTIS VDTAKNSFYL QMNSLRAEDT AVYYCARGLY NWNVDHWGQG TLVTVSS |
| 133 | EVQLVESGGG LVQPGGSLRL SCAASGGSFS GYYWNWVRQA PGKGLEWVAE INHSGSATYN PSLKSRFTIS RDTAKNSLYL QMNSLRAEDT AVYYCARGLY NWNVDHWGQG TLVTVSS |
| 134 | EINHSGSATY VDSVKG |
| 135 | EVQLVESGGG LVQPGGSLRL SCAVSGGSFS GYYWNWVRQA PGKGLEWIGE INHSGSATYV DSVKGRFTIS RDTAKNSFYL QMNSLRAEDT AVYYCARGLY NWNVDHWGQG TLVTVSS |
| 136 | ELYNWNVDH |
| 137 | EVQLVESGGG LVQPGGSLRL SCAVSGGSFS GYYWNWVRQA PGKGLEWIGE INHSGSATYN PSLKSRFTIS VDTAKNSFYL QMNSLRAEDT AVYYCARELY NWNVDHWGQG TLVTVSS |
| 138 | LQHNAYPRT |
| 139 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HNAYPRTFGG GTKVEIK |
| 140 | LQHSSYPRT |
| 141 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HSSYPRTFGG GTKVEIK |
| 142 | LQHQSYPRT |
| 143 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HQSYPRTFGG GTKVEIK |
| 144 | LQHASYPRT |
| 145 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HASYPRTFGG GTKVEIK |
| 146 | LQHNAYPYT |
| 147 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HNAYPYTFGQ GTKLEIK |
| 148 | LQHQSYPYT |
| 149 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HQSYPYTFGQ GTKLEIK |
| 150 | LQHASYPYT |

TABLE 3-continued

SEQ ID NO Sequences

| SEQ ID NO | SEQUENCES |
|---|---|
| 151 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HASYPYTFGQ GTKLEIK |
| 152 | RASQSTRSWL A |
| 153 | QQYGSYSRT |
| 154 | DIQMTQSPSS LSASVGDRVT ITCRASQSTR SWLAWYQQKP GKAPKLLIYK ASSLEGGVPS RFSGSGSGTD FTLTISSLQP EDFATYYCQQ YGSYSRTFGQ GTKVEIK |
| 155 | EVQLVESGGG LVQPGGSLRL SCAASGGSFS GYYWNWIRQP PGKGLEWIGE IDHQGSTKYN PSLKSRVTIS VDTAKNSLYL QMNSLRAEDT AVYYCARGLY NWNVDHWGQG TLVTVSS |
| 156 | EVQLVESGGG LVQPGGSLRL SCAVSGGSFS GYYWNWIRQP PGKGLEWIGE IDHQGSTKYN PSLKSRVTIS VDTAKNSLYL QMNSLRAEDT AVYYCARELY NWNVDHWGQG TLVTVSS |
| 157 | EVQLVESGGG LVQPGGSLRL SCAASGGSFS GYYWNWIRQP PGKGLEWIGE IDHQGSTKYN PSLKSRVTIS VDTAKNSLYL QMNSLRAEDT AVYYCARELY NWNVDHWGQG TLVTVSS |
| 158 | AISGGGGSTQ YADSVKG |
| 159 | EVQLLESGGG LVQPGGSLRL SCAASGFTFS SYAMSWVRQA PGKGLEWVSA ISGGGGSTQY ADSVKGRFTI SRDNSKNTLY LQMNSLRAED TAVYYCARDI QWFGESTLFD YWGQGTLVTV SS |
| 160 | DIQWYGESTL FDY |
| 161 | EVQLLESGGG LVQPGGSLRL SCAASGFTFS SYAMSWVRQA PGKGLEWVSA ISGGGGSTYY ADSVKGRFTI SRDNSKNTLY LQMNSLRAED TAVYYCARDI QWYGESTLFD YWGQGTLVTV SS |
| 162 | DIQWHGESTL FDY |
| 163 | EVQLLESGGG LVQPGGSLRL SCAASGFTFS SYAMSWVRQA PGKGLEWVSA ISGGGGSTYY ADSVKGRFTI SRDNSKNTLY LQMNSLRAED TAVYYCARDI QWHGESTLFD YWGQGTLVTV SS |
| 164 | DIQWFGRSTL FDY |
| 165 | EVQLLESGGG LVQPGGSLRL SCAASGFTFS SYAMSWVRQA PGKGLEWVSA ISGGGGSTYY ADSVKGRFTI SRDNSKNTLY LQMNSLRAED TAVYYCARDI QWFGRSTLFD YWGQGTLVTV SS |
| 166 | RASQSTRSHL A |
| 167 | DIQMTQSPSS LSASVGDRVT ITCRASQSTR SHLAWYQQKP GKAPKLLIYK ASSLEGGVPS RFSGSGSGTD FTLTISSLQP EDFATYYCQQ YGSYSRTFGQ GTKVEIK |
| 168 | DIQMTQSPSS LSASVGDRVT ITCRASQSTR SWLAWYQQKP GKAPKLLIYK ASSLESGVPS RFSGSGSGTD FTLTISSLQP EDFATYYCQQ YGSYSRTFGQ GTKVEIK |
| 169 | DIQMTQSPSS LSASVGDRVT ITCRASQSTR SWLAWHQQKP GKAPKLLIYK ASSLESGVPS RFSGSGSGTD FTLTISSLQP EDFATYYCQQ YGSYSRTFGQ GTKVEIK |
| 170 | DIQMTQSPSS LSASVGDRVT ITCRASQSTR SWLAWLQQKP GKAPKLLIYK ASSLESGVPS RFSGSGSGTD FTLTISSLQP EDFATYYCQQ YGSYSRTFGQ GTKVEIK |
| 171 | EVQLVESGGG LVQPGGSLRL SCAVSGGSFS GYYWNWIRQP PGKGLEWIGE INHSGSATYN PSLKSRVTIS VDTAKNSLYL QMNSLRAEDT AVYYCARGLY NWNVDHWGQG TLVTVSS |
| 172 | EVQLVESGGG LVQPGGSLRL SCAVSGGSFS GYYWNWVRQA PGKGLEWIGE INHSGSATYN PSLKSRVTIS VDTAKNSLYL QMNSLRAEDT AVYYCARGLY NWNVDHWGQG TLVTVSS |

TABLE 3-continued

SEQ ID NO Sequences

| SEQ ID NO | SEQUENCES |
|---|---|
| 173 | EVQLVESGGG LVQPGGSLRL SCAVSGGSFS GYYWNWIRQP PGKGLEWIGE IDHQGSTKYN PSLKSRVTIS VDTAKNSFYL QMNSLRAEDT AVYYCARGLY NWNVDHWGQG TLVTVSS |
| 174 | EVQLVESGGG LVQPGGSLRL SCAASGGSFS GYYWNWVRQA PGKGLEWIGE INHSGSATYN PSLKSRVTIS VDTAKNSLYL QMNSLRAEDT AVYYCARGLY NWNVDHWGQG TLVTVSS |
| 175 | EVQLVESGGG LVQPGGSLRL SCAASGGSFS GYYWNWIRQP PGKGLEWIGE INHSGSATYN PSLKSRVTIS VDTAKNSFYL QMNSLRAEDT AVYYCARGLY NWNVDHWGQG TLVTVSS |
| 176 | EVQLVESGGG LVQPGGSLRL SCAASGGSFS GYYWNWIRQP PGKGLEWIGE INHSGSATYN PSLKSRVTIS VDTAKNSLYL QMNSLRAEDT AVYYCARGLY NWNVDHWGQG TLVTVSS |
| 177 | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCEVECPECP APPVAGPSVF LFPPKPKDTL MISRTPEVTC VVVAVSHEDP EVQFNWYVDG VEVHNAKTKP REEQFNSTFR VVSVLTVVHQ DWLNGKEYKC KVSNKGLPSS IEKTISKTKG QPREPQVYTL PPSREEMTKN QVSLTCEVKG FYPSDIAVEW ESNGQPENNY KTTPPMLDSD GSFFLYSKLT VDKSRWQQGN VFSCSVMHEA LHNHYTQKSL SLSPGK |
| 178 | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCRVRCPRCP APPVAGPSVF LFPPKPKDTL MISRTPEVTC VVVAVSHEDP EVQFNWYVDG VEVHNAKTKP REEQFNSTFR VVSVLTVVHQ DWLNGKEYKC KVSNKGLPSS IEKTISKTKG QPREPQVYTL PPSREEMTKN QVSLTCLVKG FYPSDIAVEW ESNGQPENNY KTTPPMLDSD GSFFLYSRLT VDKSRWQQGN VFSCSVMHEA LHNHYTQKSL SLSPGK |
| 179 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 180 | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCRVRCPRCP APPVAGPSVF LFPPKPKDTL MISRTPEVTC VVVAVSHEDP EVQFNWYVDG VEVHNAKTKP REEQFNSTFR VVSVLTVVHQ DWLNGKEYKC KVSNKGLPSS IEKTISKTKG QPREPQVYTL PPSREEMTKN QVSLTCLVKG FYPSDIAVEW ESNGQPENNY KTTPPMLDSD GSFFLYSRLT VDKSRWQQGN VFSCSVMHEA LHNHYTQKSL SLSPG |
| 181 | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCEVECPECP APPVAGPSVF LFPPKPKDTL MISRTPEVTC VVVAVSHEDP EVQFNWYVDG VEVHNAKTKP REEQFNSTFR VVSVLTVVHQ DWLNGKEYKC KVSNKGLPSS IEKTISKTKG QPREPQVYTL PPSREEMTKN QVSLTCEVKG FYPSDIAVEW ESNGQPENNY KTTPPMLDSD GSFFLYSKLT VDKSRWQQGN VFSCSVMHEA LHNHYTQKSL SLSPG |
| 182 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCRKTHTCP RCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SRLTVDKSRW QQGNVFSCSV MHEALHNHYT QKSLSLSPG |
| 183 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCEKTHTCP ECPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC EVKGFYPSDI AVEWESNGQP ENNYKTTPPV LDSDGSFFLY SKLTVDKSRW QQGNVFSCSV MHEALHNHYT QKSLSLSPG |
| 184 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS |

TABLE 3-continued

SEQ ID NO Sequences

| SEQ ID NO | SEQUENCES |
|---|---|
| | HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SRLTVDKSRW QQGNVFSCSV MHEALHNHYT QKSLSLSPG |
| 185 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC EVKGFYPSDI AVEWESNGQP ENNYKTTPPV LDSDGSFFLY SKLTVDKSRW QQGNVFSCSV MHEALHNHYT QKSLSLSPG |
| 186 | EVQLVESGGG LVQPGGSLRL SCAVSGGSFS GYYWNWVRQA PGKGLEWIGE INHSGSATYN PSLKSRVTIS VDTAKNSLYL QMNSLRAEDT AVYYCARGLY NWNVDHWGQG TLVTVSSAST KGPSVFPLAP CSRSTSESTA ALGCLVKDYF PEPVTVSWNS GALTSGVHTF PAVLQSSGLY SLSSVVTVPS SNFGTQTYTC NVDHKPSNTK VDKTVERKCE VECPECPAPP VAGPSVFLFP PKPKDTLMIS RTPEVTCVVV AVSHEDPEVQ FNWYVDGVEV HNAKTKPREE QFNSTFRVVS VLTVVHQDWL NGKEYKCKVS NKGLPSSIEK TISKTKGQPR EPQVYTLPPS REEMTKNQVS LTCEVKGFYP SDIAVEWESN GQPENNYKTT PPMLDSDGSF FLYSKLTVDK SRWQQGNVFS CSVMHEALHN HYTQKSLSLS PGK |
| 187 | DIQMTQSPSS LSASVGDRVT ITCRASQGIR NDLGWYQQKP GKAPKRLIYA ASSLQSGVPS RFSGSGSGTD FTLTISSLQP EDFATYYCLQ HNAYPRTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 188 | EVQLVESGGG LVQPGGSLRL SCAASGFTFS DYYMTWVRQA PGKGLEWVAF IRNQARGYTS DHNPSVKGRF TISRDNAKNS LYLQMNSLRA EDTAVYYCAR DRPSYYVLDY WGQGTTVTVS SASTKGPSVF PLAPCSRSTS ESTAALGCLV KDYFPEPVTV SWNSGALTSG VHTFPAVLQS SGLYSLSSVV TVPSSNFGTQ TYTCNVDHKP SNTKVDKTVE RKCRVRCPRC PAPPVAGPSV FLFPPKPKDT LMISRTPEVT CVVVAVSHED PEVQFNWYVD GVEVHNAKTK PREEQFNSTF RVVSVLTVVH QDWLNGKEYK CKVSNKGLPS SIEKTISKTK GQPREPQVYT LPPSREEMTK NQVSLTCLVK GFYPSDIAVE WESNGQPENN YKTTPPMLDS DGSFFLYSRL TVDKSRWQQG NVFSCSVMHE ALHNHYTQKS LSLSPGK |
| 189 | DIQMTQSPSS LSASVGDRVT ITCTSSQSLF NVRSQKNYLA WYQQKPGKAP KLLIYWASTR ESGVPSRFSG SGSGTDPFTLT ISSLQPEDFA TYYCKQSYDL FTFGGGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 190 | EVQLLESGGG LVQPGGSLRL SCAASGFTFS SYAMSWVRQA PGKGLEWVSA ISGGGGSTYY ADSVKGRFTI SRDNSKNTLY LQMNSLRAED TAVYYCARDI QWYGESTLFD YWGQGTLVTV SSASTKGPSV FPLAPCSRST SESTAALGCL VKDYFPEPVT VSWNSGALTS GVHTFPAVLQ SSGLYSLSSV VTVPSSNFGT QTYTCNVDHK PSNTKVDKTV ERKCEVECPE CPAPPVAGPS VFLFPPKPKD TLMISRTPEV TCVVVAVSHE DPEVQFNWYV DGVEVHNAKT KPREEQFNST FRVVSVLTVV HQDWLNGKEY KCKVSNKGLP SSIEKTISKT KGQPREPQVY TLPPSREEMT KNQVSLTCEV KGFYPSDIAV EWESNGQPEN NYKTTPPMLD SDGSFFLYSK LTVDKSRWQQ GNVFSCSVMH EALHNHYTQK SLSLSPGK |
| 191 | DIQMTQSPSS LSASVGDRVT ITCRASQSTR SHLAWYQQKP GKAPKLLIYK ASSLEGGVPS RFSGSGSGTD FTLTISSLQP EDFATYYCQQ YGSYSRTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 192 | GAGGTGCAGC TGGTGGAGTC TGGGGGAGGC TTGGTCCAGC CTGGGGGGTC CCTGAGACTC TCCTGTGCAG TGTCTGGAGG GTCCTTTAGT GGTTATTACT GGAACTGGGT GCGCCAGGCC CCAGGGAAGG GGCTGGAGTG GATTGGGGAA ATAAACCACT CCGGAAGCGC CACCTATAAC CCGTCTCTCA AGAGTCGAGT GACCATCTCC GTAGACACGG CCAAGAACTC ACTGTATCTG CAAATGAACA GCCTGAGAGC CGAGGACACG GCTGTGTATT ACTGTGCGAG AGGCCTTTAC AACTGGAACG TGGACCACTG GGGCCAGGGC ACCCTGGTCA CCGTCTCCTC AGCGTCGACC AAGGGCCCAT CGGTCTTCCC CCTGGCGCCC TGCTCCAGGA GCACCTCCGA GAGCACAGCG GCCCTGGGCT GCCTGGTCAA |

TABLE 3-continued

SEQ ID NO Sequences

| SEQ ID NO | SEQUENCES |
|---|---|
|  | GGACTACTTC CCCGAACCGG TGACGGTGTC GTGGAACTCA<br>GGCGCTCTGA CCAGCGGCGT GCACACCTTC CCGGCTGTCC<br>TACAGTCCTC AGGACTCTAC TCCCTCAGCA GCGTAGTGAC<br>CGTGCCCTCC AGCAACTTCG GCACCCAGAC CTACACCTGC<br>AACGTAGATC ACAAGCCCAG CAACACCAAG GTGGACAAGA<br>CAGTTGAGCG CAAATGTGAG GTCGAGTGCC CAGAGTGCCC<br>AGCACCACCT GTGGCAGGAC CGTCAGTCTT CCTCTTCCCC<br>CCAAAACCCA AGGACACCCT CATGATCTCC CGGACCCCTG<br>AGGTCACGTG CGTGGTGGTG GCCGTGAGCC ACGAAGACCC<br>CGAGGTCCAG TTCAACTGGT ACGTGGACGG CGTGGAGGTG<br>CATAATGCCA AGACAAAGCC ACGGGAGGAG CAGTTCAACA<br>GCACGTTCCG TGTGGTCAGC GTCCTCACCG TCGTGCACCA<br>GGACTGGCTG AACGGCAAGG AGTACAAGTG CAAGGTCTCC<br>AACAAAGGCC TCCCATCCTC CATCGAGAAA ACCATCTCCA<br>AAACCAAAGG GCAGCCCCGA GAACCACAGG TGTACACCCT<br>GCCCCCATCC CGGGAGGAGA TGACCAAGAA CCAGGTCAGC<br>CTGACCTGCG AGGTCAAAGG CTTCTACCCC AGCGACATCG<br>CCGTGGAGTG GGAGAGCAAT GGGCAGCCGG AGAACAACTA<br>CAAGACCACA CCTCCCATGC TGGACTCCGA CGGCTCCTTC<br>TTCCTCTACA GCAAGCTCAC CGTGGACAAG AGCAGGTGGC<br>AGCAGGGGAA CGTCTTCTCA TGCTCCGTGA TGCATGAGGC<br>TCTGCACAAC CACTACACAC AGAAGAGCCT CTCCCTGTCC CCCGGAAAA |
| 193 | GACATCCAGA TGACCCAGTC TCCATCCTCC CTGTCTGCAT<br>CTGTAGGAGA CAGAGTCACC ATCACTTGCC GGGCAAGTCA<br>GGGCATTAGA AATGATTTAG GCTGGTATCA GCAGAAACCA<br>GGGAAAGCCC CTAAGCGCCT GATCTATGCT GCATCCAGTT<br>TGCAAAGTGG GGTCCCATCA AGGTTCAGTG GCAGTGGATC<br>TGGGACAGAT TTCACTCTCA CCATCAGCAG TCTGCAACCT GAAGATTTTG<br>CAACTTACTA CTGTCTACAG CATAATGCCT ACCCTCGCAC<br>TTTCGGCGGA GGGACCAAGG TGGAGATCAA ACGTACGGTG<br>GCTGCACCAT CTGTCTTCAT CTTCCCGCCA TCTGATGAGC AGTTGAAATC<br>TGGAACTGCC TCTGTTGTGT GCCTGCTGAA TAACTTCTAT<br>CCCAGAGAGG CCAAAGTACA GTGGAAGGTG GATAACGCCC<br>TCCAATCGGG TAACTCCCAG GAGAGTGTCA CAGAGCAGGA<br>CAGCAAGGAC AGCACCTACA GCCTCAGCAG CACCCTGACG<br>CTGAGCAAAG CAGACTACGA GAAACACAAA GTCTACGCCT<br>GCGAAGTCAC CCATCAGGGC CTGAGCTCGC CCGTCACAAA<br>GAGCTTCAAC AGGGGAGAGT GT |
| 194 | GAAGTGCAGC TTGTGGAGTC CGGTGGCGGA CTCGTGCAGC<br>CGGGCGGATC CCTGAGACTG TCGTGTGCCG CATCAGGATT<br>CACCTTTTCC GACTATTACA TGACCTGGGT CCGCCAAGCT<br>CCCGGGAAGG GCCTGGAATG GGTGGCCTTC ATCCGCAACC<br>AGGCCCGGGG CTACACTTCC GATCACAACC CTAGCGTGAA<br>GGGAAGGTTC ACCATTTCGC GGGACAACGC GAAGAATTCC<br>CTGTACCTCC AAATGAACAG CCTGCGGGCC GAGGACACTG<br>CCGTCTACTA CTGCGCCCGC GATAGACCAA GCTACTACGT<br>GTTGGACTAC TGGGGACAGG GGACCACGGT CACCGTCTCC<br>TCAGCCTCCA CCAAGGGCCC ATCGGTCTTC CCCCTGGCGC<br>CCTGCTCCAG GAGCACCTCC GAGAGCACAG CGGCCCTGGG<br>CTGCCTGGTC AAGGACTACT TCCCCGAACC GGTGACGGTG<br>TCGTGGAACT CAGGCGCTCT GACCAGCGGC GTGCACACCT<br>TCCCGGCTGT CCTACAGTCC TCAGGACTCT ACTCCCTCAG<br>CAGCGTAGTG ACCGTGCCCT CCAGCAACTT CGGCACCCAG<br>ACCTACACCT GCAACGTAGA TCACAAGCCC AGCAACACCA<br>AGGTGGACAA GACAGTTGAG CGCAAATGTC GTGTCAGGTG<br>CCCAAGGTGC CCAGCACCAC CTGTGGCAGG ACCGTCAGTC<br>TTCCTCTTCC CCCCAAAACC CAAGGACACC CTCATGATCT<br>CCCGGACCCC TGAGGTCACG TGCGTGGTGG TGGCCGTGAG<br>CCACGAAGAC CCCGAGGTCC AGTTCAACTG GTACGTGGAC<br>GGCGTGGAGG TGCATAATGC CAAGACAAAG CCACGGGAGG<br>AGCAGTTCAA CAGCACGTTC CGTGTGGTCA GCGTCCTCAC<br>CGTCGTGCAC CAGGACTGGC TGAACGGCAA GGAGTACAAG<br>TGCAAGGTCT CCAACAAAGG CCTCCCATCC TCCATCGAGA<br>AAACCATCTC CAAAACCAAA GGGCAGCCCC GAGAACCACA<br>GGTGTACACC CTGCCCCCAT CCCGGGAGGA GATGACCAAG<br>AACCAGGTCA GCCTGACCTG CCTGGTCAAA GGCTTCTACC<br>CCAGCGACAT CGCCGTGGAG TGGGAGAGCA ATGGGCAGCC<br>GGAGAACAAC TACAAGACCA CACCTCCCAT GCTGGACTCC<br>GACGGCTCCT TCTTCCTCTA CAGCAGGCTC ACCGTGGACA<br>AGAGCAGGTG GCAGCAGGGG AACGTCTTCT CATGCTCCGT<br>GATGCATGAG GCTCTGCACA ACCACTACAC ACAGAAGAGC<br>CTCTCCCTGT CTCCGGGTAA A |

TABLE 3-continued

| SEQ ID NO | SEQUENCES |
|---|---|
| 195 | GACATCCAAA TGACCCAGTC ACCGTCATCG CTCTCGGCTT CCGTGGGCGA TAGAGTGACC ATTACTTGCA CGAGCTCCCA GTCCCTGTTC AACGTGCGCA GCCAGAAGAA CTACCTCGCC TGGTACCAGC AGAAGCCTGG AAAAGCCCCG AAGCTTCTGA TCTACTGGGC CTCGACCCGG GAGTCTGGTG TCCCATCCCG GTTCTCCGGA TCCGGCTCCG GGACCGACTT CACTCTGACC ATTAGCAGCC TGCAGCCCGA AGATTTCGCG ACCTATTACT GCAAGCAATC CTACGACTTG TTCACTTTTG GCGGGGGAAC CAAGGTCGAG ATCAAACGAA CTGTGGCTGC ACCATCTGTC TTCATCTTCC CGCCATCTGA TGAGCAGTTG AAATCTGGAA CTGCCTCTGT TGTGTGCCTG CTGAATAACT TCTATCCCAG AGAGGCCAAA GTACAGTGGA AGGTGGATAA CGCCCTCCAA TCGGGTAACT CCCAGGAGAG TGTCACAGAG CAGGACAGCA AGGACAGCAC CTACAGCCTC AGCAGCACCC TGACGCTGAG CAAAGCAGAC TACGAGAAAC ACAAAGTCTA CGCCTGCGAA GTCACCCATC AGGGCCTGAG CTCGCCCGTC ACAAAGAGCT TCAACAGGGG AGAGTGT |
| 196 | GAGGTGCAGC TGTTGGAGTC TGGGGGAGGC TTGGTACAGC CTGGGGGGTC CCTGAGACTC TCCTGTGCAG CCTCTGGATT CACCTTTAGC AGCTATGCCA TGAGCTGGGT CCGCCAGGCT CCAGGGAAGG GGCTGGAATG GGTCTCAGCT ATTAGTGGTG GTGGTGGTAG CACATACTAC GCAGACTCCG TGAAGGGCCG GTTCACCATC TCCAGAGACA ATTCCAAGAA CACGCTGTAT CTGCAAATGA ACAGCCTGAG AGCCGAGGAC ACGGCCGTAT ATTACTGTGC GAGGGACATA CAGTGGTACG GGGAGTCAAC CCTCTTTGAC TACTGGGGCC AGGGAACCCT GGTCACCGTC TCCTCAGCGT CGACCAAGGG CCCATCGGTC TTCCCCCTGG CGCCCTGCTC CAGGAGCACC TCCGAGAGCA CAGCGGCCCT GGGCTGCCTG GTCAAGGACT ACTTCCCCGA ACCGGTGACG GTGTCGTGGA ACTCAGGCGC TCTGACCAGC GGCGTGCACA CCTTCCCGGC TGTCCTACAG TCCTCAGGAC TCTACTCCCT CAGCAGCGTA GTGACCGTGC CCTCCAGCAA CTTCGGCACC CAGACCTACA CCTGCAACGT AGATCACAAG CCCAGCAACA CCAAGGTGGA CAAGACAGTT GAGCGCAAAT GTGAGGTCGA GTGCCCAGAG TGCCCAGCAC CACCTGTGGC AGGACCGTCA GTCTTCCTCT TCCCCCCAAA ACCCAAGGAC ACCCTCATGA TCTCCCGGAC CCCTGAGGTC ACGTGCGTGG TGGTGGCCGT GAGCCACGAA GACCCCGAGG TCCAGTTCAA CTGGTACGTG GACGGCGTGG AGGTGCATAA TGCCAAGACA AAGCCACGGG AGGAGCAGTT CAACAGCACG TTCCGTGTGG TCAGCGTCCT CACCGTCGTG CACCAGGACT GGCTGAACGG CAAGGAGTAC AAGTGCAAGG TCTCCAACAA AGGCCTCCCA TCCTCCATCG AGAAAACCAT CTCCAAAACC AAAGGGCAGC CCCGAGAACC ACAGGTGTAC ACCCTGCCCC CATCCCGGGA GGAGATGACC AAGAACCAGG TCAGCCTGAC CTGCGAGGTC AAAGGCTTCT ACCCCAGCGA CATCGCCGTG GAGTGGGAGA GCAATGGGCA GCCGGAGAAC AACTACAAGA CCACACCTCC CATGCTGGAC TCCGACGGCT CCTTCTTCCT CTACAGCAAG CTCACCGTGG ACAAGAGCAG GTGGCAGCAG GGGAACGTCT TCTCATGCTC CGTGATGCAT GAGGCTCTGC ACAACCACTA CACACAGAAG AGCCTCTCCC TGTCCCCCGG AAAA |
| 197 | GACATCCAGA TGACCCAGTC TCCATCCTCC CTGTCTGCAT CTGTAGGAGA CAGAGTCACC ATCACTTGCC GGGCAAGTCA GAGCACCCGT AGCCACTTAG CCTGGTATCA GCAGAAACCA GGGAAAGCCC CTAAGCTCCT GATCTATAAG GCATCCAGTT TGGAAGGTGG GGTCCCATCA AGGTTCAGTG GCAGTGGATC TGGGACAGAT TTCACTCTCA CCATCAGCAG TCTGCAACCT GAAGATTTTG CAACTTACTA CTGTCAACAG TATGGCAGTT ATTCTCGGAC GTTCGGCCAA GGGACCAAGG TGGAAATCAA ACGTACGGTG GCTGCACCAT CTGTCTTCAT CTTCCCGCCA TCTGATGAGC AGTTGAAATC TGGAACTGCC TCTGTTGTGT GCCTGCTGAA TAACTTCTAT CCCAGAGAGG CCAAAGTACA GTGGAAGGTG GATAACGCCC TCCAATCGGG TAACTCCCAG GAGAGTGTCA CAGAGCAGGA CAGCAAGGAC AGCACCTACA GCCTCAGCAG CACCCTGACG CTGAGCAAAG CAGACTACGA GAAACACAAA GTCTACGCCT GCGAAGTCAC CCATCAGGGC CTGAGCTCGC CCGTCACAAA GAGCTTCAAC AGGGGAGAGT GT |
| 198 | GGGGSGGGGSGGGGS |
| 199 | GYYWN |
| 200 | GGSFS GY |

TABLE 3-continued

SEQ ID NO Sequences

| SEQ ID NO | SEQUENCES |
|---|---|
| 201 | NHSGS |
| 202 | DYYMT |
| 203 | GFTFS DY |
| 204 | RNQARGYT |
| 205 | SYAMS |
| 206 | GFTFS SY |
| 207 | SGGGGS |
| 208 | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP APPVAGPSVF LFPPKPKDTL MISRTPEVTC VVVDVSHEDP EVQFNWYVDG VEVHNAKTKP REEQFNSTFR VVSVLTVVHQ DWLNGKEYKC KVSNKGLPAP IEKTISKTKG QPREPQVYTL PPSREEMTKN QVSLTCLVKG FYPSDIAVEW ESNGQPENNY KTTPPMLDSD GSFFLYSKLT VDKSRWQQGN VFSCSVMHEA LHNHYTQKSL SLSPGK |
| 209 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCP APELLG GPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 210 | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCSCP APEFLG GPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLTCLVKG FYPSDIAVEW ESNGQPENNY KTTPPVLDSD GSFFLYSRLT VDKSRWQEGN VFSCSVMHEA LHNHYTQKSL SLSLGK |

In some embodiments, the invention also provides CDR portions of the B7-H4 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the B7-H4 antibody as described herein to B7-H4, such as the extracellular domain of the hB7-H4, can be about 0.002 nM to about 6500 nM. In some embodiments, the binding affinity is about any of 6500 nm, 6000 nm, 5986 nm, 5567 nm, 5500 nm, 4500 nm, 4000 nm, 3500 nm, 3000 nm, 2500 nm, 2134 nm, 2000 nm, 1500 nm, 1000 nm, 750 nm, 500 nm, 400 nm, 300 nm, 250 nm, 200 nM, 193 nM, 100 nM, 90 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.002 nM. In some embodiments, the binding affinity is less than about any of about 6500 nm, 6000 nm, 5500 nm, 5000 nm, 4000 nm, 3000 nm, 2000 nm, 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM 1 nM or 0.5 nM.

In some embodiments, the B7-H4 antibody of the present invention is a full-length human antibody.

In some embodiments, the B7-H4 antibody of the present invention is a single chain variable region antibody (scFv).

In some embodiments, the B7-H4 antibody of the present invention is a diabody or a minibody.

In some embodiments, the B7-H4 antibody of the present invention is a fusion protein comprising an antigen binding portion that binds to B7-H4, wherein the antigen binding portion comprising a VH CDR1, a VH CDR2, a VH CDR3, a VL CDR1, a VL CDR2 and a VL CDR3, wherein the six CDRs each having the same amino acid sequence as the corresponding CDR of an antibody described in Table 2.

In some embodiments, the invention provides a chimeric antigen receptor (CAR) comprising an extracellular domain that specifically binds B7-H4, a first transmembrane domain, and an intracellular signaling domain. In some embodiments the extracellular domain comprises a single chain Fv fragment (ScFv) comprising a VH CDR1, a VH CDR2, a VH CDR3, a VL CDR1, a VL CDR2 and a VL CDR3, wherein the six CDRs each having the same amino acid sequence as the corresponding CDR of an antibody described in Table 2.

The invention also provides methods of making any of the antibodies disclosed herein. The antibodies provided herein may be made by procedures known in the art.

B7-H4 Antibody Conjugates

The present invention also provides a conjugate (or immunoconjugate) of the B7-H4 antibody as described herein, or of the antigen binding fragment thereof, wherein the antibody or the antigen binding fragment is conjugated to an agent (e.g., a cytotoxic agent) for targeted immunotherapy (e.g., antibody-drug conjugates) either directly or indirectly via a linker. For example, a cytotoxic agent can be linked or conjugated to the B7-H4 antibody or the antigen binding fragment thereof as described herein for targeted local delivery of the cytotoxic agent moiety to tumors (e.g., B7-H4 expressing tumor).

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in international applications WO2012/059882 and WO2015015448.

The agents that can be conjugated to the B7-H4 antibody or the antigen binding fragment of the present invention include, but are not limited to, cytotoxic agents, immunomodulating agents, imaging agents, therapeutic proteins, biopolymers, or oligonucleotides.

Examples of a cytotoxic agent that can be conjugated to the B7-H4 antibody or an antigen binding fragment thereof include, but are not limited to, anthracycline, an auristatin, a dolastatin, a combretastatin, a duocarmycin, a pyrrolobenzodiazepine dimer, an indolino-benzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof.

Examples of an immunomodulating agent that can be conjugated to the B7-H4 antibody or an antigen binding fragment thereof include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

Examples of an imaging agent (e.g., a fluorophore or a chelator) that can be conjugated to the B7-H4 antibody or an antigen binding fragment thereof, such as fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N,N', N'',N'''-tetraacetic acid (DOTA), 1,4,7-triazacyclononane-1, 4,7-triacetic acid (NOTA), 1,4,7-triazacyclononane,1-glutaric acid-4,7-acetic acid (deferoxamine), diethylenetriaminepentaacetic acid (DTPA), and 1,2-bis(o-aminophenoxy)ethane-N,N,N',N'-tetraacetic acid) (BAPTA).

In some embodiments, the agent is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *Momordica charantia* inhibitor, curcin, crotin, *Sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, the agent is a biocompatible polymer. The B7-H4 antibodies or the antigen binding fragments as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the agent is an oligonucleotide, such as anti-sense oligonucleotides.

CD3 Antibodies

The present invention further provides an antibody that binds to CD3 (e.g., human CD3.)

In some embodiments, the invention provides an isolated antibody, which specifically binds to CD3, wherein the antibody comprises:

a) a VH having the amino acid sequence of SEQ ID NO: 31, a VL having the amino acid sequence of SEQ ID NO: 35, a heavy chain constant region (CH) of amino acid sequence of SEQ ID NO: 178 and a light chain constant region (CL) of amino acid sequence of SEQ ID NO: 12;

b) a VH having the amino acid sequence of SEQ ID NO: 110, a VL having the amino acid sequence of SEQ ID NO: 113, a CH of amino acid sequence of SEQ ID NO: 180 and a CL of amino acid sequence of SEQ ID NO: 12;

c) a VH having the amino acid sequence of SEQ ID NO: 115, a VL having the amino acid sequence of SEQ ID NO: 117, a CH of amino acid sequence of SEQ ID NO: 180 and a CL of amino acid sequence of SEQ ID NO: 12;

d) a VH having the amino acid sequence of SEQ ID NO: 106, a VL having the amino acid sequence of SEQ ID NO: 108, a CH of amino acid sequence of SEQ ID NO: 182 and a CL of amino acid sequence of SEQ ID NO: 12;

e) a VH having the amino acid sequence of SEQ ID NO: 106, a VL having the amino acid sequence of SEQ ID NO: 108, a CH of amino acid sequence of SEQ ID NO: 184 and a CL of amino acid sequence of SEQ ID NO: 12; or f) a VH having the amino acid sequence of SEQ ID NO: 106, a VL having the amino acid sequence of SEQ ID NO: 108, a CH of amino acid sequence of SEQ ID NO: 178 and a CL of amino acid sequence of SEQ ID NO: 12.

In another embodiment, the invention provides an antibody that specifically binds to CD3, wherein the antibody comprises a VH CDR1, a VH CDR2, a VH CDR3, a VL CDR1, a VL CDR2, and a VLCDR3, each having the same amino acid sequence as that of the corresponding CDR of any one of the antibodies listed in Table 4.

In another embodiment, the invention provides an antibody that specifically binds to CD3, wherein the antibody comprises a VH and a VH each having the same amino acid sequence as that of the VH and VL of any one of the antibodies listed in Table 4.

Table 4 describes exemplary CD3 antibodies of the present invention.

TABLE 4

Exemplary CD3 Antibodies

| Antibody name | SEQ ID NO: of the indicated antibody portion | | | | | | | | | |
|---|---|---|---|---|---|---|---|---|---|---|
| | VH CDR1 | VH CDR2 | VH CDR3 | VL CDR1 | VL CDR2 | VL CDR3 | CH | CL | VH | VL |
| 2B4 IgG2 | 28 | 29 | 30 | 32 | 33 | 34 | 178 | 12 | 31 | 35 |
| 2B5v598 IgG2 | 28 | 109 | 30 | 111 | 112 | 34 | 180 | 12 | 110 | 113 |
| 2B5c707 IgG2 | 28 | 105 | 114 | 107 | 33 | 116 | 180 | 12 | 115 | 117 |
| 2B5v6 IgG1 | 28 | 105 | 30 | 107 | 33 | 34 | 182 | 12 | 106 | 108 |
| 2B5V6 IgG1 #2 | 28 | 105 | 30 | 107 | 33 | 34 | 184 | 12 | 106 | 108 |
| 2B5V6 IgG2 | 28 | 105 | 30 | 107 | 33 | 34 | 178 | 12 | 106 | 108 |

B7-H4 Bispecific Antibodies

The present invention also provides a bispecific antibody that specifically binds to B7-H4 and a second antigen.

The Second Antigen

In some embodiments, the second antigen is an effector antigen located on a human immune effector cell. The concept of effector antigen on a human effector cell is well known in the art. Exemplary effector antigens include, but are not limited to CD3, CD16, NKG2D, NKp-46, CD2, CD28, CD25, CD64, and CD89.

In some embodiments, the second antigen is CD3.

In some embodiments, the second antigen can be a target antigen (other than B7-H4) on a target cell, wherein the target cell can be a cell that is native or foreign to humans. In a native target cell, the cell may have been transformed to be a malignant cell or pathologically modified (e.g., a native target cell infected with a virus, a *plasmodium*, or a bacterium). In a foreign target cell, the cell is an invading pathogen, such as a bacterium, a *plasmodium*, or a virus.

The target antigen is expressed on a target cell in a diseased condition (e.g., an inflammatory disease, a proliferative disease (e.g., cancer), an immunological disorder, a neurological disease, a neurodegenerative disease, an autoimmune disease, an infectious disease (e.g., a viral infection or a parasitic infection), an allergic reaction, a graft-versus-host disease or a host-versus-graft disease). A target antigen is not an effector antigen. Examples of the target antigens include, but are not limited to, B7-H4, EpCAM (Epithelial Cell Adhesion Molecule), CCR5 (Chemokine Receptor type 5), CD19, HER (Human Epidermal Growth Factor Receptor)-2/neu, HER-3, HER-4, EGFR (Epidermal Growth Factor Receptor), PSMA, CEA, MUC-1 (Mucin), MUC2, MUC3, MUC4, MUC5AC, MUC5B, MUC7, ClhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Shh (Sonic Hedgehog), Wue-1, Plasma Cell Antigen, (membrane-bound) IgE, MCSP (Melanoma Chondroitin Sulfate Proteoglycan), CCR8, TNF-alpha precursor, STEAP, mesothelin, A33 Antigen, PSCA (Prostate Stem Cell Antigen), Ly-6; desmoglein 4, E-cadherin neoepitope, Fetal Acetylcholine Receptor, CD25, CA19-9 marker, CA-125 marker and MIS (Muellerian Inhibitory Substance) Receptor type II, sTn (sialylated Tn antigen; TAG-72), FAP (fibroblast activation antigen), endosialin, EGFRvIII, LG, SAS and CD63.

B7-H4×CD3 Bispecific Antibodies

Table 5 below provides the SEQ ID NOs of the CDRs, constant region and variable region of both the first arm and the second arm of the exemplary bispecific antibodies of this invention that that specifically binds to both B7-H4 and CD3 ("B7-H4×CD3 bispecific antibodies").

TABLE 5

Exemplary B7-H4xCD3 Bispecific Antibodies

| Antibody Name | SEQ ID NO: of the indicated antibody portion | | | | | | | | | |
|---|---|---|---|---|---|---|---|---|---|---|
| | CDR1 (VH) | CDR2 (VH) | CDR3 (VH) | CDR1 (VL) | CDR2 (VL) | CDR3 (VL) | CH | CL | VH | VL |
| 0032 (1st arm) | 20 | 21 | 22 | 24 | 25 | 26 | 177 | 12 | 23 | 27 |
| 0032 (2nd arm) | 28 | 29 | 30 | 32 | 33 | 34 | 178 | 12 | 31 | 35 |
| 0038 (1st arm) | 5 | 14 | 15 | 9 | 17 | 18 | 177 | 12 | 16 | 19 |
| 0038 (2nd arm) | 28 | 29 | 30 | 32 | 33 | 34 | 178 | 12 | 31 | 35 |
| 0044 (1st arm) | 5 | 6 | 7 | 9 | 10 | 11 | 177 | 12 | 8 | 13 |

TABLE 5-continued

Exemplary B7-H4xCD3 Bispecific Antibodies

SEQ ID NO: of the indicated antibody portion

| Antibody Name | CDR1 (VH) | CDR2 (VH) | CDR3 (VH) | CDR1 (VL) | CDR2 (VL) | CDR3 (VL) | CH | CL | VH | VL |
|---|---|---|---|---|---|---|---|---|---|---|
| 0044 (2nd arm) | 28 | 29 | 30 | 32 | 33 | 34 | 178 | 12 | 31 | 35 |
| 0068 (1st arm) | 20 | 21 | 22 | 24 | 25 | 26 | 177 | 12 | 23 | 27 |
| 0068 (2nd arm) | 28 | 105 | 30 | 107 | 33 | 34 | 178 | 12 | 106 | 108 |
| 0074 (1st arm) | 5 | 14 | 15 | 9 | 17 | 18 | 177 | 12 | 16 | 19 |
| 0074 (2nd arm) | 28 | 105 | 30 | 107 | 33 | 34 | 178 | 12 | 106 | 108 |
| 0077 (1st arm) | 5 | 50 | 51 | 9 | 10 | 53 | 177 | 12 | 52 | 54 |
| 0077 (2nd arm) | 28 | 105 | 30 | 107 | 33 | 34 | 178 | 12 | 106 | 108 |
| 0080 (1st arm) | 5 | 6 | 7 | 9 | 10 | 11 | 177 | 12 | 8 | 13 |
| 0080 (2nd arm) | 28 | 105 | 30 | 107 | 33 | 34 | 178 | 12 | 106 | 108 |
| 0087 (1st arm) | 5 | 14 | 15 | 9 | 17 | 18 | 181 | 12 | 16 | 19 |
| 0087 (2nd arm) | 28 | 109 | 30 | 111 | 112 | 34 | 180 | 12 | 110 | 113 |
| 0088 (1st arm) | 5 | 14 | 15 | 9 | 17 | 18 | 181 | 12 | 16 | 19 |
| 0088 (2nd arm) | 28 | 105 | 114 | 107 | 33 | 116 | 180 | 12 | 115 | 117 |
| 0089 (1st arm) | 5 | 14 | 15 | 9 | 17 | 18 | 183 | 12 | 16 | 19 |
| 0089 (2nd arm) | 28 | 105 | 30 | 107 | 33 | 34 | 182 | 12 | 106 | 108 |
| 0090 (1st arm) | 5 | 14 | 15 | 9 | 17 | 18 | 185 | 12 | 16 | 19 |
| 0090 (2nd arm) | 28 | 105 | 30 | 107 | 33 | 34 | 184 | 12 | 106 | 108 |
| 0974 (1st arm) | 5 | 130 | 7 | 9 | 10 | 138 | 181 | 12 | 155 | 139 |
| 0974 (2nd arm) | 28 | 105 | 30 | 107 | 33 | 34 | 178 | 12 | 106 | 108 |
| 0976 (1st arm) | 5 | 130 | 136 | 9 | 10 | 138 | 181 | 12 | 156 | 139 |
| 0976 (2nd arm) | 28 | 105 | 30 | 107 | 33 | 34 | 178 | 12 | 106 | 108 |
| 0978 (1st arm) | 5 | 130 | 136 | 9 | 10 | 140 | 181 | 12 | 157 | 141 |
| 0978 (2nd arm) | 28 | 105 | 30 | 107 | 33 | 34 | 178 | 12 | 106 | 108 |
| 0980 (1st arm) | 5 | 130 | 7 | 9 | 10 | 140 | 181 | 12 | 155 | 141 |
| 0980 (2nd arm) | 28 | 105 | 30 | 107 | 33 | 34 | 178 | 12 | 106 | 108 |
| 0982 (1st arm) | 5 | 130 | 136 | 9 | 10 | 140 | 181 | 12 | 156 | 141 |
| 0982 (2nd arm) | 28 | 105 | 30 | 107 | 33 | 34 | 178 | 12 | 106 | 108 |
| 0998 (1st arm) | 20 | 158 | 22 | 24 | 25 | 26 | 181 | 12 | 159 | 27 |
| 0998 (2nd arm) | 28 | 105 | 30 | 107 | 33 | 34 | 178 | 12 | 106 | 108 |
| 0999 (1st arm) | 20 | 21 | 160 | 24 | 25 | 26 | 181 | 12 | 161 | 27 |
| 0999 (2nd arm) | 28 | 105 | 30 | 107 | 33 | 34 | 178 | 12 | 106 | 108 |
| 1000 (1st arm) | 20 | 21 | 162 | 24 | 25 | 26 | 181 | 12 | 163 | 27 |
| 1000 (2nd arm) | 28 | 105 | 30 | 107 | 33 | 34 | 178 | 12 | 106 | 108 |
| 1001 (1st arm) | 20 | 21 | 164 | 24 | 25 | 26 | 181 | 12 | 165 | 27 |
| 1001 (2nd arm) | 28 | 105 | 30 | 107 | 33 | 34 | 178 | 12 | 106 | 108 |
| 1003 (1st arm) | 20 | 21 | 22 | 166 | 25 | 153 | 181 | 12 | 23 | 167 |

TABLE 5-continued

Exemplary B7-H4xCD3 Bispecific Antibodies

SEQ ID NO: of the indicated antibody portion

| Antibody Name | CDR1 (VH) | CDR2 (VH) | CDR3 (VH) | CDR1 (VL) | CDR2 (VL) | CDR3 (VL) | CH | CL | VH | VL |
|---|---|---|---|---|---|---|---|---|---|---|
| 1003 (2nd arm) | 28 | 105 | 30 | 107 | 33 | 34 | 178 | 12 | 106 | 108 |
| 1014 (1st arm) | 5 | 6 | 7 | 9 | 10 | 140 | 181 | 12 | 171 | 141 |
| 1014 (2nd arm) | 28 | 105 | 30 | 107 | 33 | 34 | 178 | 12 | 106 | 108 |
| 1037 (1st arm) | 5 | 6 | 7 | 9 | 10 | 140 | 181 | 12 | 172 | 141 |
| 1037 (2nd arm) | 28 | 105 | 30 | 107 | 33 | 34 | 178 | 12 | 106 | 108 |
| 1130 (1st arm) | 5 | 6 | 7 | 9 | 10 | 138 | 181 | 12 | 176 | 139 |
| 1130 (2nd arm) | 28 | 105 | 30 | 107 | 33 | 34 | 178 | 12 | 106 | 108 |
| 1133 (1st arm) | 5 | 6 | 7 | 9 | 10 | 138 | 181 | 12 | 171 | 139 |
| 1133 (2nd arm) | 28 | 105 | 30 | 107 | 33 | 34 | 178 | 12 | 106 | 108 |
| 1134 (1st arm) | 5 | 130 | 7 | 9 | 10 | 138 | 181 | 12 | 173 | 139 |
| 1134 (2nd arm) | 28 | 105 | 30 | 107 | 33 | 34 | 178 | 12 | 106 | 108 |
| 1135 (1st arm) | 5 | 6 | 7 | 9 | 10 | 138 | 181 | 12 | 174 | 139 |
| 1135 (2nd arm) | 28 | 105 | 30 | 107 | 33 | 34 | 178 | 12 | 106 | 108 |
| 1136 (1st arm) | 5 | 6 | 7 | 9 | 10 | 138 | 181 | 12 | 175 | 139 |
| 1136 (2nd arm) | 28 | 105 | 30 | 107 | 33 | 34 | 178 | 12 | 106 | 108 |
| 1156 (1st arm) | 5 | 6 | 7 | 9 | 10 | 138 | 177 | 12 | 172 | 139 |
| 1156 (2nd arm) | 28 | 105 | 30 | 107 | 33 | 34 | 178 | 12 | 106 | 108 |
| 1166 (1st arm) | 20 | 21 | 160 | 152 | 25 | 153 | 181 | 12 | 161 | 154 |
| 1166 (2nd arm) | 28 | 105 | 30 | 107 | 33 | 34 | 178 | 12 | 106 | 108 |
| 1167 (1st arm) | 20 | 21 | 160 | 166 | 25 | 153 | 177 | 12 | 161 | 167 |
| 1167 (2nd arm) | 28 | 105 | 30 | 107 | 33 | 34 | 178 | 12 | 106 | 108 |
| 1168 (1st arm) | 20 | 21 | 160 | 152 | 41 | 153 | 181 | 12 | 161 | 168 |
| 1168 (2nd arm) | 28 | 105 | 30 | 107 | 33 | 34 | 178 | 12 | 106 | 108 |
| 1169 (1st arm) | 20 | 21 | 160 | 152 | 41 | 153 | 181 | 12 | 161 | 169 |
| 1169 (2nd arm) | 28 | 105 | 30 | 107 | 33 | 34 | 178 | 12 | 106 | 108 |
| 1170 (1st arm) | 20 | 21 | 160 | 152 | 41 | 153 | 181 | 12 | 161 | 170 |
| 1170 (2nd arm) | 28 | 105 | 30 | 107 | 33 | 34 | 178 | 12 | 106 | 108 |

Each of the bispecific antibodies in Table 5 comprises two arms: a first arm that binds to B37-H-4, and a second arm that binds to CD3. The SEQ ID NO of the amino acid sequences of each of the heavy chain CDRs (VH CDR), light chain CDRs (VL CDR), heavy chain variable region (VH), light chain variable region (VL), heavy chain constant region (OH) and light chain constant region (CL), of both the first arm and the second arm are shown in Table 5. (The amino acid sequence of each of the SEQ ID NOs listed in Table 5 is described in Table 3 in the previous sessions herein.) Each of the VH CDR1 sequences in Table 5 is according to the AbM definition, and each of the VH CDR2, VH CDR3, VL CDR1, VL CDR2, VL CDR3 sequences listed in Table 5 is according to the Kabat definition.

In some embodiments, the present invention provides a bispecific antibody that specifically binds to both B37-H-4 and CD3, comprising a first light chain and a first heavy chain, and a second light chain and a second heavy chain, wherein the first light chain and the first heavy chain form a first arm which comprises a first antigen binding domain that binds to B37-H-4, and the second light chain and the second heavy chain form a second arm which comprises a second antigen binding domain that binds to CD3.

In some embodiments, the first heavy chain comprises a VH and a CH, the first light chain comprises a VL and a CL, the second heavy chain comprises a VH and a CH, and the second light chain comprises a VL and a CL, wherein the first and second heavy chain VH and CH and the first and second light chain VL and CL comprising the same amino acid sequences as those of any of the bispecific antibodies listed in Table 5.

In some embodiments, the first light chain comprises a VL, the first heavy chain comprises a VH, the second light chain comprises a VL and the second heavy chain comprises a VH, wherein each of the VH and VL of the first and second heavy chain and first and second light chain having the same amino acid sequence of that of any one of the bispecific antibodies listed in Table 5.

In some embodiments, the first light chain comprises a VL CDR1, a VL CDR2 and a VL CDR3, the first heavy chain comprises a VH CDR1, a VH CDR2 and a VH CDR3, the second light chain comprising a VL CDR1, a VL CDR2 and a VL CDR3, and the second heavy chain comprises a VH CDR1, a VH CDR2 and a VH CDR3, wherein each of the VL CDR1, the VL CDR2, the VL CDR3, the VH CDR1, the VH CDR2 and the VH CDR3 of the first arm and of the second arm of the bispecific antibodies of the present invention, having the same amino acid sequence as that of the VL CDR1, VL CDR2, VL CDR3, VH CDR1, VH CDR2 and VH CDR3, of the first arm and the second arm, respectively, of any one of the bispecific antibodies described in Table 5. In some embodiments, the CDRs are defined according to the Kabat definition, the Chothia definition, the AbM definition, or a combination of the Kabat and Chothia CDR (also termed "combined CDRs" or "extended CDRs").

Constant Regions of B7-H4 Antibodies, CD3 Antibodies and B7-H4×CD3 Bispecific Antibodies In some embodiments, an antibody provided herein comprises one or more constant regions. In some embodiments, an antibody can be, for example, a full-length human antibody. In some embodiments, the full-length human antibody has an IgG1, IgG2, IgG3, or IgG4 isotype. In some embodiments, an antibody can comprise an immunologically inert Fc region.

Unless otherwise specified, all numbering herein of the constant regions of human IgG1, IgG2 and IgG4 is according to the EU numbering scheme, and with reference to the wild type human IgG1, IgG2 and IgG4 respectively. The numbering of the hinge-CH2 region of the human IgG1, IgG2 and IgG4 is as described and exemplified in FIG. 1. The sequences used in the FIG. 1 for IgG2, IgG1 and IgG4 are the CH1, H, CH2 and CH3 regions of IGHG2*01, IGHG1*01 and IGHG4*01 from the human IGHC group of the IMGT/Gene-DB (IMGT/GENE-DB: Giudicelli, V. et al. Nucleic Acids Res., 33: D256-D261 (2005). PMID: 15608191)

In some embodiments, the Fc is a human IgG4 Fc. In some embodiments, an antibody provided herein can comprise a constant region of IgG4 comprising the following mutations (Armour et al., 2003, Molecular Immunology 40 585-593): E233F234L235 to P233V234A235 (IgG4Δc). In yet another embodiment, the Fc can be human IgG4 E233F234L235 to P233V234A235 with deletion G236 (IgG4Δb). In some embodiments the Fc can be any human IgG4 Fc (IgG4, IgG4Δb or IgG4Δc) containing a hinge stabilizing mutation S228 to P228 (Aalberse et al., 2002, Immunology 105, 9-19).

In some embodiments, the Fc is a human IgG2 Fc. In some embodiments, the Fc is a human IgG2 containing the mutation A330P331 to S330S331 (IgG2Δa), in which and in the rest of the paragraph the amino acid residues are numbered with reference to the wild type human IgG2 sequence and following EU numbering scheme. (Eur. J. Immunol., 1999, 29:2613-2624). In some embodiments, the Fc is a human IgG2Δa Fc, with the substitution of D265A. In some embodiments, the antibody further contains mutation at positions 223, 225, and 228 (e.g., (C223E or C223R), (E225R), and (P228E or P228R)) in the hinge region and in the Fc at position 409 or 368 (e.g., K409R or L368E) in the CH3 region of the human IgG2. FIG. 1 shows the specific numbering of the human IgG2 constant regions used herein incorporating the EU numbering scheme.

In some embodiments, the antibody of the present invention comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Publication No. WO99/058572.

In some embodiments, the constant regions of the antibody of the present invention can be modified to avoid interaction with Fc gamma receptor and the complement and immune systems. The techniques for preparation of antibodies with such constant regions are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

In some embodiments, the antibody of the current invention comprises constant region modifications as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody of the present invention comprises a modified constant region that has increased binding affinity for FcRn and/or an increased serum half-life as compared with the unmodified antibody.

In some embodiments, the antibody of the present invention comprises a heavy chain constant region comprising the amino acid sequences selected from the group consisting of SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO:184, and SEQ ID NO;185.

In some embodiments, the antibody of the present invention comprises a light chain constant region comprising the amino acid sequence of SEQ ID NO: 12 or SEQ ID NO: 121.

In some embodiments, the B7-H4×CD3 bispecific antibody of the present invention comprises a first heavy chain and a second heavy chain, and each of the heavy chain contains a hinge region. In some embodiments, the hinge region of one of the heavy chains contains amino acid modification, wherein the substituting amino acid has an opposite charge to the corresponding amino acid in hinge region of the other heavy chain of the bispecific antibody. This approach is described in International Patent Application No. PCT/US2011/036419 (WO2011/143545).

In some embodiments, the B7-H4×CD3 bispecific antibody of the present invention comprises a first and a second immunoglobulin-like Fc region, and the bispecific antibody is enhanced by altering or engineering an interface between the first and the second immunoglobulin-like Fc region (e.g., a hinge region and/or a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545).

In some embodiments, the B7-H4×CD3 bispecific antibody of the present invention comprises a glutamine-containing peptide tag engineered to the antibody arm directed to B7-H4 and another peptide tag (e.g., a Lys-containing peptide tag or a reactive endogenous Lys) engineered to the antibody arm directed to the second antigen. This approach is described in International Patent Application No. PCT/IB2011/054899 (WO2012/059882).

In some embodiments, the bispecific antibody of the present invention comprises a full-length human antibody, comprising a first light chain and a first heavy chain, and a second light chain and a second heavy chain, wherein the first light chain and the first heavy chain form a first antibody arm which comprises a first antigen binding domain that binds to B7-H4, and the second light chain and the second heavy chain form a second antibody arm which forms a second antigen binding domain that binds to CD3. In some embodiments, the bispecific antibody is a full length human IgG2. In some embodiments, the bispecific antibody is a full length IgG2 containing the mutation A330P331 to S330S331 (IgG2Δa). In some embodiments, the bispecific anybody is a human IgG2Δa further comprising a mutation of D265A. In some embodiments, the first heavy chain comprises amino acid modifications at positions 223, 228 and/or 368. In some embodiments, the amino acid medications at positions 223, 228 and 368 of the first heavy chain are C223E, P228E and/or L368E. In some embodiments, the second heavy chain comprises amino acid modifications at positions 223, 225, 228 and/or 409. In some embodiments, the amino acid modifications at positions 223, 225, 228 and 409 of the second heavy chain are C223R, E225R, P228R and/or K409R.

In some embodiments, the bispecific antibody is a full length human IgG2Δa D265A wherein the first heavy chain further comprises amino acid modifications of C223E, P228E and L368E, and the second heavy chain further comprises amino acid modifications of C223R, E225R, P228R and K409R. All amino acid numbering herein is according to the human IgG2 wildtype and EU numbering scheme (Eur. J. Immunol., 1999, 29:2613-2624) and as shown in FIG. 1. FIG. 1 depicts the alignment of the amino acid sequences of: the first heavy chain constant region (B7-H4 binding arm, top), the second heavy chain constant region (CD3 binding arm, middle), both as described in this paragraph, and the human IgG2 wildtype constant region (bottom).

In some embodiments, the first heavy chain of the bispecific antibody comprises a constant region comprising the amino acid sequence of SEQ ID NO:181 or SEQ ID NO: 177, and the second heavy chain of the bispecific antibody comprises a constant region comprising the amino acid sequence of SEQ ID NO: 178.

In some embodiments, the first heavy chain and the second heavy chain of the bispecific antibody comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IG1.

In some embodiments, the first heavy chain and the second heavy chain of the bispecific antibody comprise amino acid modifications at positions 228 (e.g., (P228E or P228R)) in the hinge region and at position 409 or 368 (e.g., R409 or L368E (EU numbering scheme)) in the CH3 region of human IgG4.

The antibody of the present invention, including the B7-H4 antibodies, B7-H4×CD3 bispecific antibodies, and the B7-H4×CD3 bispecific antibodies, encompass monoclonal antibodies, polyclonal antibodies, antibody fragments (e.g., Fab, Fab', F(ab')2, Fv, Fc, etc.), chimeric antibodies, single chain variable region fragments (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

Polynucleotides, Vectors and Host Cells

Polynucleotides

The present invention also provides polynucleotides encoding the B7-H4 antibodies, including the B7-H4×CD3 bispecific antibodies, and the CD3 antibodies of the invention, and vectors and host cells comprising the polynucleotide.

The invention also provides compositions, such as pharmaceutical compositions comprising any of the polynucleotides of the invention. In some embodiments, the composition comprises an expression vector comprising a polynucleotide encoding any of the antibodies described herein. In some embodiments, the composition comprises an expression vector comprising either or both of the polynucleotides shown in SEQ ID NO: 196 and SEQ ID NO:

197. In some embodiments, the composition comprises either or both of the polynucleotides shown in SEQ ID NO: 192 and SEQ ID NO: 193. In still some embodiments, the composition comprises either or both of the polynucleotides shown in SEQ ID NO: 194 and SEQ ID NO: 195.

Polynucleotides complementarity to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementarity sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C. followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Vectors

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Host Cells

The invention also provides host cells comprising any of the polynucleotides described herein. Any host cell capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to B7-H4 or an B7-H4 domain (e.g., domains 1-4) is effected by an immunoassay or FACS. A cell overexpressing the antibody or protein of interest can be identified.

Protein Expression and/or Delivery

An expression vector can be used to direct expression of a B7-H4, CD3, or other tumor antigen antibody. One skilled in the art is familiar with administration of expression vectors to obtain expression of an exogenous protein in vivo. See, e.g., U.S. Pat. Nos. 6,436,908; 6,413,942; and 6,376, 471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1995, 1:185; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Pat. No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 14:2411, 1994 and in Woffendin, Proc. Natl. Acad. Sci., 91:1581, 1994.

ATCC Deposits

Representative materials of the present invention were deposited in the American Type Culture Collection (ATCC) on Jun. 19, 2020. Vector having ATCC Accession No. PTA-126779 contains a polynucleotide encoding the full length first heavy chain (B7-H4 arm) of bispecific antibody 1167. Vector having ATCC Accession No. PTA-126781 contains a polynucleotide encoding the full length first light chain (B7-H4 arm) of bispecific antibody 1167. Vector having ATCC Accession No. PTA-126780 contains a polynucleotide encoding the full length second heavy chain (CD3 arm) of bispecific antibody 1167. Vector having ATCC Accession No. PTA-126782 contains a polynucleotide encoding the full length second light chain (CD3 arm) of bispecific antibody 1167.

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Method of Making the Antibodies of the Present Invention.

The antibodies of the present invention may be made by any method known in the art and as described herein.

For example, the B7-H4 antibody described herein can be identified or characterized using methods known in the art, whereby binding to B7-H4 are detected and/or measured. In some embodiments, a B7-H4 antibody is identified by conducting a binding assay of a candidate agent with B7-H4. The binding assay may be performed with purified B7-H4 polypeptide(s), or with cells naturally expressing, or transfected to express, B7-H4 polypeptide(s). In one embodiment, the binding assay is a competitive binding assay, where the ability of a candidate antibody to compete with a known B7-H4 antibody for B7-H4 binding is evaluated. The assay may be performed in various formats, including the ELISA format.

Following initial identification, the activity of a candidate B7-H4 antibody, can be further confirmed and refined by bioassays, known to test the targeted biological activities. Alternatively, bioassays can be used to screen candidates directly. Some of the methods for identifying and characterizing antibodies are described in detail in the Examples.

B7-H4 antibodies can be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a B7-H4, CD3, or other tumor antigen antibody. In another example, the epitope to which the B7-H4, CD3, or other tumor antigen antibody binds can be determined in a systematic screening by using overlapping peptides derived from the B7-H4, CD3, or other tumor antigen sequence and determining binding by the B7-H4, CD3, or other tumor antigen antibody. According to the gene fragment expression assays, the open reading frame encoding B7-H4, CD3, or other tumor antigen is fragmented either randomly or by specific genetic constructions and the reactivity of the expressed fragments of B7-H4, CD3, or other tumor antigen with the antibody to be tested is determined. The gene fragments may, for example, be produced by PCR and then transcribed and translated into protein in vitro, in the presence of radioactive amino acids. The binding of the antibody to the radioactively labeled B7-H4, CD3, or other tumor antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant B7-H4, CD3, or other tumor antigen in which various fragments of the B7-H4, CD3, or other tumor antigen protein have been replaced (swapped) with sequences from B7-H4 from another species (e.g., mouse), or a closely related, but antigenically distinct protein (e.g., B7-H3). By assessing binding of the antibody to the mutant B7-H4, CD3, or other tumor antigen, the importance of the particular B7-H4, CD3, or other tumor antigen fragment to antibody binding can be assessed.

Yet another method which can be used to characterize a B7-H4, CD3, or other tumor antigen antibody is to use competition assays with other antibodies known to bind to the same antigen, i.e., various fragments on B7-H4, CD3, or other tumor antigen, to determine if the B7-H4, CD3, or other tumor antigen antibody binds to the same epitope as other antibodies. Competition assays are well known to those of skill in the art.

Pharmaceutical Compositions and Formulations

The present invention provides pharmaceutical compositions comprising an effective amount of a B7-H4 antibody or of a B7-H4×CD3 bispecific antibody of the invention. The pharmaceutical composition may be in various formulations.

Various formulations of the B7-H4 antibody, including the B7-H4×CD3 bispecific antibody of the present invention may be used for administration. In some embodiments, the antibody may be administered neat. In some embodiments, the antibody and a pharmaceutically acceptable excipient may be in various formulations. Pharmaceutically acceptable excipients are known in the art. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 21st Ed. Mack Publishing, 2005. In some embodiments, these agents (the excipients) are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Therapeutic formulations of the B7-H4 antibody, including the B7-H4×CD3 bispecific antibody, of the present invention used in accordance to the methods of the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ PLURONICS™ or polyethylene glycol (PEG).

Liposomes containing the B7-H4 antibody, including the B7-H4×CD3 bispecific antibody, of the present invention are prepared by methods known in the art, such as described in Epstein, et al., Proc. Natl. Acad. Sci. USA 82:3688, 1985; Hwang, et al., Proc. Natl Acad. Sci. USA 77:4030, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic antibody, e.g. the B7-H4 antibody, including the B7-H4×CD3 bispecific antibody of the present invention compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing the B7-H4 antibody, including the B7-H4×CD3 bispecific antibody of the present invention, with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Methods of Using the Antibodies of the Present Invention

The antibodies of the present invention are useful in various applications including, but are not limited to, therapeutic treatment methods and diagnostic treatment methods.

Therapeutic Treatment:

In one aspect, the invention provides a method, for treating a condition associated with B7-H4 expression in a subject. In another aspect, the invention provides a B7-H4 antibody, including a B7-H4×CD3 bispecific antibody, or pharmaceutical composition comprising a B7-H4 antibody, including a B7-H4×CD3 bispecific antibody, of the present invention for treating a condition associated with B7-H4 expression in a subject. In some embodiments, the method of treating a condition associated with B7-H4 expression in a subject comprises administering to the subject in need thereof an effective amount of a pharmaceutical composition comprising a B7-H4 antibody, including a B7-H4×CD3 bispecific antibody, of the invention. In some embodiments, the condition is a cancer. As used herein, cancers include, but are not limited to bladder cancer, breast cancer, cervical cancer, choriocarcinoma, colon cancer, esophageal cancer, gastric cancer, glioblastoma, glioma, brain tumor, head and neck cancer, kidney cancer, lung cancer, oral cancer, ovarian cancer, pancreatic cancer, prostate cancer, liver cancer, uterine cancer, bone cancer, leukemia, lymphoma, sarcoma, blood cancer, thyroid cancer, thymic cancer, eye cancer, and skin cancer. In some embodiments, the cancer is breast cancer, bladder cancer, cancer of the uterus or ovarian cancer.

In some embodiments, provided is a method of, and a B7-H4 antibody, including a B7-H4×CD3 bispecific antibody, or pharmaceutical composition for, (1) inhibiting tumor growth or progression in a subject who has malignant cells expressing B7-H4, (2) inhibiting metastasis cells expressing B7-H4 in a subject, or (3) inducing tumor regression in malignant cells in a subject, comprising administering to the subject in need thereof an effective amount of a pharmaceutical composition comprising a B7-H4 antibody, including a B7-H4×CD3 bispecific antibody, as described herein.

In some embodiments, provided is a method of, and a B7-H4 antibody, including a B7-H4×CD3 bispecific antibody, or pharmaceutical composition for, treating an autoimmune disorder in a subject comprising administering to the subject in need thereof an effective amount of a pharmaceutical composition comprising a B7-H4 antibody, including a B7-H4×CD3 bispecific antibody, as described herein. As used herein, autoimmune disorders include, but are not limited to, systemic lupus erythematosus, rheumatoid arthritis, diabetes (Type I), multiple sclerosis, Addison's disease, celiac disease, dermatomyositis, Graves' disease, hashimoto's thyroiditis, hashimoto's encephalopathy, Myasthenia gravis, pernicious anemia, reactive arthritis, Sjogren syndrome, acute disseminated encephalomyelitis, agammaglobulinemia, amyotrophic lateral sclerosis, ankylosing spondylitis, antiphospholipid syndrome, antisynthetase syndrome, atopic allergy, atopic dermatitis, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendorcrine syndrome, autoimmune progesterone dermatitis, autoimmune thrombocytopenic purpura, autoimmune urticarial, autoimmune uveitis, Bechet's disease, Castleman's disease, cold agglutinin disease, Crohn's disease, dermatomyositis, eosinophilic fasciitis, gastrointestinal pemphigoid, Goodpasture's syndrome, Guillain-Barre syndrome, hidradenitis suppurativa, idiopathic thrombocytopenic purpura, narcolepsy, pemphigus vulgaris, pernicious anaemia, polymyositis, primary billary cirrhosis, relapsing polychrondritis, rheumatic fever, temporal arteritis, transverse myelitis, ulcerative colitis, undifferentiated connective tissue disease, vasculitis, and Wegener's granulomatosis.

Diagnostic Treatment:

In another aspect, provided is a method of detecting, diagnosing, and/or monitoring a condition associated with B7-H4 expression. For example, the B7-H4 antibodies, including the B7-H4×CD3 bispecific antibodies, as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent. Alternatively, the method may be used for in vitro or ex vivo diagnostic assays.

In one aspect there is provided the B7-H4 antibodies, including the B7-H4×CD3 bispecific antibodies, as described herein, for use in diagnosis, preferably for use in diagnosing a condition associated with B7-H4 expression.

Delivery Route:

The B7-H4 antibodies, including the B7-H4×CD3 bispecific antibodies of the present invention can be administered to an individual via any suitable route. Accordingly, in some embodiments, the antibody is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibody can be aerosolized using a fluorocarbon formulation and a metered dose inhaler, or inhaled as a lyophilized and milled powder.

In one embodiment, the antibody is administered via site-specific or targeted local delivery techniques. Examples of site-specific or targeted local delivery techniques include various implantable depot sources of the antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Dosage:

The B7-H4 antibody, including the B7-H4×CD3 bispecific antibody of the present invention can be administered using any suitable method, including by injection (e.g., intraperitoneally, intravenously, subcutaneously, intramuscularly, etc.). The antibody can also be administered via inhalation, as described herein. Generally, for administration of an antibody an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to inhibit or delay tumor growth/progression or metastasis of cancer cells. An exemplary dosing regimen comprises administering an initial dose of about 2 mg/kg, followed by a weekly maintenance dose of about 1 mg/kg of the antibody, or followed by a maintenance dose of about 1 mg/kg every other week. Other exemplary dosing regimen comprises administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some embodiments, dosing from one to four times a week is contemplated. In other embodiments, dosing once a month or once every other month or every three months is contemplated. The progress of this therapy is easily monitored by conventional techniques and assays. The dosing regimen of the antibody can vary over time.

For the purpose of the present invention, the appropriate dosage of the B7-H4 antibody, including B7-H4×CD3 bispecific antibodies, of the present invention, would depend on the type and severity of symptoms to be treated, whether the agent is administered for therapeutic purposes, previous therapy, the patient's clinical history and response to the agent, the patient's clearance rate for the administered agent, and the discretion of the attending physician. Typically, the clinician will administer the antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of antibodies may be appropriate. Various formulations and devices for achieving sustained release are known in the art.

In one embodiment, dosages for the B7-H4 antibody, including the B7-H4×CD3 bispecific antibody, of the present invention may be determined empirically in individuals who have been given one or more administration(s) of the antibody. Individuals can be given incremental dosages of the antibody. To assess efficacy, an indicator of the disease can be followed.

Administration of the B7-H4 antibody, including the B7-H4×CD3 bispecific antibody, of the present invention in accordance to the method in the present invention can be continuous or intermittent, depending, for example, upon the recipient's physiological condition, whether the purpose of the administration is therapeutic or prophylactic, and other factors known to skilled practitioners. The administration of the antibody may be essentially continuous over a preselected period of time or may be in a series of spaced doses.

In some embodiments, more than one of the B7-H4 antibody, including the B7-H4×CD3 bispecific antibody, of the present invention may be present. At least one, at least two, at least three, at least four, at least five different or more the B7-H4 antibody, including the B7-H4×CD3 bispecific antibody can be present. Generally, those antibodies may have complementary activities that do not adversely affect each other. For example, one or more of the following antibodies may be used: a first B7-H4 or CD3 antibody directed to one epitope on B7-H4 or CD3 and a second B7-H4 or CD3 antibody directed to a different epitope on B7-H4 or CD3.

Combinations

In some embodiments, the B7-H4 antibody, including the B7-H4×CD3 bispecific antibody, of the present invention may be administered in combination with the administration of one or more additional therapeutic agents. The additional therapeutic agents include, but are not limited to, a biotherapeutic agent and/or a chemotherapeutic agent, such as but not limited to, a vaccine, a CAR-T cell-based therapy, radiotherapy, a cytokine therapy, a CD3 bispecific antibody, an inhibitor of other immunosuppressive pathways, an inhibitor of angiogenesis, a T cell activator, an inhibitor of a metabolic pathway, an mTOR inhibitor, an inhibitor of an adenosine pathway, a tyrosine kinase inhibitor including but not limited to Inlyta, ALK inhibitors and sunitinib, a BRAF inhibitor, an epigenetic modifier, an IDO1 inhibitor, a JAK inhibitor, a STAT inhibitor, a cyclin-dependent kinase inhibitor, a biotherapeutic agent (including but not limited to antibodies to VEGF, VEGFR, EGFR, Her2/neu, other growth factor receptors, CD40, CD-40L, CTLA-4, OX-40, 4-1BB, TIGIT, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of biotherapeutic agents include therapeutic antibodies, immune modulating agents, and therapeutic immune cells.

Therapeutic antibodies may have specificity against a variety of different of antigens. For example, therapeutic antibodies may be directed to a tumor associated-antigen, such that binding of the antibody to the antigen promotes death of the cell expressing the antigen. In other example, therapeutic antibodies may be directed to an antigen (e.g. PD-1) on an immune cell, such that binding of the antibody prevents downregulation of the activity of the cell expressing the antigen (and thereby promotes activity of the cell expressing the antigen). In some situations, a therapeutic antibody may function through multiple different mechanisms (for example, it may both i) promote death of the cell expressing the antigen, and ii) prevent the antigen from causing down-regulation of the activity of immune cells in contact with the cell expressing the antigen).

Therapeutic antibodies may be directed to, for example, the antigens listed as follows. For some antigens, exemplary antibodies directed to the antigen are also included below (in brackets/parenthesis after the antigen). The antigens as follow may also be referred to as "target antigens" or the like herein. Target antigens for therapeutic antibodies herein include, for example: 4-1BB (e.g. utomilumab); 5T4; A33; alpha-folate receptor 1 (e.g. mirvetuximab soravtansine); Alk-1; B7-H4 [e.g. PF-06863135 (see U.S. Pat. No. 9,969,809)]; BTN1A1 (e.g. see WO2018222689); CA-125 (e.g. abagovomab); Carboanhydrase IX; CCR2; CCR4 (e.g. mogamulizumab); CCR5 (e.g. leronlimab); CCR8; CD3 [e.g. blinatumomab (CD3/CD19 bispecific), PF-06671008 (CD3/P-cadherin bispecific), PF-06863135 (CD3/B7-H4 bispecific), CD19 (e.g. blinatumomab, MOR208); CD20 (e.g. ibritumomab tiuxetan, obinutuzumab, ofatumumab, rituximab, ublituximab); CD22 (inotuzumab ozogamicin, moxetumomab pasudotox); CD25; CD28; CD30 (e.g. brentuximab vedotin); CD33 (e.g. gemtuzumab ozogamicin); CD38 (e.g. daratumumab, isatuximab), CD40; CD-40L; CD44v6; CD47; CD52 (e.g. alemtuzumab); CD63; CD79 (e.g. polatuzumab vedotin); CD80; CD123; CD276/B7-H3 (e.g. omburtamab); CDH17; CEA; CIhCG; CTLA-4 (e.g. ipilimumab, tremelimumab), CXCR4; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIII; Endosialin; EpCAM (e.g. oportuzumab monatox); FAP; Fetal Acetylcholine Receptor; FLT3 (e.g. see WO2018/220584); GD2 (e.g. dinutuximab, 3F8); GD3; GITR; GloboH; GM1; GM2; GUCY2C (e.g. PF-07062119); HER2/neu [e.g. margetuximab, pertuzumab, trastuzumab; ado-trastuzumab emtansine, trastuzumab duocarmazine, PF-06804103 (see U.S. Pat. No. 8,828,401)]; HER3; HER4; ICOS; IL-10; ITG-AvB6; LAG-3 (e.g. relatlimab); Lewis-Y; LG; Ly-6; M-CSF [e.g. PD-0360324 (see U.S. Pat. No. 7,326,414)]; MCSP; mesothelin; MUC1; MUC2; MUC3; MUC4; MUC5AC; MUC5B; MUC7; MUC16; Notch1; Notch3; Nectin-4 (e.g. enfortumab vedotin); OX40 [e.g. PF-04518600 (see U.S. Pat. No. 7,960,515)]; P-Cadherein [e.g. PF-06671008 (see WO2016/001810)]; PCDHB2; PD-1 [e.g. BCD-100, camrelizumab, cemiplimab, genolimzumab (CBT-501), MED10680, nivolumab, pembrolizumab, sasanlimab (see WO2016/092419), sintilimab, spartalizumab, STI-A1110, tislelizumab, TSR-042]; PD-L1 (e.g. atezolizumab, durvalumab, BMS-936559 (MDX-1105), or LY3300054); PDGFRA (e.g. olaratumab); Plasma Cell Antigen; PolySA; PSCA; PSMA; PTK7 [e.g. PF-06647020 (see U.S. Pat. No. 9,409,995)]; Ror1; SAS; SCRx6; SLAMF7 (e.g. elotuzumab); SHH; SIRPa (e.g. ED9, Effi-DEM); STEAP; TGF-beta; TIGIT; TIM-3; TMPRSS3; TNF-alpha precursor; TROP-2 (e.g sacituzumab govitecan); TSPAN8; VEGF (e.g. bevacizumab, brolucizumab); VEGFR1 (e.g. ranibizumab); VEGFR2 (e.g. ramucirumab, ranibizumab); Wue-1.

Immune modulating agents include a variety of different molecule types which may stimulate an immune response in a subject, such as pattern recognition receptor (PRR) agonists, immunostimulatory cytokines, and cancer vaccines.

Pattern recognition receptors (PRRs) are receptors that are expressed by cells of the immune system and that recognize a variety of molecules associated with pathogens and/or cell damage or death. PRRs are involved in both the innate immune response and the adaptive immune response. PRR agonists may be used to stimulate the immune response in a subject. There are multiple classes of PRR molecules, including toll-like receptors (TLRs), RIG-1-like receptors (RLRs), nucleotide-binding oligomerization domain (NOD)-like receptors (NLRs), C-type lectin receptors (CLRs), and Stimulator of Interferon Genes (STING) protein.

The terms "TLR" and "toll-like receptor" refer to any toll-like receptor. Toll-like receptors are receptors involved in activating immune responses. TLRs recognize, for example, pathogen-associated molecular patterns (PAMPs) expressed in microbes, as well as endogenous damage-associated molecular patterns (DAMPs), which are released from dead or dying cells.

Molecules which activate TLRs (and thereby activate immune responses) are referred to herein as "TLR agonists". TLR agonists can include, for example, small molecules (e.g. organic molecule having a molecular weight under about 1000 Daltons), as well as large molecules (e.g. oligonucleotides and proteins). Some TLR agonists are specific for a single type of TLR (e.g. TLR3 or TLR9), while some TLR agonists activate two or more types of TLR (e.g. both TLR7 and TLR8).

Exemplary TLR agonists provided herein include agonists of TLR2, TLR3, TLR4, TLR5, TLR6, TLR7, TLR8, and TLR9.

Exemplary small molecule TLR agonists include those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091,214; U.S. Patent Publication Nos. 2004/0091491, 2004/0176367, and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826. WO 2006/009832. WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852.

Additional examples of small molecule TLR agonists include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), and certain 3-.beta.-D-ribofuranosylthiazolo[4,5-d]pyrimidine derivatives (such as those described in U.S. Publication No. 2003/0199461), and certain small molecule immuno-potentiator compounds such as those described, for example, in U.S. Patent Publication No. 2005/0136065.

Exemplary large molecule TLR agonists include as oligonucleotide sequences. Some TLR agonist oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other TLR agonist nucleotide sequences lack CpG sequences and are described, for example, in International Patent Publication No. WO 00/75304. Still other TLR agonist nucleotide sequences include guanosine- and uridine-rich single-stranded RNA (ssRNA) such as those described, for example, in Heil et ah, Science, vol. 303, pp. 1526-1529, Mar. 5, 2004.

Other TLR agonists include biological molecules such as aminoalkyl glucosaminide phosphates (AGPs) and are described, for example, in U.S. Pat. Nos. 6,113,918; 6,303,347; 6,525,028; and 6,649,172.

TLR agonists also include inactivated pathogens or fractions thereof, which may activate multiple different types of TLR receptor. Exemplary pathogen-derived TLR agonists include BCG, *Mycobacterium obuense* extract, Talimogene laherparepvec (T-Vec) (derived from HSV-1), and Pexa-Vec (derived from vaccina virus).

In some embodiments, a TLR agonist may be an agonist antibody that binds specifically to the TLR.

RLRs include various cytosolic PRRs that detect, e.g. dsRNAs. Examples of RLRs include, for example, retinoic acid-inducible gene I (RIG-1), melanoma differentiation-associated gene 5 (MDA-5), and Laboratory of Genetics and Physiology 2 (LGP2).

"RLR agonist" as used herein means, any molecule, which upon binding to an RLR, (1) stimulates or activates the RLR, (2) enhances, increases, promotes, induces, or prolongs an activity, function, or presence of the RLR, or (3) enhances, increases, promotes, or induces the expression of RLR. RLR agonists useful in the any of the treatment methods, medicaments and uses of the present invention include, for example, nucleic acids and derivatives thereof which bind RLRs and agonistic monoclonal antibodies (mAb) which specifically binds to RLRs.

Examples of RLRs agonists that are useful in the treatment methods, medicaments, and uses of the present invention include, for example, short double-stranded RNA with uncapped 5' triphosphate (RIG-I agonist); poly 1:C (MDA-5 agonist), and BO-112 (MDA-A agonist).

NLRs include various PRRs that detect, e.g. damage-associated molecular pattern (DAMP) molecules. NLRs include the subfamilies NLRA-A, NLRB-B, NLRC-C, and NLRP-P. Examples of NLRs include, for example, NOD1, NOD2, NAIP, NLRC4, and NLRP3.

"NLR agonist" as used herein means, any molecule, which upon binding to an NLR, (1) stimulates or activates the NLR, (2) enhances, increases, promotes, induces, or prolongs an activity, function, or presence of the NLR, or (3) enhances, increases, promotes, or induces the expression of NLR. NLR agonists useful in the any of the treatment methods, medicaments and uses of the present invention include, for example, DAMPs and derivatives thereof which bind NLRs and agonistic monoclonal antibodies (mAb) which specifically binds to NLRs.

Examples of NLR agonists that are useful in the treatment methods, medicaments, and uses of the present invention include, for example, liposomal muramyl tripeptide/mifamurtide (NOD2 agonist).

CLRs include various PRRs that detect, e.g. carbohydrates and glycoproteins. CLRs include both transmembrane CLRs and secreted CLRs. Examples of CLRs include, for example, DEC-205/CD205, macrophage mannose receptor (MMR), Dectin-1, Dectin-2, mincle, DC-SIGN, DNGR-1, and mannose-binding lectin (MBL).

"CLR agonist" as used herein means, any molecule, which upon binding to a CLR, (1) stimulates or activates the CLR, (2) enhances, increases, promotes, induces, or prolongs an activity, function, or presence of the CLR, or (3) enhances, increases, promotes, or induces the expression of CLR. CLR agonists useful in the any of the treatment methods, medicaments and uses of the present invention include, for example, carbohydrates and derivatives thereof which bind CLRs and agonistic monoclonal antibodies (mAb) which specifically binds to CLRs.

Examples of CLR agonists that are useful in the treatment methods, medicaments, and uses of the present invention include, for example, MD-fraction (a purified soluble beta-glucan extract from *Grifola frondosa*) and imprime PGG (a beta 1,3/1,6-glucan PAMP derived from yeast).

The STING protein functions as both a cytosolic DNA sensor and an adaptor protein in Type 1 interferon signaling.

The terms "STING" and "stimulator of interferon genes" refer to any form of the STING protein, as well as variants, isoforms, and species homologs that retain at least a part of the activity of STING. Unless indicated differently, such as by specific reference to human STING, STING includes all mammalian species of native sequence STING, e.g. human, monkey, and mouse. One exemplary human TLR9 is provided under UniProt Entry No. Q86WV6. STING is also known as TMEM173.

"STING agonist" as used herein means, any molecule, which upon binding to TLR9, (1) stimulates or activates STING, (2) enhances, increases, promotes, induces, or prolongs an activity, function, or presence of STING, or (3) enhances, increases, promotes, or induces the expression of STING. STING agonists useful in the any of the treatment method, medicaments and uses of the present invention include, for example, nucleic acid ligands which bind STING.

Examples of STING agonists that are useful in the treatment methods, medicaments, and uses of the present invention include various immunostimulatory nucleic acids, such as synthetic double stranded DNA, cyclic di-GMP, cyclic-GMP-AMP (cGAMP), synthetic cyclic dinucleotides (CDN) such as MK-1454 and ADU-S100 (MIW815), and small molecules such as PO-424.

Other PRRs include, for example, DNA-dependent Activator of IFN-regulatory factors (DAI) and Absent in Melanoma 2 (AIM2).

Immunostimulatory cytokines include various signaling proteins that stimulate immune response, such as interferons, interleukins, and hematopoietic growth factors.

Exemplary immunostimulatory cytokines include GM-CSF, G-CSF, IFN-alpha, IFN-gamma; IL-2 (e.g. denileukin difitox), IL-6, IL-7, IL-11, IL-12, IL-15, IL-18, IL-21, and TNF-alpha.

Immunostimulatory cytokines may have any suitable format. In some embodiments, an immunostimulatory cytokine may be a recombinant version of a wildtype cytokine. In some embodiments, an immunostimulatory cytokine may be a mutein that has one or more amino acid changes as compared to the corresponding wildtype cytokine. In some embodiments, an immunostimulatory cytokine may be incorporated into a chimeric protein containing the cytokine and at least one other functional protein (e.g. an antibody). In some embodiments, an immunostimulatory cytokine may covalently linked to a drug/agent (e.g. any drug/agent as described elsewhere herein as a possible ADC component).

Cancer vaccines include various compositions that contain tumor associated antigens (or which can be used to generate the tumor associated antigen in the subject) and thus can be used to provoke an immune response in a subject that will be directed to tumor cells that contain the tumor associated antigen.

Example materials that may be included in a cancer vaccine include, attenuated cancerous cells, tumor antigens, antigen presenting cells such as dendritic cells pulsed with tumor derived antigen or nucleic acids encoding tumor associated antigens. In some embodiments, a cancer vaccine may be prepared with a patient's own cancer cells. In some embodiments, a cancer vaccine may be prepared with biological material that is not from a patient's own cancer cells.

Cancer vaccines include, for example, sipuleucel-T and talimogene laherparepvec (T-VEC).

Immune cell therapy involves treating a patient with immune cells that are capable of targeting cancer cells. Immune cell therapy includes, for example, tumor-infiltrating lymphocytes (TILs) and chimeric antigen receptor T cells (CAR-T cells).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g., calicheamicin, especially calicheamicin gamma1I and calicheamicin phil1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), pegylated liposomal doxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate;

platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; KRAS inhibitors; MCT4 inhibitors; MAT2a inhibitors; tyrosine kinase inhibitors such as sunitinib, axitinib; alk/c-Met/ROS inhibitors such as crizotinib, lorlatinib; mTOR inhibitors such as temsirolimus, gedatolisib; src/abl inhibitors such as bosutinib; cyclin-dependent kinase (CDK) inhibitors such as palbociclib, PF-06873600; erb inhibitors such as dacomitinib; PARP inhibitors such as talazoparib; SMO inhibitors such as glasdegib, PF-5274857; EGFR T790M inhibitors such as PF-06747775; EZH2 inhibitors such as PF-06821497; PRMT5 inhibitors such as PF-06939999; TGFRβr1 inhibitors such as PF-06952229; and pharmaceutically acceptable salts, acids or derivatives of any of the above. In specific embodiments, such additional therapeutic agent is bevacizumab, cetuximab, sirolimus, panitumumab, 5-fluorouracil (5-FU), capecitabine, tivozanib, irinotecan, oxaliplatin, cisplatin, trifluridine, tipiracil, leucovorin, gemcitabine, regorafinib or erlotinib hydrochloride.

In some embodiments, the B7-H4 antibody, including the B7-H4×CD3 bispecific antibody, of the present invention is used in conjunction with one or more other therapeutic agents targeting an immune checkpoint modulator or costimulatory agent, such as, for example without limitation, an agent targeting CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIM1, TIM-3, TIM4, VISTA (PD-H1), OX40, OX40L, GITR, GITRL, CD70, CD27, 4-1 BB, 4-BBL, DR3, TL1A, CD40, CD40L, CD30, CD30L, LIGHT, HVEM, SLAM (SLAMF1, CD150), SLAMF2 (CD48), SLAMF3 (CD229), SLAMF4 (2B4, CD244), SLAMF5 (CD84), SLAMF6 (NTB-A), SLAMCF7 (CS1), SLAMF8 (BLAME), SLAMF9 (CD2F), CD28, CEACAM1 (CD66a), CEACAM3, CEACAM4, CEACAM5, CEACAM6, CEACAM7, CEACAM8, CEACAM1-3AS CEACAM3C2, CEACAM1-15, PSG1-11, CEACAM1-4C1, CEACAM1-4S, CEACAM1-4L, IDO, TDO, CCR2, CD39-CD73-adenosine pathway (A2AR), BTKs, TIKs, CXCR2, CXCR4, CCR4, CCR8, CCR5, CSF-1, or an innate immune response modulator.

In some embodiments, the B7-H4 antibody, including the B7-H4×CD3 bispecific antibody, of the present invention is used in conjunction with, for example, an anti-CTLA-4 antagonist antibody such as for example ipilimumab; an anti-LAG-3 antagonist antibody such as BMS-986016 and IMP701; an anti-TIM-3 antagonist antibody; an anti-B7-H3 antagonist antibody such as for example MGA271; an-anti-VISTA antagonist antibody; an anti-TIGIT antagonist antibody; antibody; an anti-CD80 antibody; an anti-CD86 antibody; an-anti-B7-H4 antagonist antibody; an anti-ICOS agonist antibody; an anti-CD28 agonist antibody; an innate immune response modulator (e.g., TLRs, KIR, NKG2A), and an IDO inhibitor.

In some embodiments, the B7-H4 antibody, including the B7-H4×CD3 bispecific antibody, of the present invention is used in conjunction with an OX40 agonist such as, for example, an anti-OX-40 agonist antibody. In some embodiments, the B7-H4 antibody, including the B7-H4×CD3 bispecific antibody, of the present invention is used in conjunction with a GITR agonist such as, for example, an-anti-GITR agonist antibody such as, for example without limitation, TRX518. In some embodiments, the B7-H4 antibody, including the B7-H4×CD3 bispecific antibody, of the present invention is used in conjunction with an IDO inhibitor. In some embodiments, a GUCY2c antibody or CD3-GUCY2c bispecific antibody is used in conjunction with a cytokine therapy such as, for example without limitation, IL-15, CSF-1, MCSF-1, etc.

In some embodiments, the B7-H4 antibody, including the B7-H4×CD3 bispecific antibody, of the present invention is used in conjunction with one or more other therapeutic antibodies, such as, for example without limitation, an antibody targeting CD19, CD22, CD40, CD52, or CCR4.

In certain embodiments, the composition of the B7-H4 antibody, including the B7-H4×CD3 bispecific antibody, of the present invention comprises at least one additional agent such as bevacizumab, cetuximb, sirolimus, panitumumab, 5-fluorouracil (5-FU), capecitabine, tivozanib, irinotecan, oxaliplatin, cisplatin, trifluridine, tipiracil, leucovori, gemcitabine and erlotinib hydrochloride.

In some embodiments, the B7-H4 antibody, including the B7-H4×CD3 bispecific antibody, of the present invention may be co-administered with, or be sequentially administered before or after the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, the treatment regimen of B7-H4 antibody, including the B7-H4×CD3 bispecific antibody, of the present invention is combined with a treatment regimen further comprising a traditional therapy selected from the group consisting of: surgery, radiation therapy, chemotherapy, targeted therapy, immunotherapy, hormonal therapy, angiogenesis inhibition and palliative care.

Kits

The invention also provides kits for use in the instant methods. Kits of the invention include one or more containers comprising the B7-H4 antibody, including the B7-H4× CD3 bispecific antibody, of the present invention and instructions for use in accordance with any of the methods of the invention described herein. Generally, these instructions comprise a description of administration the B7-H4 antibody, including the B7-H4×CD3 bispecific antibody, of the present invention for the above described therapeutic treatments.

The instructions relating to the use of the B7-H4 antibody, including the B7-H4×CD3 bispecific antibody, of the present invention as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is the B7-H4 antibody, including the B7-H4×CD3 bispecific antibody, of the present invention. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1. High-Throughput Expression and Purification of B7-H4 Antibody and B7-H4×CD3 Bispecific Antibodies Complimentary construct pairs (12.5 µg of each of the heavy chain and the light chain) of the B7-H4 homodimer antibody were co-transfected into 25 mL log phase cultures containing 1 million cells/ml HEK 293 cells using the ExpiFectamine™ 293 Transfection Kit (Life Technologies). 24 hours post-transfection, ExpiFectamine Transfection Enhancer was added and cells were allowed to grow an additional 4-5 days before harvesting. Spent cultures were then collected, centrifuged to remove cell debris then passed through a 20 µm filter.

Clarified conditioned media containing B7-H4 homodimers were then purified using Protein A affinity chromatography. Samples were loaded onto 0.45 mL micro columns (Repligen) pre-packed with MabSelect SuRe™ Protein A resin (GE Healthcare) using a liquid handler (Tecan). Bound protein was washed with PBS pH7.2, then eluted with 20 mM citric acid, 150 mM sodium chloride pH 3.5 and neutralized with 2M tris, pH 8.0. Proteins were analyzed for purity using analytical size exclusion chromatography with a Mab HTP column (Tosoh Bioscience) on an Aglient 1200 HPLC following the manufacturer's protocols. Concentrations were determined by measuring OD280 nm using a micro spectrophotometer (Trinean).

CD3 homodimer antibodies were prepared similarly as the above and were purified from 2 L of culture as described in Example 2. Briefly, 2 L of expi293 cells (Invitrogen) were transfected with 0.5 µg/ml of each of the heavy chain and the light chain according to manufacturer's protocol. The conditioned media were harvested on day 5 and captured by MAB Select SuRe LX resin (GE healthcare).

Bispecific antibodies were formed by mixing equimolar amounts of B7-H4 homodimers and CD3 homodimers and incubating them with 1 mM GSH at 37 C for 24 h. Samples were then de-salted into PBS pH 7.2 using G25 Sephadex drip columns (GE Healthcare) according to the manufacturer's methods. The efficiency of controlled Fab arm exchange (formation of heterodimer) was analyzed using WCX column (GE Healthcare) with a shallow salt gradient (20 mM MES pH 5.4, 0-1 M NaCl).

The B7-H4 antibodies in Table 2 and the B7-H4×CD3 bispecific antibodies in Table 5 were made according to the methods of this invention.

Example 2. Production of B7-H4×CD3 Bispecific Antibody 1167 and 1156 cDNAs encoding B7-H4×CD3 bispecific antibody 1167 anti-B7-H4 arm heavy chain (SEQ ID NO: 196), anti-B7-H4 light chain (SEQ ID NO: 197), B7-H4×CD3 bispecific antibody 1156 anti-B7-H4 arm heavy chain (SEQ ID NO: 192), anti-B7-H4 light chain (SEQ ID NO: 193), anti-CD3 arm heavy chain (SEQ ID NO: 194) and anti-CD3 light chain (SEQ ID NO: 195) were cloned into mammalian expression vectors. Anti-B7-H4 IgG2 dA D265A heavy chains having three additional substitutions of C223E, P228E and L368E (collectively "EEE") and anti-CD3 IgG2 dA D265A having four additional substitutions C223R, E225R, P228R, K409R (collectively "RRR") were transfected together with corresponding light chains and the whole "EEE" and "RRR" arms were expressed separately using 2 L of expi293 cells (Invitrogen) according to manufacturer protocol. The DNA ratio of the heavy and light chain for transfection was 1:1 by weight (1 ug/ml of culture, DNA total). The conditioned media for both homodimers (RRR and EEE) were harvested on day 5 and captured by MAB Select SuRe LX resin separately (GE healthcare). Heterodimerization of the bispecific molecule was conducted in vitro using eluates from the mAb Select SuRe LX resin. Briefly, RRR and EEE homodimers were mixed at a 1:1 molar ratio in the presence of 20-fold and 10 fold molar excess of Cysteine for bispecific antibody 1156 and 1167 respectively. The mixture solution was incubated at room temperature pH 8.0 for 18 hours. Post-RedOx was diluted at 1:4 and 1:9 with 50 mM MES buffer pH 5.6 for bispecific antibody 1156 and 1167, respectively, and then run over the Mono-S column (CEX purification, GE Healthcare Life Sciences) at room temperature. The protein was eluted off the column with Cation Exchange eluting buffer (50 mM MES, 1000 mM NaCl, pH 5.6) with gradient. Purification was performed on an AKTA Pure and Avant (GE Healthcare Life Sciences). The final buffer exchange to PBS-CMF (phosphate buffered saline; calcium and magnesium free) was performed using Sephadex G-25 Fine (GE Healthcare Life Sciences). Protein quantitation was achieved by measuring the absorbance at 280 nm using molar absorption coefficient calculated from amino acid sequence.

Example 3. Competition ELISA to Test IC50 Against Plate Bound huB7-H4

Binding strength of germlined and optimized variants described in below Table 7 was assessed in ELISA by competition with the parental B7-H4 antibody 0052 or 0058. ELISA plates (Thermo Fisher; 384-well) were coated with 1 μg/mL (25 ug/well) of the B7-H4 extra cellular domain ("ECD") (6×his F29-A258) in PBS buffer overnight at 4° C. with gentle shaking. Coating solution was discarded, and the plates were blocked at room temperature for 1 h with 50 μL PBS-1% BSA per well. Blocking solution was discarded and the plate was washed 4 times with TBST. A series of 2-fold dilutions of the analyzed mAb was prepared and mixed with the concentration corresponding to $EC_{80}$ of biotinylated B7-H4 antibody 0052 (for 28D10 optimization series) or B7-H4 antibody 0058 (for 37D4 optimization series). 25 ul of 1:1 mixture of the diluted tested mAb and the biotinylated parental mAb was added to the plates in two repeats. Plates were incubated for 2 hours at room temperature by slow shaking. Plates were washed 4 times with 100 μL per well of washing buffer (TBST) and incubated for 1 hour with 20 μL of streptavidin-HRP conjugate diluted 1:4000 in PBS/BSA buffer. Plates were washed 7 times as before and incubated for 10 minutes with 20 μL of TNB substrate. The reaction was terminated by adding 0.18 M Sulfuric Acid. Apsorption was then measured at 450 nm using an EnVision® plate reader (EnVision® Multilabel Plate Reader, Perkin Elmer) following the manufacturer's protocol. $EC_{80}$ of the parental antibodies 0052 and 0058 was determined by incubating biotinylated 0052 and 0058 at room temperature with plates coated with human B7-H4 ECD prepared as described above. A series of 2-fold dilutions of the antibodies were prepared and 25 ul was added to the wells. After 2 h incubation, the plates were washed and incubated with streptavidin-HRP conjugate diluted 1:4000 in PBS/BSA buffer, followed by washing and addition of the TNB substrate, as described above. The reaction was terminated with 0.18 M Sulfuric Acid and the absorption was then measured at 450 nm using an EnVision® plate reader (EnVision® Multilabel Plate Reader, Perkin Elmer). $EC_{80}$ values were calculated in Graphpad PRISM using four parameter non-linear regression analysis.

Selected antibodies in Table 2 and Table 5 were tested according to this method and the resulting data is shown in Table 7.

Example 4. Affinity Capture Self-Interaction Nanoparticle Spectroscopy (AC-SINS)

Antibody and antibody-like proteins have the potential to interact with themselves, particularly at increased concentrations. This self-interaction can lead to viscosity challenges associated with formulation during drug development as well as increased risk of clearance. (Avery et al. MAbs. 2018; 10(2): 244-255). The AC-SINS assay measures self-interaction and is used to help predict high viscosity and the potential for poor pharmacokinetic properties.

The AC-SINS assay was standardized in a 384-well format on a Perkin-Elmer Janus liquid handling robot. 20 nm gold nanoparticles (Ted Pella, Inc., #15705) were coated with a mixture of 80% goat anti-human Fc (Jackson ImmunoResearch Laboratories, Inc. #109-005-098) and 20% non-specific goat polyclonal antibodies (Jackson ImmunoResearch Laboratories, Inc. #005-000-003) that were buffer exchanged into 20 mM sodium acetate pH 4.3 and diluted to 0.4 mg/ml. After one hour incubation at room temperature, sites unoccupied on the gold nanoparticles were blocked with thiolated polyethylene glycol (2 kD). The coated nanoparticles were then concentrated 10-fold using a syringe filter and 10 μl were added to 100 μl of mAb at 0.05 mg/ml in PBS pH 7.2. The coated nanoparticles were incubated with the antibody of interest for 2 hrs in a 96-well polypropylene plate and then transferred to a 384-well polystyrene plate and read on a Tecan M1000 spectrophotometer. The absorbance was read from 450-650 nm in 2 nm increments, and a Microsoft Excel macro was used to identify the max absorbance, smooth the data, and fit the data using a second-order polynomial. The smoothed max absorbance of the average blank (PBS buffer alone) was subtracted from the smoothed max absorbance of the antibody sample to determine the antibody AC-SINS score.

Selected antibodies in Table 2 and Table 5 were tested according to this method and the resulting data is shown in Table 7.

Example 5. DNA and Insulin Polyspecificity ELISA 384-well ELISA plates (Nunc Maxisorp) were coated overnight at 4° C. with DNA (10 μg/ml) and insulin (5 μg/ml) in PBS pH 7.5. The ELISA, adapted from assays described in Tiller et al., J. Immunol. Methods 329, 112, 2008; U.S. Pat. No. 7,314,622, was carried out on a PerkinElmer Janus liquid handling robot. Wells were washed with water, blocked with 50 μl of Polyreactivity ELISA Buffer (PEB; PBS containing 0.5% Tween-20, 1 mM EDTA) for 1 hour at room temperature, and rinsed three times with water. Serially-diluted mAbs in 25 μl were added in quadruplicate to the wells and incubated for 1 h at room temperature. Plates were washed 3 times with water, and 25 μl of 10 ng/ml goat anti-human IgG, (Fcγ fragment specific) conjugated to horseradish peroxidase (Jackson ImmunoResearch) were added to each well. Plates were incubated for 1 h at room temperature, washed 3 times with 80 μl of water, and 25 μl of TMB substrate (Sigma Aldrich) added to each well. Reactions were stopped after 6 minutes 50 seconds by adding 25 μl of 0.18 M ortho-phosphoric acid to each well and absorbance was read at 450 nm. DNA- and insulin-binding scores were calculated as the ratio of the ELISA signal of the antibody at 10 μg/ml to the signal of a well containing buffer. Selected antibodies in Table 2 and Table 5 were tested to obtain the polyspecificity scores shown therein according to the DNA and Insulin binding ELISA procedure described herein and the data is shown in Table 7.

TABLE 7

Competition ELISA, AC-INS Results of the B7-H4 Antibodies and B7-H4xCD3 bispecific Antibodies

| mAb | AC-SINS | DNA | Insulin | COMPETITION ELISA IC50 [nM] | IC50 [nM] | IC50 [nM] | IC50 [nM] |
|---|---|---|---|---|---|---|---|
| 0001 | 2; 4 | 8; 5 | 8; 8 | | | | |
| 0007 | 19 | 2 | 4 | | | | |
| 0013 | 11 | 2 | 3 | | | | |
| 0047 | 2; 3; 2; 4; 2 | 32; 10; 19; 14; 12 | 21; 11; 19; 10; 13 | 4.8 | 16.9 | 8.2 | 1.2; 1.0 |
| 0048 | 1; 2 | 17; 28 | 13; 12 | | | | |
| 0049 | 2 | 5 | 6 | | | | |
| 0050 | 2; 1 | 34; 28 | 17; 15 | | | | |
| 0051 | 1; 2 | 22; 26 | 12; 8 | | | | |
| 0052 | 14; 9; 17; 13; 22; 21 | 10; 13; 7; 9; 4 | 15; 12; 12; 6; 6 | 6.39 | 16.85 | 7.9 | 1.39; 0.92 |
| 0053 | 3; 1 | 7 | 12 | | | | |
| 0054 | NA | NA | NA | | | | |
| 0055 | 1 | 14 | 6 | | | | |
| 0056 | 0 | 6 | 8 | | | | |
| 0057 | 8; 9 | 17; 12 | 19; 16 | | | | |
| 0058 | 6; 6; 5; 4; 11; 9 | 16; 7; 4; 3; 4; 4 | 13; 6; 8; 5; 5; 5 | 5.25; 4.6 | 10.23 | 3.8 | 0.46 |
| 0059 | 1; 1 | 17; 18 | 20; 22 | | | | |
| 0060 | 2; 2 | 14; 12 | 14; 16 | | | | |
| 0061 | 2 | 9 | 7 | | | | |
| 0068 | 7 | 9 | 12 | | | | |
| 0074 | 3 | 11 | 15 | | | | |
| 0077 | 4 | 12 | 15 | | | | |
| 0080 | 3 | 17 | 14 | | | | |
| 0087 | 3 | 6 | 9 | | | | |
| 0088 | 17 | 21 | 24 | | | | |
| 0089 | 5 | 6 | 8 | | | | |
| 0090 | 5 | 5 | 8 | | | | |
| 0119 | 2; 5 | 5; 4 | 5; 7 | 7.52 | 13.74 | | |
| 0185 | 0 | 5 | 7 | | | | |
| 0267 | 1 | 8 | 8 | 9.42 | | | |
| 0270 | 12 | 6 | 11 | 9.07 | | | |
| 0274 | 11 | 5 | 10 | 4.2 | | | |
| 0277 | 4 | 10 | 8 | 19.02 | | | |
| 0279 | 2 | 9 | 9 | 5.94 | 14.86 | | |
| 0283 | 4; 1 | 16; 8 | 19; 13 | 7.2 | 12.91 | | |
| 0350 | 0 | 5 | 7 | 17.6 | | | |
| 0352 | 0 | 3 | 4 | 15.8 | 12.9 | | |
| 0362 | 0 | 3 | 5 | 13.5 | 17.1 | | |
| 0364 | 0 | 4 | 7 | 9.13 | 10.8 | | |
| 0368 | 2 | 5 | 9 | 8.49 | 8.3 | | |
| 0376 | 0 | 9 | 8 | 12.44 | | | |
| 0380 | 0 | 3 | 7 | 13.55 | 17.8 | | |
| 0383 | 1 | 11 | 12 | 7.17 | | | |
| 0384 | NA | NA | NA | 6.91 | | | |
| 0385 | NA | NA | NA | 7.87 | | | |
| 0386 | 1 | 12 | 13 | 9.2 | | | |
| 0388 | 0 | 12 | 19 | 11.28 | | | |
| 0390 | 1 | 10 | 19 | 15.15 | | | |
| 0391 | 1 | 9 | 12 | 13.62 | | | |
| 0414 | 5; 7 | 4; 3 | 7; 4 | 6.57 | 8 | | |
| 0538 | 1 | 3 | 5 | | 21.9 | | |
| 0540 | 1 | 2 | 4 | | 30.1 | | |
| 0542 | 1 | 3 | 4 | | 33.8 | | |
| 0544 | 1 | 3 | 5 | | 35.5 | | |
| 0546 | 1 | 3 | 4 | | 42.3 | | |
| 0562 | 23 | 4 | 6 | | 2.4 | | |
| 0563 | 9 | 4 | 5 | | 2 | | |
| 0564 | NA | NA | NA | | 35.2 | | |
| 0565 | 18 | 25 | 12 | | 22.7 | | |
| 0567 | 6 | 3 | 4 | | 5.4 | | |
| 0570 | 12 | 3 | 5 | | 3.1 | | |
| 0571 | 13 | 5 | 5 | | 2.1 | | |
| 0572 | 16 | 4 | 5 | | 1.7 | | |
| 0911 | 1 | 5 | 4 | | | | 2.5 |
| 0934 | 1 | 4 | 4 | | | | 3.6 |
| 1070 | 2 | 2 | 3 | | | | |
| 1080 | 1 | 4 | 4 | | | | 1.4 |
| 1081 | 1 | 3 | 4 | | | | 3.5 |
| 1082 | 1 | 4 | 4 | | | | 2 |
| 1083 | 1 | 4 | 4 | | | | 2.1 |

TABLE 7-continued

Competition ELISA, AC-INS Results of the B7-H4 Antibodies and B7-H4xCD3 bispecific Antibodies

| mAb | AC-SINS | DNA | Insulin | COMPETITION ELISA IC50 [nM] | IC50 [nM] | IC50 [nM] | IC50 [nM] |
|---|---|---|---|---|---|---|---|
| 1103 | 1 | 5 | 3 | | | | 1.6 |
| 1113 | 5 | 5 | 3 | | | | 1 |
| 1114 | 4 | 4 | 3 | | | | 0.43 |
| 1115 | 7 | 5 | 3 | | | | 0.42 |
| 1116 | 7 | 8 | 4 | | | | 0.16 |
| 1117 | 6 | 7 | 4 | | | | 0.15 |
| 1124 | 5; 6 | 2; 2 | 3; 2 | | | | |
| 1156 | 4 | 9 | 11 | | | | |
| 1167 | 4; 5 | 13; 11 | 10; 12 | | | | |

Example 6. Differential Scanning Calorimetry (DSC) Analysis

Antibodies were diluted in a phosphate-buffered saline (PBS) solution to 0.6 mg/ml in a volume of 400 μl. PBS was used as a buffer blank in the reference cell. PBS contained 137 mM NaCl, 2.7 mM KCl, 8.1 mM $Na_2HPO_4$, and 1.47 mM $KH_2PO_4$, pH 7.2. Samples were dispensed into the sample tray of a MicroCal VP-Capillary DSC with Autosampler (Malvern Instruments Ltd, Malvern, UK). Samples were equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, MA) was used to fit the data to an MN2-State Model with an appropriate number of transitions. The results of differential scanning calorimetry of optimized anti-B7-H4 binding domains in IgG1 format are shown in Table 8.

TABLE 8

Thermal stability of optimized clones by DSC in the IgG1 mAb format.

| IgG1 mAb name | Tm1 [° C.] | Tm2 [° C.] | Tm3 [° C.] | Apparent Fab Tm [° C.] |
|---|---|---|---|---|
| 0052 | 73.17 ± 0.18 | 76.86 ± 0.03 | 84.19 ± 0.06 | 75.6 |
| 0538 | 72.42 ± 0.23 | 78.56 ± 0.39 | 81.55 ± 0.15 | 76.4 |
| 0540 | 71.89 ± 0.12 | 77.54 ± 0.26 | 80.47 ± 0.10 | 80.5 |
| 0542 | 72.19 ± 0.28 | 77.44 ± 0.59 | 80.46 ± 0.21 | 79.7 |
| 0544 | 72.03 ± 0.10 | 77.35 ± 0.30 | 79.95 ± 0.11 | 79.9 |
| 0546 | 73.17 ± 0.18 | 76.86 ± 0.03 | 84.19 ± 0.06 | 75.6 |
| 0934 | 72.36 ± 0.10 | 77.25 ± 0.03 | 84.57 ± 0.04 | 77.1 |
| 1080 | 71.98 ± 0.12 | 78.49 ± 0.03 | 85.21 ± 012 | 78.4 |
| 1081 | 71.73 ± 0.15 | 79.22 ± 0.02 | 84.83 ± 0.37 | 79.0 |
| 1083 | 73.66 ± 0.21 | 80.94 ± 0.10 | 84.02 ± 0.21 | 71.0 |
| 1103 | 72.91 ± 0.11 | 78.40 ± 0.03 | 84.82 ± 0.07 | 78.1 |
| 0058 | 73.66 ± 0.11 | 76.96 ± 0.04 | 84.11 ± 0.03 | 76.1 |
| 1113 | 71.23 ± 0.02 | 74.9 ± 0.27 | 83.73 ± 0.10 | 71.5 |
| 1114 | 70.86 ± 0.01 | 73.54 ± 0.08 | 83.34 ± 0.05 | 71.0 |
| 1115 | 71.42 ± 0.02 | 74.47 ± 0.18 | 83.55 ± 0.08 | 71.5 |
| 1116 | 67.57 ± 0.02 | 72.32 ± 0.11 | 83.65 ± 0.04 | 68.0 |
| 1117 | 68.76 ± 0.02 | 73.23 ± 0.16 | 83.74 ± 0.05 | 69.0 |

Example 7. Surface Plasmon Resonance (SPR) Analysis of B7-H4 IqG1 mAbs

Anti-B7-H4 clones obtained from hybridoma were assessed in the IgG1 mAb format for binding to human B7-H4 ECD (extra cellular domain) at 25° C. by surface plasmon resonance using a BIACORE™ 8K instrument (GE Healthcare). Anti-human Fc (GE BR-1008-39) was first coated onto a CM5 Sensor Chip following the manufacturer's protocol. The human anti-B7-H4 IgG1 mAbs were run over the chip for 20 sec at 0.75 ug/mL, 50 uL/min in Hank's buffered saline (HBS)-EP+pH=7.4. Next, human B7-H4 ECD at 5 different concentrations at 3-fold dilutions starting from 900 nM (for clones: 7H7, 33G4, 11F12, 33A4, 13F4, 37D4, 19D3, 27C12, 42E2, 28D10, 46E10 and 32F3) and starting from 100 nM (for clones: 29G6 and 47A1) was allowed to associate by running over the chip for 60 sec at 50 uL/min, then dissociate for 300 sec. Binding affinities and rate constants were determined by fitting the resulting sensorgram data to a 1:1 Langmuir model in BIACORE™ T200 Evaluation software version 3.0 (GE Healthcare). The chip was regenerated between each run with 3×3 M $MgCl_2$. Results are shown in Table 9-A.

TABLE 9-A

Kinetics of binding of hybridoma clones in IgG1 format to human B7-H4 ECD by SPR at 25° C.

| Antibody | Hu B7-H4 ECD $K_D$ (nM) | Hu B7-H4 ECD $k_a$ (1/Ms) | Hu B7-H4 ECD $k_d$ (1/s) |
|---|---|---|---|
| 0047 | 3.79 ± 0.20 | 1.68E+05 ± 4.06E+03 | 6.35E−04 ± 2.42E−05 |
| 0048 | 0.83 ± 0.08 | 7.45E+05 ± 1.50E+04 | 6.19E−04 ± 5.10E−05 |
| 0049 | 1.85 ± 0.24 | 2.25E+05 ± 8.50E+03 | 4.14E−04 ± 3.80E−05 |
| 0050 | 8.80 ± 0.44 | 7.61E+04 ± 5.00E+01 | 6.70E−04 ± 3.35E−05 |
| 0051 | 0.57 ± 0.04 | 8.14E+05 ± 2.15E+04 | 4.64E−04 ± 1.95E−05 |
| 0052 | 7.83 ± 0.31 | 1.40E+05 ± 3.50E+03 | 1.10E−03 ± 1.50E−05 |
| 0053 | 0.74 ± 0.05 | 4.34E+05 ± 1.50E+04 | 3.21E−04 ± 3.19E−05 |
| 0055 | 1.90 ± 0.00 | 3.82E+05 ± 5.00E+02 | 7.25E−04 ± 5.00E−07 |
| 0056 | 0.62 ± 0.00 | 5.74E+05 ± 4.50E+03 | 3.53E−04 ± 4.00E−06 |
| 0057 | 7.92 ± 0.48 | 6.41E+04 ± 2.00E+02 | 5.08E−04 ± 2.90E−05 |
| 0058 | 2.83 ± 0.11 | 2.06E+05 ± 2.00E+03 | 5.83E−04 ± 1.70E−05 |
| 0059 | 0.68 ± 0.04 | 5.68E+05 ± 4.78E+03 | 3.89E−04 ± 2.05E−05 |
| 0060 | 1.35 ± 0.08 | 5.58E+05 ± 1.15E+04 | 7.50E−04 ± 2.70E−05 |
| 0061 | 0.84 ± 0.02 | 6.78E+05 ± 7.00E+03 | 5.72E−04 ± 1.00E−05 |

Optimized anti-B7-H4 antibodies and the corresponding parental antibodies in the IgG1 mAb format were tested for binding to human B7-H4 ECD at 37° C. by surface plasmon resonance using a BIACORE™ 8K instrument (GE Healthcare). Anti-human Fc (GE BR-1008-39) was first coated onto a CM5 Sensor Chip following the manufacturer's protocol. The human anti-B7-H4 IgG1 mAbs were run over the chip for 30 sec at 0.75 ug/mL, 50 uL/min in Hank's buffered saline (HBS)-EP+pH=7.4. Next, human B7-H4 ECD at 5 different concentrations at 3-fold dilutions starting from 300 nM was allowed to associate by running over the chip for 65 sec at 50 uL/min, then dissociate for 600 sec. Binding affinities and rate constants were determined by fitting the resulting sensorgram data to a 1:1 Langmuir model in BIACORE™ T200 Evaluation software version 3.0 (GE Healthcare). The chip was regenerated between each run with 3×3 M $MgCl_2$ for 30 sec at 50 uL/min. Results are shown in Table 9-B.

TABLE 9-B

Kinetics of binding of parental and optimized antibodies in IgG1 format to human B7-H4 ECD by SPR at 37° C.

| Antibody name | $K_a$ (1/Ms) | $K_d$ (1/s) | $K_D$ (nM) |
|---|---|---|---|
| 0052 | 4.67E+05 | 5.65E−03 | 12.1 ± 0.6 |
| 0934 | 4.54E+05 | 5.39E−03 | 11.85 ± 0.34 |
| 1080 | 3.92E+05 | 5.40E−03 | 13.78 ± 0.61 |
| 1081 | 2.88E+05 | 9.62E−03 | 33.4 ± 1.6 |
| 1083 | 3.81E+05 | 8.60E−03 | 22.65 ± 0.65 |
| 1103 | 4.62E+05 | 5.29E−03 | 11.5 ± 0.5 |
| 0058 | 6.45E+05 | 1.13E−03 | 1.75 ± 0.04 |
| 1113 | 2.51E+05 | 1.08E−03 | 4.31 ± 0.13 |
| 1114 | 1.95E+05 | 5.59E−04 | 2.87 ± 0.16 |
| 1115 | 4.43E+05 | 1.16E−03 | 2.62 ± 0.1 |
| 1116 | 6.12E+05 | 1.26E−03 | 2.05 ± 0.05 |
| 1117 | 6.20E+05 | 9.49E−04 | 1.54 ± 0.08 |

Optimized anti-B7-H4 antibodies and the corresponding parental antibodies in the IgG1 mAb format were tested for cross-reactivity to cyno and mouse B7-H4 ECD at 37° C. by surface plasmon resonance using a BIACORE™ 8K instrument (GE Healthcare). Anti-human Fc (GE BR-1008-39) was first coated onto a CM5 Sensor Chip following the manufacturer's protocol. The human anti-B7-H4 IgG1 mAbs were run over the chip for 30 sec at 0.75 ug/mL, 50 uL/min in Hank's buffered saline (HBS)-EP+pH=7.4. Next, cyno and mouse B7-H4 ECD at 5 different concentrations at 3-fold dilutions starting from 900 nM was allowed to associate by running over the chip for 65 sec at 50 uL/min, then dissociate for 600 sec. Binding affinities and rate constants were determined by fitting the resulting sensorgram data to a 1:1 Langmuir model in BIACORE™ T200 Evaluation software version 3.0 (GE Healthcare). The chip was regenerated between each run with 3×3 M $MgCl_2$ for 30 sec at 50 uL/min. Results are shown in Table 9-C.

TABLE 9-C

Kinetics of binding of parental and optimized antibodies in IgG1 format to cyno and mouse B7-H4 ECD by SPR at 37° C.

| Antigen | mAb name | $K_a$ (1/Ms) | $K_d$ (1/s) | $K_D$ (nM) |
|---|---|---|---|---|
| cyB7-H4 ECD | 0052 | 1.39E+05 | 4.24E−03 | 30.7 ± 2 |
| muB7-H4 ECD | | 1.43E+05 | 1.26E−01 | 883 ± 22 |
| cyB7-H4 ECD | 1103 | 1.56E+05 | 4.09E−03 | 26.15 ± 0.65 |
| muB7-H4 ECD | | 1.63E+05 | 1.95E−01 | 1195 ± 25 |
| cyB7-H4 ECD | 0058 | 1.54E+05 | 3.68E−03 | 23.85 ± 0.35 |
| muB7-H4 ECD | | | weak | |
| cyB7-H4 ECD | 1114 | 5.67E+04 | 1.08E−03 | 19.05 ± 0.15 |
| muB7-H4 ECD | | | weak | |

Example 8: Surface Plasmon Resonance (SPR) Analysis of B7-H4×CD3 Bispecific Antibodies The binding affinities of B7-H4×CD3 bispecific antibodies of parental hybridoma clones to human, cyno and mouse B7-H4 ECD were determined using a BIACORE™ T200 instrument (GE Healthcare) at 25° C. or 37° C. with a collection rate of 10 Hz. Anti-human Fc (GE BR-1008-39) was first coated onto a CM5 Sensor Chip following the manufacturer's protocol. The B7-H4-CD3 IgG2 EEE/RRR bispecific antibodies were run over the chip for 20-25 sec at 0.5 ug/mL, 50 uL/min in Hank's buffered saline (HBS)-EP+ pH=7.4. Human, cyno and mouse B7-H4 ECD were allowed to associate by running over the chip for 65 sec at 50 uL/min, then dissociate for 300 sec. 5 different concentrations of the antigens at 3-fold dilutions were used starting from 400 nM for cyno and starting from 900 nM for human and mouse antigens. The dissociation was monitored for 600 seconds and the surface was regenerated 3 times with 3 M $MgCl_2$ for 30 sec at 50 uL/min. Binding affinities and rate constants were determined by fitting the resulting sensorgram data to a 1:1 Langmuir model in BIACORE™ T200 Evaluation software version 3.0 (GE Healthcare). Results are shown in Table 10-A.

TABLE 10-A

Kinetics of binding of parental bispecific antibodies to human, cyno mouse and B7-H4 ECD by SPR at 25° C. or 37° C.

| Antigen | Ab name | T (° C.) | $k_a$ (1/MS) | $k_d$ (1/s) | $K_D$ (nM) |
|---|---|---|---|---|---|
| cyB7-H4 | 0068 | 25 | 1.19E+05 ± 1.31E+02 | 1.15E−03 ± 6.37E−06 | 9.64 ± 0.06 |
| huB7-H4 | 0068 | 25 | 3.38E+05 ± 4.29E+04 | 6.78E−04 ± 2.64E−05 | 2.05 ± 0.34 |
| muB7-H4 | 0068 | 25 | NA | NA | NA |
| cyB7-H4 | 0068 | 37 | 1.83E+05 ± 3.89E+03 | 5.19E−03 ± 1.59E−05 | 28.33 ± 0.51 |
| huB7-H4 | 0068 | 37 | 5.58E+05 ± 4.23E+03 | 2.15E−03 ± 6.37E−05 | 3.85 ± 0.09 |
| cyB7-H4 | 0074 | 25 | 1.29E+05 ± 2.86E+03 | 1.20E−03 ± 8.70E−06 | 9.29 ± 0.22 |
| huB7-H4 | 0074 | 25 | 1.76E+05 ± 6.64E+03 | 1.20E−03 ± 1.09E−05 | 6.83 ± 0.30 |
| muB7-H4 | 0074 | 25 | 1.00E+5 ± 5.24E+3 | 2.99E−2 ± 1.18E−3 | 299.21 ± 9.48 |
| cyB7-H4 | 0074 | 37 | 1.88E+05 ± 9.18E+03 | 5.81E−03 ± 4.80E−05 | 30.88 ± 1.33 |
| huB7-H4 | 0074 | 37 | 2.75E+05 ± 4.44E+03 | 6.02E−03 ± 6.00E−05 | 21.91 ± 0.58 |
| cyB7-H4 | 0077 | 25 | 7.66E+04 ± 6.39E+02 | 7.57E−04 ± 4.54E−06 | 9.88 ± 0.14 |
| huB7-H4 | 0077 | 25 | 1.25E+05 ± 1.42E+04 | 7.75E−04 ± 2.93E−05 | 6.33 ± 0.96 |
| muB7-H4 | 0077 | 25 | 8.23E+4 ± 1.86E+3 | 4.83E−2 ± 3.27E−3 | 587.74 ± 53.05 |
| cyB7-H4 | 0077 | 37 | 1.07E+05 ± 5.48E+03 | 3.32E−03 ± 2.05E−05 | 31.05 ± 1.78 |
| huB7-H4 | 0077 | 37 | 1.83E+05 ± 2.63E+03 | 3.41E−03 ± 1.18E−04 | 18.69 ± 0.38 |
| cyB7-H4 | 0080 | 25 | 1.57E+05 ± 2.35E+03 | 6.76E−04 ± 7.94E−06 | 4.29 ± 0.11 |
| huB7-H4 | 0080 | 25 | 2.96E+05 ± 3.85E+04 | 6.92E−04 ± 2.70E−05 | 2.39 ± 0.40 |

TABLE 10-A-continued

Kinetics of binding of parental bispecific antibodies to human, cyno mouse and B7-H4 ECD by SPR at 25° C. or 37° C.

| Antigen | Ab name | T (° C.) | $k_a$ (1/MS) | $k_d$ (1/s) | $K_D$ (nM) |
|---|---|---|---|---|---|
| muB7-H4 | 0080 | 25 | 1.89E+5 ± 1.60E+4 | 1.38E−2 ± 2.18E−3 | 74.80 ± 17.88 |
| cyB7-H4 | 0080 | 37 | 2.20E+05 ± 7.99E+03 | 2.82E−03 ± 4.39E−05 | 12.81 ± 0.66 |
| huB7-H4 | 0080 | 37 | 4.65E+05 ± 6.89E+03 | 2.83E−03 ± 8.89E−05 | 6.08 ± 0.10 |

The binding affinities of B7-H4×CD3 bispecific antibodies of parental hybridoma clones to human and cyno CD3 were determined using a BIACORE™ T200 instrument (GE Healthcare) at 25° C. with a collection rate of 10 Hz. Anti-His (GE 10260125) was first coated onto a CM5 Sensor Chip following the manufacturer's protocol. Human CD3 (delta/epsilon heterodimer) were run over the chip for 30 sec at 0.50 ug/mL, 10 uL/min in Hank's buffered saline (HBS)-EP+pH=7.4. A three-fold dilution series of B7-H4×CD3 bispecific protein with concentrations ranging from 150 nM to 5.6 nM was injected over the sensor surface for 72 seconds at a flow rate of 50 µl/min. The dissociation was monitored for 300 seconds and the surface was regenerated with 10 mM Glycine pH 1.5 for 20 sec at 50 uL/min. Binding affinities and rate constants were determined by fitting the resulting sensorgram data to a 1:1 Langmuir model in BIACORE™ T200 Evaluation software version 3.0 (GE Healthcare). Results are shown in Table 10-B.

TABLE 10-B

Binding kinetics of B7-H4 × CD3 bispecific antibodies of parental hybridoma clones to human and cyno CD3 by SPR at 25° C.

| Ab name | Anti-B7-H4 Clone | Antigen | $k_a$ (1/MS) | $k_d$ (1/s) | $K_D$ (nM) |
|---|---|---|---|---|---|
| 0068 | 37D4 | huCD3 | 4.20E+05 ± 2.58E+04 | 5.53E−03 ± 8.30E−05 | 13.22 ± 0.97 |
| 0074 | 28D10 | huCD3 | 7.58E+05 ± 1.13E+04 | 5.59E−03 ± 1.92E−05 | 7.38 ± 0.13 |
| 0077 | 19D3 | huCD3 | 4.23E+05 ± 2.26E+04 | 5.36E−03 ± 7.81E−05 | 12.70 ± 0.84 |
| 0080 | 7H7 | huCD3 | 4.11E+05 ± 1.27E+04 | 5.21E−03 ± 2.65E−05 | 12.69 ± 0.42 |
| 0068 | 37D4 | cyCD3 | 3.74E+05 ± 8.83E+03 | 5.06E−03 ± 3.75E−05 | 13.52 ± 0.41 |
| 0074 | 28D10 | cyCD3 | 6.42E+05 ± 1.42E+04 | 5.34E−03 ± 4.31E−06 | 8.33 ± 0.19 |
| 0077 | 19D3 | cyCD3 | 3.69E+05 ± 7.34E+03 | 5.04E−03 ± 8.12E−05 | 13.67 ± 0.47 |
| 0080 | 7H7 | cyCD3 | 3.72E+05 ± 8.13E+03 | 4.93E−03 ± 3.85E−05 | 13.27 ± 0.37 |

The binding affinities of B7-H4×CD3 bispecific antibodies to human, cyno and murine B7-H4 ECD were determined using a BIACORE™ T200 instrument (GE Healthcare) at 37° C. with a collection rate of 10 Hz. Anti-human Fc (GE BR-1008-39) was first coated onto a CM5 Sensor Chip following the manufacturer's protocol. The B7-H4×CD3 IgG2 EEE/RRR bispecific antibodies were run over the chip for 30 sec at 0.75 ug/mL, 50 uL/min in Hank's buffered saline (HBS)-EP+pH=7.4. Human, cyno, mouse and rat B7-H4 ECD were allowed to associate by running over the chip for 60 sec at 50 uL/min, then dissociate for 300 sec. 5 different concentrations of the antigens at 3-fold dilutions were used starting from 270 nM for human and cyno and starting from 2100 nM for rat and mouse antigens. The dissociation was monitored for 600 seconds and the surface was regenerated 3 times with 3 M MgCl2 for 30 sec at 50 uL/min. Binding affinities and rate constants were determined by fitting the resulting sensorgram data to a 1:1 Langmuir model in BIACORE™ T200 Evaluation software version 3.0 (GE Healthcare). Results are shown in Table 10-C.

TABLE 10-C

Kinetics of binding of parental and optimized bispecific antibodies to human, cyno, rat and mouse B7-H4 ECD by SPR at 37° C.

| Antigen | Ab name | ka (1/Ms) | kd (1/s) | $K_D$ (nM) |
|---|---|---|---|---|
| cyB7-H4 ECD | 0068 | 6.31E+05 | 4.15E−03 | 6.58 ± 0.11 |
| huB7-H4 ECD | 0068 | 8.81E+05 | 1.53E−03 | 1.74 ± 0.02 |
| muB7-H4 ECD | 0068 | NA | NA | NA |
| ratB7-H4 ECD | 0068 | NA | NA | NA |
| cyB7-H4 ECD | 0074 | 5.53E+05 | 4.87E−03 | 8.81 ± 0.25 |
| huB7-H4 ECD | 0074 | 5.75E+05 | 5.09E−03 | 8.86 ± 0.03 |
| muB7-H4 ECD | 0074 | 1.73E+05 | 1.34E−01 | 776.5 ± 39.5 |
| ratB7-H4 ECD | 0074 | 1.17E+05 | 1.31E−01 | 1125 ± 115 |
| cyB7-H4 ECD | 1156 | 6.17E+05 | 4.63E−03 | 7.53 ± 0.29 |
| huB7-H4 ECD | 1156 | 6.15E+05 | 4.78E−03 | 7.78 ± 0.1 |
| muB7-H4 ECD | 1156 | 1.77E+05 | 1.96E−01 | 1110 ± 70 |
| ratB7-H4 ECD | 1156 | 1.12E+05 | 2.04E−01 | 1840 ± 260 |

TABLE 10-C-continued

Kinetics of binding of parental and optimized bispecific antibodies to human, cyno, rat and mouse B7-H4 ECD by SPR at 37° C.

| Antigen | Ab name | ka (1/Ms) | kd (1/s) | $K_D$ (nM) |
|---|---|---|---|---|
| cyB7-H4 ECD-1 | 1167 | 2.02E+05 | 1.33E−03 | 6.6 ± 0.03 |
| huB7-H4 ECD-1 | 1167 | 2.86E+05 | 9.20E−04 | 3.22 ± 0.11 |
| muB7-H4 ECD | 1167 | NA | NA | NA |
| ratB7-H4 ECD | 1167 | NA | NA | NA |

The binding affinities of B7-H4-CD3 bispecific antibodies to human and cyno CD3 were determined using a BIACORE™ T200 instrument (GE Healthcare) at 37° C. with a collection rate of 10 Hz. Anti-His (GE 10260125) was first coated onto a CM5 Sensor Chip following the manufacturer's protocol. Human and cyno CD3 (delta/epsilon heterodimer) were run over the chip for 36 sec at 0.50 ug/mL, 10 uL/min in Hank's buffered saline (HBS)-EP+pH=7.4. A three-fold dilution series of B7-H4-CD3 bispecific protein with concentrations ranging from 300 nM to 3.7 nM was injected over the sensor surface for 72 seconds at a flow rate of 50 μl/min. The dissociation was monitored for 200 seconds and the surface was regenerated with 10 mM Glycine pH 1.5 for 20 sec at 50 uL/min. Binding affinities and rate constants were determined by fitting the resulting sensorgram data to a 1:1 Langmuir model in BIACORE™ T200 Evaluation software version 3.0 (GE Healthcare). Results are shown in Table 10-D.

TABLE 10-D

Binding kinetics of B7-H4-CD3 bispecific antibodies to human and cyno CD3 by SPR at 37° C.

| Antigen | Ab name | ka (1/Ms) | kd (1/s) | $K_D$ (nM) |
|---|---|---|---|---|
| cyCD3 | 0068 | 5.06E+05 | 3.49E−02 | 68.95 ± 0.05 |
| huCD3 | 0068 | 5.54E+05 | 3.49E−02 | 63 ± 0.3 |
| cyCD3 | 0074 | 5.07E+05 | 2.39E−02 | 47.15 ± 1.45 |
| huCD3 | 0074 | 5.58E+05 | 2.34E−02 | 41.85 ± 1.45 |
| cyCD3 | 1156 | 4.96E+05 | 4.87E−03 | 68.85 ± 0.45 |
| huCD3 | 1156 | 5.43E+05 | 5.09E−03 | 62.4 ± 1.4 |
| cyCD3 | 1167 | 5.06E+05 | 1.34E−01 | 66.75 ± 1.35 |
| huCD3 | 1167 | 5.31E+05 | 1.31E−01 | 63.5 ± 3.2 |

The comparison of binding affinities of CD3-B7-H4×CD3 bispecific antibodies to human B7-H4 and CD3 when the bispecific antibodies were produced from transient expi293 or stable CHO cells was done using a BIACORE™ T200 instrument (GE Healthcare) at 37° C. with a collection rate of 10 Hz. To test binding of B7-H4 similar experiment was performed as described above but the B7-H4-CD3 IgG2 EEE/RRR bispecific antibodies were run over the chip for 36 sec at 0.5 ug/mL, 50 uL/min and human B7-H4 ECD was allowed to associate by running over the chip for 72 sec at 50 uL/min, then dissociate for 200 sec. Same set of concentrations was used. To test binding of CD3 similar experiment was performed as described above with the same parameters. Results are shown in Table 10-E.

TABLE 10-E

Kinetics of binding of optimized bispecific antibodies derived from transient expression in expi293 or stable expression in CHO tested by SPR at 37° C.

| Antigen | Antibody name | $k_a$ (1/Ms) | $k_d$ (1/s) | $K_D$ (nM) |
|---|---|---|---|---|
| cyB7-H4 | 1167-CHO | 6.47E+04 | 1.88E−03 | 28.95 ± 1.65 |
| cyB7-H4 | 1167-HEK | 6.40E+04 | 1.86E−03 | 29.1 ± 1.1 |
| huB7-H4 | 1167-CHO | 1.44E+05 | 1.38E−03 | 9.66 ± 0.84 |
| huB7-H4 | 1167-HEK | 1.36E+05 | 1.24E−03 | 9.15 ± 0.27 |
| cyCD3 | 1167-CHO | 5.19E+05 | 3.05E−02 | 58.8 ± 0.7 |
| cyCD3 | 1167-HEK | 4.49E+05 | 3.17E−02 | 70.75 ± 3.15 |
| huCD3 | 1167-CHO | 6.38E+05 | 3.17E−02 | 49.75 ± 2.05 |
| huCD3 | 1167-HEK | 4.99E+05 | 3.09E−02 | 62.5 ± 5.7 |

A comparison of binding affinities of CD3-B7-H4×CD3 bispecific antibodies to human B7-H4 and CD3 for bispecifics containing various CD3 variants was done using a BIACORE™ T200 instrument (GE Healthcare) at 37° C. with a collection rate of 10 Hz. To test binding of CD3 similar experiment was performed as described above with the following changes. A three-fold dilution series of B7-H4-CD3 bispecific protein with concentrations ranging from 900 nM to 3.7 nM was injected over the sensor surface for 60 seconds at a flow rate of 50 μl/min. Binding affinities and rate constants were determined by fitting the resulting sensorgram data to a 1:1 Langmuir model in BIACORE™ T200 Evaluation software version 3.0 (GE Healthcare). Results are shown in Table 10-F.

TABLE 10-F

Kinetics of binding of bispecific antibodies with different CD3 variants to human CD3 tested by SPR at 37° C.

| Antibody name | CD3 variant | $k_a$ (1/Ms) | $k_d$ (1/s) | $K_D$ (nM) |
|---|---|---|---|---|
| 0074 | 2B5v6 | 5.92E+05 ± 3.20E+04 | 3.36E−02 ± 7.00E−04 | 56.90 ± 1.90 |
| 0087 | 2B5v598 | 2.05E+05 ±+ 2.00E+03 | 2.54E−02 ± 8.00E−04 | 124.00 ± 3.00 |
| 0088 | 2B5c707 | 5.11E+05 ± 5.50E+03 | 6.89E−02 ± 1.55E−03 | 134.50 ± 1.50 |

A comparison of binding affinities of CD3-B7-H4×CD3 bispecific antibodies to human B7-H4 and CD3 for bispecifics based on IgG2 or IgG1 EEE/RRR scaffolds was done using a BIACORE™ T200 instrument (GE Healthcare) at 37° C. with a collection rate of 10 Hz. To test binding of B7-H4 similar experiment was performed as described above but the B7-H4-CD3 IgG2 EEE/RRR bispecific antibodies were run over the chip for 40 sec at 0.75 ug/mL, 10 uL/min and human B7-H4 ECD was allowed to associate by running over the chip for 65 sec at 50 uL/min, then dissociate for 600 sec. Concentrations in the range of 300 nM to 11 nM were used. To test binding of CD3 similar experiment was performed as described above with the following changes. A three-fold dilution series of B7-H4-CD3 bispecific protein with concentrations ranging from 900 nM to 3.7 nM was injected over the sensor surface for 60 seconds at a flow rate of 50 μl/min. Binding affinities and rate constants were determined by fitting the resulting sensorgram data to a 1:1 Langmuir model in BIACORE™ T200 Evaluation software version 3.0 (GE Healthcare). Results are shown in Table 10-G.

TABLE 10-G

Kinetics of binding of bispecific antibodies tested by SPR at 37° C.

| Antigen | Ab name | Bispecific scaffold | $k_a$ (1/Ms) | $k_d$ (1/s) | $K_D$ (nM) |
|---|---|---|---|---|---|
| huB7-H4 ECD | 0074 | IgG2 | 3.19E+05 | 5.82E−03 | 18.24 |
| huB7-H4 ECD | 0089 | IgG1 | 2.64E+5 ± 8.52E+3 | 5.88E−3 ± 1.10E−5 | 22.33 ± 0.76 |
| huCD3 | 0074 | IgG2 | 5.92E+05 ± 3.20E+04 | 3.36E−02 ± 7.00E−04 | 56.90 ± 1.90 |
| huCD3 | 0089 | IgG1 | 6.53E+05 ± 2.45E+04 | 2.60E−02 ± 1.00E−04 | 39.95 ± 1.65 |

Example 9. Cell-Based Binding of Antibodies to B7-H4 and CD3

Cell-based binding was performed for B7-H4×CD3 bispecific molecules. Twelve step serial dilutions starting with 700 nM concentration of B7-H4×CD3 bispecific molecules were incubated with multiple human B7-H4 expressing cell lines including MX1, HCC1954-Luc, T47D, and HEK293-huB7-H4, cynomolgus B7-H4 expressing cell line CHO-cyB7-H4, and mouse B7-H4 expressing cell-line HEK293-msB7-H4.

In addition, binding was performed with CD3 expressing primary human T cells isolated from healthy donor PBMCs, and CD3 expressing cells isolated from cynomologus PBMCs, as well as, CD3 expressing cells from rat spleens and C57 and BalbC mouse spleen. Human Pan T cells were isolated from PBMCs by negative selection using a T cell enrichment kit (StemCell Technologies). Rat and mouse spleens were processed via mechanical homogenization, red blood lysis (Roche) and filtration steps.

All cells were washed twice with Flow Buffer containing 1% BSA (Fisher Scientific) and 0.01% Sodium Azide (Ricca Chemical Company) in DPBS (Gibco) and seeded at 100K cells per well density in Flow buffer. All centrifugation steps were carried out at 300 g for 5 minutes.

The incubation was done at 37° C. for 2 hours with sodium azide functioning to inhibit antibody internalization. Unbound B7-H4×CD3 bispecific molecules were washed off in two rounds of 37° C. Flow buffer washes/centrifugation steps. Bound B7-H4×CD3 bispecific molecules were detected with PE-labeled goat anti-human Fcγ secondary antibody (Jackson Immuno Research). Secondary antibody incubation was carried out at 1:200 dilution at 37° C. for 30 minutes. Unbound secondary antibody was washed off in two rounds of 37° C. Flow buffer washes/centrifugation steps. Cells were resuspended in 7-AAD Viability Staining solution (Bio Legend) containing Flow buffer and data acquired on Flow Cytometer. The measured EC50 of binding saturation are listed in Table 11-A and Table 11-B below. On the cell, bispecific antibody 1167 binds to human B7-H4 with higher affinity than human CD3, it binds cynomolgus B7-H4 with comparable affinity to human B7-H4 and does not bind murine or rat B7-H4.

Negative cell lines with no B7-H4 (or CD3) expression including HCC1806-Luc, HEK293, and CHO cells showed no binding.

TABLE 11-A

B7-H4xCD3 Bispecific Antibodies Binding to B7-H4 Expressing Cell Lines

| Antibody | MX-1 EC50 (nM) | HCC1954-luc EC50 (nM) | T47D EC50 (nM) | HEK293-huB7-H4 EC50 (nM) | CHO-cynoB7-H4 EC50 (nM) |
|---|---|---|---|---|---|
| 1156 | 10.03 | 10.42 | 4.61 | 4.19 | 5.66 |
| 1167 | 35.29 | 36.6 | 5.05 | 4.65 | 24.6 |
| 1037 | 3.64 | | | | |
| 1133 | 1.47 | | | | |
| 1134 | 17.55 | | | | |
| 1136 | 3.55 | | | | |
| 1168 | 13.06 | | | | |
| 1169 | 10.01 | | | | |
| 1170 | 6.88 | | | | |
| 0999 | 3.9 | | | | |

TABLE 11-B

B7-H4 × CD3 Bispecific Antibodies Binding to CD3 Expressing Cell Lines

| Antibody | Human T Cell EC50 (nM) | Cyno PBMC EC50 (nM) |
|---|---|---|
| 1156 | 44.76 | 26.99 |
| 1167 | 64.05 | 46.03 |
| 1037 | 5.78 | |
| 1133 | 5.73 | |
| 1134 | 6.90 | |
| 1136 | 5.70 | |
| 1168 | 5.56 | |
| 1169 | 5.22 | |
| 1170 | 5.51 | |
| 0999 | 9.77 | |

Example 10. T Cell Mediated Cell Killing Activity of Optimized CD3-B7-H4×CD3 Bispecific Antibodies Human PBMCs were isolated from healthy donor blood using Ficoll Paque (GE Healthcare). Pan T cells were isolated from PBMCs using a T cell enrichment kit from Stem Cell Technologies (negative selection of T cells). B7-H4 expressing human tumor cells transfected with a luciferase expression construct, HCC1954-Luc, OVCAR3-

Luc or HCT116-Luc, were resuspended in R10 medium (RPMI, 10% FBS, 1% Penn/Strep, 3 ml of 45% glucose). T cells were also resuspended in R10 media and added to tumor cells at an Effector to Target ratio (E:T ratio) either 5:1 or 2.5:1. The cells were treated with serial dilutions of B7-H4×CD3 bispecific antibodies or a negative control CD3 bispecific, spun down at 250×g for four minutes to initiate contact and incubated at 37° C. for 48 hours.

For luciferase assay, the luciferase signal was measured using the neolite reagent (Perkin Elmer) using a Victor (Perkin Elmer). $EC_{50}$ values were calculated in Graphpad PRISM using four parameter non-linear regression analysis.

For the lactate dehydrogenase (LDH) assay, the LDH released from compromised target cells using the a Cytotox 96 Non-Radioactive Cytotoxicity assay kit (Promega, G1780) and Victor microplate reader (Perkin Elmer). $EC_{50}$ values were calculated in Graphpad PRISM using four parameter non-linear regression analysis.

The results are shown in Table 12. These results demonstrate that B7-H4×CD3 bispecific antibodies redirected cytotoxic T cell killing of various cell lines that express human B7-H4 in vitro. These cell lines include breast cancer cell lines of HR+HER2−, HER2+, and TNBC subtype, in addition to ovarian cancer cell line. In addition, antibodies 1156 and 1167 have been shown to be cross reactive in cynomolgus monkeys as well.

Example 11. In Vivo Evaluation of B7-H4×CD3 Bispecific Antibody Mediated Activity-Adoptive Transfer or PBMC Model Human PBMCs were thawed into media X-VIVO 15 (Lonza) containing 5% human serum albumin (Gemini #100-318), 1% Penn/Strep, 0.01 mM 2-mercaptoethanol supplemented with serum-free PBMC thawing solution (CTL #AA-005) at approximately 10 million cells per ml. Cells were spun down after 5 minutes incubation at room temperature and resuspended in Robosep buffer (Stem Cell Technologies) at a concentration of 50 million cells per ml. T cells were isolated using the EasySep human T cell enrichment kit (Stem cell technologies). T cells were activated and expanded using a Human T cell activation/Expansion kit (Miltenyi). On day 2, T cells were transferred to a G-Rex cell culture device for expansion, and IL-2 (Stem Cell Technologies) was added to the media and replenished after 3 days. T cells were harvested 1 week after activation/expansion. At the time of harvest, beads were removed with a magnet, and cells were resuspended in DPBS at 1×107 or 1.5×107 cells/mL for in vivo inoculation.

For xenograft studies, NSG mice were inoculated with either breast cancer cell lines (MDA-MB468, HCC1954, MX1-Luc, ZR75-1, and T47D) or patient derived xenograft (PDX-BRX-11380, PDX-BRX-12351, PDX-BRX-24301, PDX-BRX-24305, PDX-BRX-26302, PDX-BRX-26305,

TABLE 12

T Cell Mediated Tumor Cell Killing Activity of Bispecific Antibodies

| Antibody | HCC1954-Luc EC50 (nM) | MX-1 | MDA-MB-468 | T47D | MDA-MB-453 | OVCAR3-Luc | 293-hB7-H4 | CHO-cyB7-H4 |
|---|---|---|---|---|---|---|---|---|
| 0974 | 764 | | | | | | | |
| 0976 | 2167 | | | | | | | |
| 0978 | 320 | | | | | | | |
| 0980 | 390 | | | | | | | |
| 0982 | 2650 | | | | | | | |
| 0998 | 410 | | | | | | | |
| 0999 | 277 | | | 258 | | 90 | | |
| 1000 | 100 | | | | | | | |
| 1001 | 10 | | | | | | | |
| 1003 | 100 | | | | | | | |
| 1037 | 620 | | | 1266 | | Ambiguous | | |
| 1130 | 73700 | | | | | 810 | | |
| 1133 | 790 | | | 2811 | | Ambiguous | | |
| 1134 | 1560 | | | 7333 | | 540 | | |
| 1135 | 1200 | | | | | 420 | | |
| 1136 | 500 | | | 3823 | | Ambiguous | | |
| 1156 | 632 | 46 | 194 | 1305 | 11068 | Ambiguous | 56 | 23 |
| 1161 | No kill | | | | | No kill | | |
| 1162 | No kill | | | | | No kill | | |
| 1163 | No kill | | | | | No kill | | |
| 1166 | 15500 | | | | | 800 | | |
| 1167 | 1004 | 62 | 806 | 814 | 11764 | 240 | 49 | 235 |
| 1168 | 2165 | | | 1907 | | 360 | | |
| 1169 | 975 | | | 818 | | 190 | | |
| 1170 | 595 | | | 444 | | 130 | | |
| 0077 | 93 | | | | | | | |
| 0080 | 36 | | | | | | | |
| 0074 | 73 | 3.5 | 42 | 224 | 286 | 31 | | |
| 0068 | 284 | 17 | 332 | 566 | 1234 | 79 | | |
| 0089 | 75 | | 45 | | | | | |
| 0090 | 68 | | | | | | | |
| 0092 | 593 | | 49 | | | | | |
| 0094 | 15 | | 1 | | | | | |
| 0095 | 21 | | 1 | | | | | |
| 0087 | 57 | | 109 | | | | | |
| 0088 | 140 | | 655 | | | | | |

PDX-BRX-26360, PDX-OVX-24409) fragments subcutaneously in the flank. Tumor measurements were collected using a digital Vernier caliper, and volumes were calculated by use of the modified ellipsoid formula ½×length×width2. Mice were randomized and staged at tumor size of 200-400 mm³.

For human PBMC engraftment experiments ("PMBC model"), 5 million human PBMCs were injected intravenously 6 days prior to first dose.

For human T cell adoptive transfer experiments, 2.5 million cultured human T cells were inoculated one day after first dose. Mice were dosed with B7-H4×CD3 bispecific molecules or controls in 0.2 mL bolus injection weekly up to 3 times.

Tumor measurements were collected twice weekly along with continuous monitoring for signs of a graft versus host response. All B7-H4×CD3 bispecific molecules showed dose dependent T cell mediated anti-tumor activity in both cell line xenograft and patient derived xenograft models. Below tables show the dose, tumor volume, SEM (standard error of mean) and percent tumor growth inhibition (TGI) of the various experiments carried out herein.

The results are described in below Tables 13 A through N. These results demonstrate B7-H4×CD3 bispecific antibodies dose-dependently induced tumoricital activity with both intravenous and subcutaneous dosing in human cell-line xenograft and patient-derived xenograft models of breast cancer in vivo. These models include breast cancer of HR+HER2−, HER2+, and TNBC molecular subtypes.

TABLE 13-A

In Vivo Tumor Inhibition PMBC model, with HCC1954 Engraftment, Antibodies 1167 and 1156

| Treatment | Dose (mg/kg) | Route | Day 13 tumor volume (mm³) | SEM (mm³) | tumor growth inhibition (%) |
|---|---|---|---|---|---|
| Vehicle | — | IV | 608 | 14 | — |
| 0086 | 0.5 | IV | 626 | 21 | −3.0 |
| 1167 | 0.5 | IV | 160 | 12 | 74 |
| | 0.05 | IV | 238 | 8 | 61 |
| | 0.005 | IV | 266 | 5 | 56 |
| | 0.0015 | IV | 307 | 14 | 50 |
| 1156 | 0.5 | IV | 235 | 9 | 61 |
| | 0.05 | IV | 272 | 18 | 53 |
| | 0.005 | IV | 295 | 9 | 51 |
| | 0.0015 | IV | 294 | 10 | 52 |

TABLE 13-B

In Vivo Tumor Inhibition PMBC model, with HCC1954 Engraftment, Antibodies 0074, 0068 and 0087

| Treatment | Dose (mg/kg) | Route | Day 13 tumor volume (mm³) | SEM (mm³) | tumor growth inhibition (%) |
|---|---|---|---|---|---|
| Vehicle | — | IV | 559 | 11 | — |
| 0074 | 0.5 | IV | 162 | 10 | 71 |
| | 0.05 | IV | 204 | 10 | 64 |
| | 0.005 | IV | 277 | 12 | 51 |
| 0068 | 0.5 | IV | 113 | 4 | 80 |
| | 0.05 | IV | 167 | 12 | 70 |
| 0087 | 0.5 | IV | 257 | 16 | 54 |
| | 0.05 | IV | 317 | 13 | 43 |

TABLE 13-C

In Vivo Tumor Inhibition Adoptive T Cell Transfer model, with HCC1954 Engraftment, Antibodies 0074, 0068 and 0077 and 0080

| Treatment | Dose (mg/kg) | Route | Day 13 tumor volume (mm³) | SEM (mm³) | tumor growth inhibition (%) |
|---|---|---|---|---|---|
| Vehicle | — | IV | 569 | 16 | — |
| 0074 | 1.5 | IV | 235 | 11 | 59 |
| | 0.5 | IV | 257 | 16 | 55 |
| | 0.05 | IV | 322 | 14 | 43 |
| 0080 | 1.5 | IV | 214 | 12 | 62 |
| | 0.5 | IV | 238 | 7 | 58 |
| | 0.05 | IV | 321 | 19 | 44 |
| 0068 | 1.5 | IV | 110 | 9 | 81 |
| | 0.5 | IV | 168 | 12 | 70 |
| | 0.05 | IV | 366 | 15 | 36 |
| 0077 | 0.5 | IV | 249 | 12 | 56 |

TABLE 13-D

In Vivo Tumor Inhibition PMBC model, with MDA-MB-468 Engraftment, Antibodies 0068, 0074, 0086, 1156 and 1167

| Treatment | Dose (mg/kg) | Route | Day 12 tumor volume (mm³) | SEM (mm³) | tumor growth inhibition (%) |
|---|---|---|---|---|---|
| Vehicle | — | IV | 582 | 19 | — |
| 0086 | 0.5 | IV | 619 | 18 | −6.03 |
| 1167 | 3 | IV | 57 | 5 | 84.7 |
| | 0.5 | IV | 54 | 18 | 85.2 |
| | 0.05 | IV | 68 | 6 | 83.0 |
| | 0.005 | IV | 84 | 9 | 80.4 |
| | 0.0015 | IV | 234 | 31 | 56.2 |
| 1156 | 0.5 | IV | 52 | 4 | 85.6 |
| | 0.05 | IV | 80 | 16 | 81.1 |
| | 0.005 | IV | 170 | 27 | 66.5 |
| | 0.0015 | IV | 270 | 15 | 50.3 |
| 0068 | 0.5 | IV | 83 | 24 | 80.5 |
| 0074 | 0.5 | IV | 79 | 8 | 81.3 |

TABLE 13-E

In Vivo Tumor Inhibition PMBC model, with MDA-MB-468 Engraftment, Antibodies 0068, 0074, 0087, and 0088

| Treatment | Dose (mg/kg) | Route | Day 12 tumor volume (mm³) | SEM (mm³) | tumor growth inhibition (%) |
|---|---|---|---|---|---|
| Vehicle | — | IV | 636 | 46 | — |
| 0074 | 0.5 | IV | 107 | 42 | 83.1 |
| | 0.08 | IV | 137 | 10 | 78.5 |
| | 0.025 | IV | 394 | 31 | 38.2 |
| 0087 | 0.5 | IV | 214 | 31 | 66.3 |
| | 0.08 | IV | 447 | 17 | 29.7 |
| | 0.025 | IV | 492 | 15 | 22.6 |
| 0088 | 0.5 | IV | 488 | 41 | 23.2 |
| | 0.08 | IV | 503 | 19 | 21.0 |
| | 0.025 | IV | 568 | 18 | 10.8 |
| 0068 | 0.5 | IV | 56 | 3 | 91.2 |
| | 0.08 | IV | 86 | 9 | 86.5 |
| | 0.025 | IV | 420 | 15 | 34.0 |

TABLE 13-F

In Vivo Tumor Inhibition Adoptive T Cell Transfer Model, with MDA-MB-468 Engraftment, Antibodies 0074, 0087, and 0088

| Treatment | Dose (mg/kg) | Route | Day 13 tumor volume (mm³) | SEM (mm³) | tumor growth inhibition (%) |
|---|---|---|---|---|---|
| Vehicle | — | IV | 684 | 29 | — |
| 0074 | 3 | IV | 464 | 31 | 32.2 |
|  | 1 | IV | 123 | 20 | 82.0 |
|  | 0.08 | IV | 199 | 17 | 70.9 |
|  | 0.025 | IV | 458 | 26 | 33.0 |
| 0087 | 3 | IV | 208 | 39 | 69.6 |
|  | 1 | IV | 136 | 8 | 80.1 |
|  | 0.08 | IV | 417 | 11 | 39.0 |
|  | 0.025 | IV | 433 | 34 | 36.7 |
| 0088 | 3 | IV | 218 | 25 | 68.1 |
|  | 1 | IV | 394 | 14 | 42.4 |
|  | 0.08 | IV | 520 | 17 | 23.9 |
|  | 0.025 | IV | 460 | 13 | 32.7 |

TABLE 13-G

In Vivo Tumor Inhibition Adoptive T Cell Transfer Model, with MDA-MB-468 Engraftment, Antibodies 0074 and 0089

| Treatment | Dose (mg/kg) | Route | Day 12 tumor volume (mm³) | SEM (mm³) | tumor growth inhibition (%) |
|---|---|---|---|---|---|
| Vehicle | — | IV | 531 | 24 | — |
| 0074 | 0.5 | IV | 121 | 13 | 77.2 |
|  | 0.08 | IV | 198 | 16 | 62.8 |
|  | 0.025 | IV | 340 | 23 | 36.1 |
| 0089 | 0.5 | IV | 371 | 23 | 30.0 |
|  | 0.08 | IV | 423 | 22 | 20.4 |
|  | 0.025 | IV | 471 | 24 | 11.3 |

TABLE 13-H

In Vivo Tumor Inhibition Adoptive T Cell Transfer Model, with MX1-Luc Engraftment, Antibodies 0068 and 1167

| Treatment | Dose (mg/kg) | Route | Day 13 tumor volume (mm³) | SEM (mm³) | tumor growth inhibition (%) |
|---|---|---|---|---|---|
| Vehicle | — | IV | 895 | 25 | — |
| 0086 | 0.5 | IV | 921 | 20 | -2.9 |
| 1167 | 0.5 | IV | 31 | 2 | 96.5 |
|  | 0.05 | IV | 39 | 6 | 95.6 |
|  | 0.01 | IV | 426 | 25 | 52.4 |
|  | 0.0015 | IV | 352 | 67 | 60.7 |
|  | 0.5 | SC | 30 | 7 | 96.6 |
|  | 0.05 | SC | 34 | 5 | 96.2 |
|  | 0.01 | SC | 324 | 32 | 63.8 |
|  | 0.0015 | Sc | 481 | 15 | 46.2 |

TABLE 13-I

In Vivo Tumor Inhibition Adoptive T Cell Transfer Model, with MX1-Luc Engraftment, Antibodies 0068 and 0074

| Treatment | Dose (mg/kg) | Route | Day 13 tumor volume (mm³) | SEM (mm³) | tumor growth inhibition (%) |
|---|---|---|---|---|---|
| Vehicle | — | IV | 733 | 35 | — |
| 0074 | 0.5 | IV | 95 | 10 | 87.1 |
|  | 0.05 | IV | 462 | 53 | 37.0 |
| 0068 | 0.5 | IV | 19 | 8 | 97.4 |
|  | 0.05 | IV | 10 | 6 | 98.6 |

TABLE 13-J

In Vivo Tumor Inhibition Adoptive T Cell Transfer Model, T47D Engraftment, Antibody 1167

| Treatment | Dose (mg/kg) | Route | Day 12 tumor volume (mm³) | SEM (mm³) | tumor growth inhibition (%) |
|---|---|---|---|---|---|
| Vehicle | — | IV | 260 | 20 | — |
| 1167 | 0.5 | IV | 99 | 7 | 62.1 |

TABLE 13-K

In Vivo Tumor Inhibition PMBC Model, ZR75-1 Engraftment, Antibodies 0068 and 0074

| Treatment | Dose (mg/kg) | Route | Day 11 tumor volume (mm³) | SEM (mm³) | tumor growth inhibition (%) |
|---|---|---|---|---|---|
| Vehicle | — | IV | 522 | 42 | — |
| 0074 | 0.5 | IV | 491 | 54 | 5.9160115 |
| 0068 | 0.5 | IV | 176 | 33 | 66.220419 |

TABLE 13-L

In Vivo Tumor Inhibition PMBC Model, PDX-BRX-11380 Engraftment, Antibodies 0086 and 1167

| Treatment | Dose (mg/kg) | Route | Day 13 tumor volume (mm³) | SEM (mm³) | tumor growth inhibition (%) |
|---|---|---|---|---|---|
| Vehicle | — | IV | 350 | 42 | — |
| 0086 | 0.5 | IV | 301 | 52 | 14.0 |
| 1167 | 0.5 | IV | 95 | 31 | 72.8 |
|  | 0.07 | IV | 176 | 41 | 49.8 |
|  | 0.01 | IV | 259 | 39 | 26.1 |
|  | 0.5 | SC | 92 | 23 | 73.7 |
|  | 0.07 | SC | 282 | 64 | 19.3 |
|  | 0.01 | SC | 235 | 26 | 32.8 |

TABLE 13-M

In Vivo Tumor Inhibition PMBC Model, PDX-BRX-24301 Engraftment, Antibodies 0086, 1156 and 1167

| Treatment | Dose (mg/kg) | Route | Day 12 tumor volume (mm³) | SEM (mm³) | tumor growth inhibition (%) |
|---|---|---|---|---|---|
| Vehicle | — | IV | 443 | 66 | — |
| 0086 | 0.5 | IV | 514 | 80 | -16.0 |
| 1167 | 0.5 | IV | 124 | 17 | 72.1 |
|  | 0.05 | IV | 287 | 36 | 35.2 |
|  | 0.005 | IV | 413 | 59 | 6.8 |
| 1156 | 0.5 | IV | 346 | 69 | 22.0 |
|  | 0.05 | IV | 419 | 100 | 5.33 |
|  | 0.005 | IV | 559 | 130 | -26.2 |

TABLE 13-N

In Vivo Tumor Inhibition PMBC Model, PDX-BRX-26305 Engraftment, Antibodies 0086 and 1167

| Treatment | Dose (mg/kg) | Route | Day 14 tumor volume (mm³) | SEM (mm³) | tumor growth inhibition (%) |
|---|---|---|---|---|---|
| Vehicle | — | IV | 1076 | 63 | — |
| 0086 | 0.5 | IV | 1200 | 106 | -11.5 |
| 1167 | 0.5 | IV | 63 | 13 | 94.2 |
|  | 0.07 | IV | 439 | 77 | 59.2 |
|  | 0.01 | IV | 992 | 132 | 7.77 |
|  | 0.5 | SC | 176 | 70 | 83.6 |

TABLE 13-N-continued

In Vivo Tumor Inhibition PMBC Model, PDX-BRX-26305 Engraftment, Antibodies 0086 and 1167

| Treatment | Dose (mg/kg) | Route | Day 14 tumor volume (mm³) | SEM (mm³) | tumor growth inhibition (%) |
|---|---|---|---|---|---|
|  | 0.07 | SC | 531 | 113 | 50.6 |
|  | 0.01 | SC | 806 | 89 | 25.1 |

Example 12: Receptor Density Assay for B37-H-4

B37-H-4 expressing human tumor cells were harvested and stained with serial dilutions of antibody-PE 1:1 conjugated anti B37-H-4 antibodies and a negative control antibody. Stained cells along with BD Quantibrite™ phycoerythrin (PE) Quantitation kit (BD Biosciences, catalog number 340495) were acquired using BD LSRFortessa X-20. Averaged receptor density of B7-H-4 per cell at the saturating concentration of antibodies was calculated using the standard curve from the Quantibrite PE kit.

The results are shown in Table 14. The results demonstrate there is a strong correlation between B7-H-4 density on the tumor cells and the in vitro potency of antibody 1167 in inducing redirected T cell killing of the tumor cell in vitro, that the higher the B7-H-4 density, the higher the potency, as indicated smaller EC50 values

TABLE 14

B7-H4 Expression Density of Human Tumor Cell Line and EC50 of Antibody 1167 in Inducing Redirected T Cell Killing in Vitro

| Cell-Line | B7-H4 Density (per cell) | EC50 (nM) |
|---|---|---|
| MX1 | 108684 | 0.062 |
| MDA-MB-468 | 83936 | 0.40 |
| HCC1954 | 20039 | 0.80 |
| T47D | 6133 | 0.54 |
| MDA-MB-453 | 1198 | 8.44 |

Example 13: Epitope Binning of the B7-H4 Antibodies

B7-H4 antibodies in the monoclonal IgG1 form were evaluated for competitive and non-competitive binding against human B7-H4 using a tandem binning assay with an OctetRED 384 (ForteBio). Octet assays were conducted at room temperature. First, the Amine Reactive 2nd Generation sensors (AR2G) were activated for 300 s with EDC (1-Ethyl-3-[3-dimethylaminopropyl] carbodiimide hydrochloride) and s-NHS (N-hydroxysulfosuccinimide). Preactivated sensors were then coated for 300 s with the first set of anti-B7-H4 antibodies (mAb 1) diluted in sodium acetate pH 5.0 and then quenched with ethanol amine for additional 300 s. After equilibrating the sensor in the kinetics buffer for 60 s, human B7-H4 was allowed to bind to the captured mAb 1 for 300 s. Then the sensors were dipped into the kinetics buffer for 60 s followed by the incubation with a second antibody (mAb 2) for 300 s. Each of the antibodies was tested in this pairwise combinatorial manner. mAbs that compete for the same binding region on human B7-H4 ECD were grouped into a single bin. The epitope binning by Octet of anti-B7-H4 antibodies demonstrates two unique epitope groups recognized by the B7-H4 antibodies (Table 15).

TABLE 15

Epitope binning of the hybridoma clones using human B7-H4 ECD.

| Clone | Antibody | Bin |
|---|---|---|
| 7H7 | 0047 | 2 |
| 11F12 | 0048 | 1 |
| 13F4 | 0049 | 1 |
| 19D3 | 0050 | 2 |
| 27C12 | 0051 | 1 |
| 28D10 | 0052 | 2 |
| 29G6 | 0053 | 1 |
| 29H9 | 0054 | NA |
| 32F3 | 0055 | 1 |
| 33G4 | 0056 | 1 |
| 34A3 | 0057 | 1 |
| 37D4 | 0058 | 1 |
| 47A1 | 0059 | 1 |
| 42E2 | 0060 | 1 |
| 46E10 | 0061 | 1 |

Example 14: Crystallization and Structure Determination of Anti-B7-H4 Antibody 0052 scFv, Anti-B7-H4 Antibody 0058 Fab and Antibody 1114 Fab, in Complex with B7-H4 Extracellular Domain (ECD)

Antibody 0052 scFv and B7-H4 ECD cocrystal structure: For crystallization trials, the complex between B7-H4 antibody 0052 scFv and B7-H4 ECD was formed at 1:1.2 molar ratio and was concentrated to 15.2 mg/ml in a protein solution containing TBS at pH 7.5. The crystals were obtained by hanging-drop vapor-diffusion method from a condition containing 100 mM HEPES pH 7.5, 200 mM lithium sulfate, 25% PEG 3350. The crystals had symmetry consistent with orthorhombic space group=$P2_12_12_1$ with cell parameters a=59.33 Å; b=169.60 Å; c=213.98 Å and with two copies of B7-H4 antibody 0052 scFv and B7-H4 ECD complexes in the crystallographic asymmetric unit. The crystals were flash frozen in liquid nitrogen. A data set to a 2.6 Å resolution was collected from a single frozen crystal at IMCA beamline 17-ID at the Argonne National Laboratory (APS). The data were processed and scaled using autoPROC, and the final data set was 60.3% complete.

The structure was solved by molecular replacement with PHASER. Several iterative rounds of manual adjustment and model rebuilding using COOT and crystallographic refinement using autoBUSTER yielded the final model of antibody 0052 scFv+B7-H4 ECD with a crystallographic $R_{work}$ of 22.2% and $R_{free}$ of 25.0%, where $R_{work}=||F_{obs}|-|F_{calc}||/|F_{obs}|$ and $R_{free}$ is equivalent to $R_{work}$, but calculated for a randomly chosen 5% of reflections omitted from the refinement process.

The crystal structure of B7-H4 antibody 0052 scFV complexed with B7-H4 ECD is shown in FIG. 2A. As shown in FIG. 2A, B7-H4 antibody 0052 binds to the V2 domain of the B7-H4 ECD, and distant from the front beta sheet of the B7-H4 V1 domain.

Epitope amino acid residues on the B7-H4 ECD are identified as amino acid residues having contact with antibody 0052 amino acid residues of 3.8 Angstroms or less. Table 16-A lists the amino acid residues of the B7-H4 ECD involved in the epitope recognized by antibody 0052. Among these, B7-H4 ECD epitope amino acid resides that (1) form hydrogen bonding with the corresponding antibody amino acid residue, or (2) buried upon the target-antibody interaction, are further noted in the Table.

TABLE 16-A

B7-H4 Extra Cellular Domain Epitope Amino Acid Residues with Antibody 0052

| Amino acid Residue | Position on SEQ ID NO: 1 | Further notes |
|---|---|---|
| V | 129 | Hydrogen bond |
| Y | 131 | Hydrogen bond |
| N | 132 | |
| S | 134 | |
| S | 135 | |
| E | 136 | Hydrogen bond |
| L | 138 | |
| V | 189 | Buried in interaction |
| I | 191 | |
| V | 212 | Hydrogen bond |
| E | 214 | Hydrogen bond |
| S | 215 | Hydrogen bond |
| E | 216 | |
| I | 217 | |

Antibody 0058 Fab and B7-H4 ECD cocrystal structure: Similarly, the complex between B7-H4 antibody 0058 Fab and B7-H4 ECD was formed at 1:1.2 molar ratio and was concentrated to 9.1 mg/ml in a protein solution containing TBS at pH 7.5. The crystals were obtained by hanging-drop vapor-diffusion method from a condition containing 100 mM HEPES pH 7.5, 100 mM potassium chloride, 15% PEG 6000. The crystals had symmetry consistent with monoclinic space group=P2$_1$ with cell parameters a=81.07 Å; b=96.99 Å; c=116.08 Å, α=90.00°; β=103.19°; γ=90.0° and with two copies of B7H4 antibody 0058 Fab-B7-H4 complexes in the crystallographic asymmetric unit. The crystals were cryo-protected using reservoir solution containing 20% ethylene glycol and were flash frozen in liquid nitrogen. A data set to a 2.2 Å resolution was collected from a single frozen crystal at IMCA beamline 17-ID at the Argonne National Laboratory (APS). The data were processed and scaled using autoPROC, and the final data set was 52.9% complete.

The structure was solved by molecular replacement with PHASER. Several iterative rounds of manual adjustment and model rebuilding using COOT and crystallographic refinement using autoBUSTER yielded the final model of B7H4 antibody 0058 Fab+B7-H4 ECD with a crystallographic $R_{work}$ of 21.6% and $R_{free}$ of 23.7%, where $R_{work}=||F_{obs}|-|F_{calc}||/|F_{obs}|$ and $R_{free}$ is equivalent to $R_{work}$, but calculated for a randomly chosen 5% of reflections omitted from the refinement process.

Figure 2B:
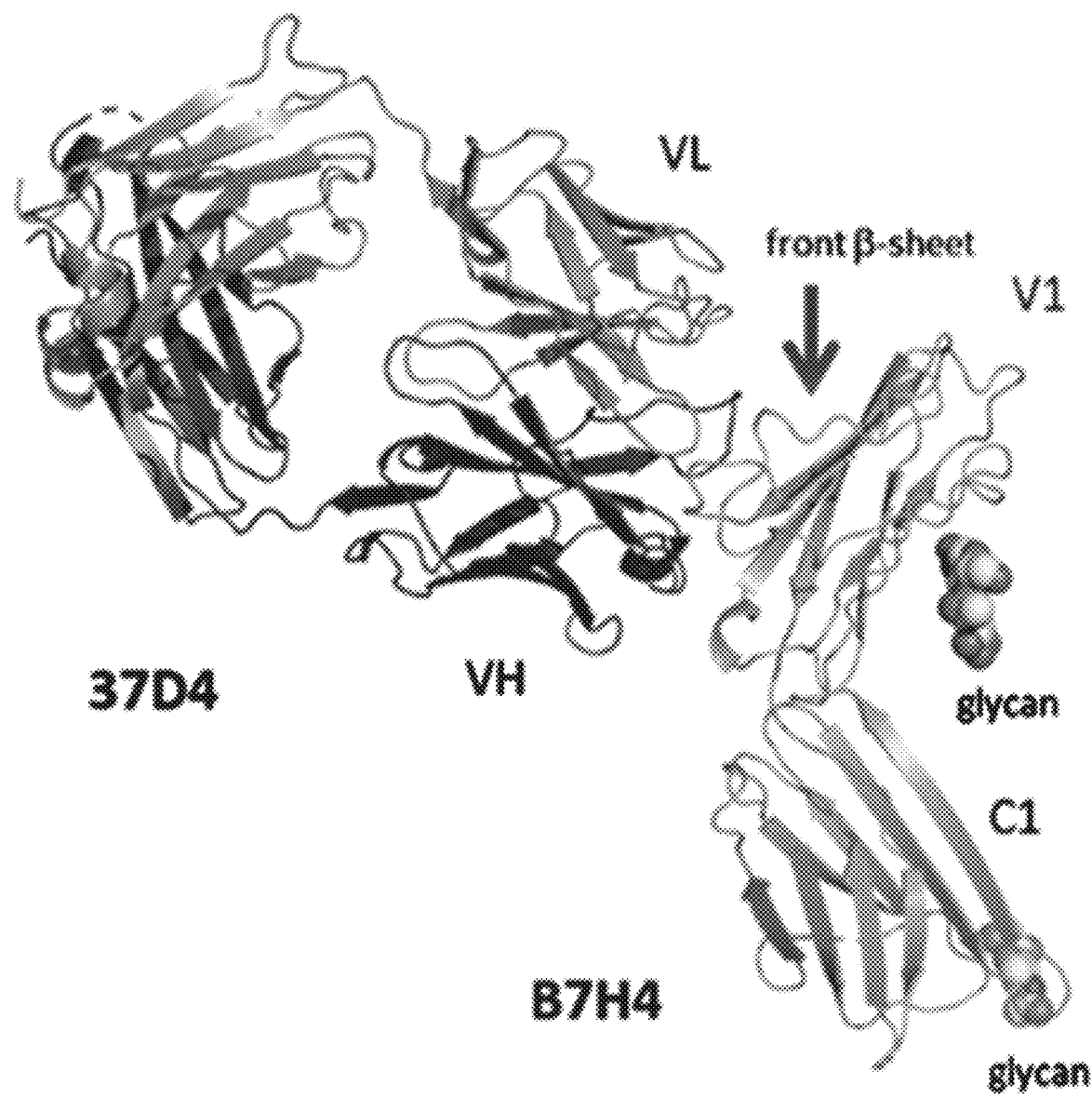
FIG. 2B depicts the co-crystal structure of B7-H4 antibody 0058 Fab and human B7-H4 extracellular domain.

The crystal structure of B7-H4 antibody 0058 Fab complexed with B7-H4 ECD is shown in FIG. 2B. As shown in FIG. 2B, B7-H4 antibody 0058 binds to the B7-H4 ECD at and around the front beta sheet of V1 domain of the B7-H4 ECD.

Epitope amino acid residues on the B7-H4 ECD are identified as amino acid residues having contact with antibody 0058 amino acid residues of 3.8 Angstroms or less. Table 16-B lists the amino acid residues of the B7-H4 ECD involved in the epitope recognized by antibody 0058. Among these, B7-H4 ECD epitope amino acid resides that (1) form hydrogen bonding with the corresponding antibody amino acid residue, or (2) buried upon the target-antibody interaction, are further noted in the Table.

Antibody 1114 Fab and B7-H4 ECD cocrystal structure: The complex between B7H4 antibody 1114 Fab and B7-H4 ECD was formed at 1:1 molar ratio and was concentrated to 9.27 mg/ml in a protein solution containing TBS at pH 7.5. The crystals were obtained by hanging-drop vapor-diffusion method from a condition containing 100 mM HEPES pH 7.5, 100 mM potassium chloride, 15% PEG 6000. The crystals had symmetry consistent with monoclinic space group=P2$_1$ with cell parameters a=96.43 Å; b=78.19 Å; c=116.21, α=90.00; β=90.13.19; γ=90.00 Å and with two copies of B7-H4 antibody 1114 Fab and B7-H4 EDC complexes in the crystallographic asymmetric unit. The crystals were cryo-protected using reservoir solution containing 20% glycerol and were flash frozen in liquid nitrogen. A data set to a 2.32 Å resolution was collected from a single frozen crystal at IMCA beamline 17-ID at the Argonne National Laboratory (APS). The data were processed and scaled using autoPROC, and the final data set was 47.6% complete.

The structure was solved by molecular replacement with PHASER. Several iterative rounds of manual adjustment and model rebuilding using COOT and crystallographic refinement using Phenix yielded the final model of B7-H4 antibody 1114 Fab+B7-H4 ECD with a crystallographic $R_{work}$ of 22.4% and $R_{free}$ of 27.6%, where $R_{work}=||F_{obs}|-|F_{calc}||/|F_{obs}|$ and $R_{free}$ is equivalent to $R_{work}$, but calculated for a randomly chosen 5% of reflections omitted from the refinement process.

Figure 2C:
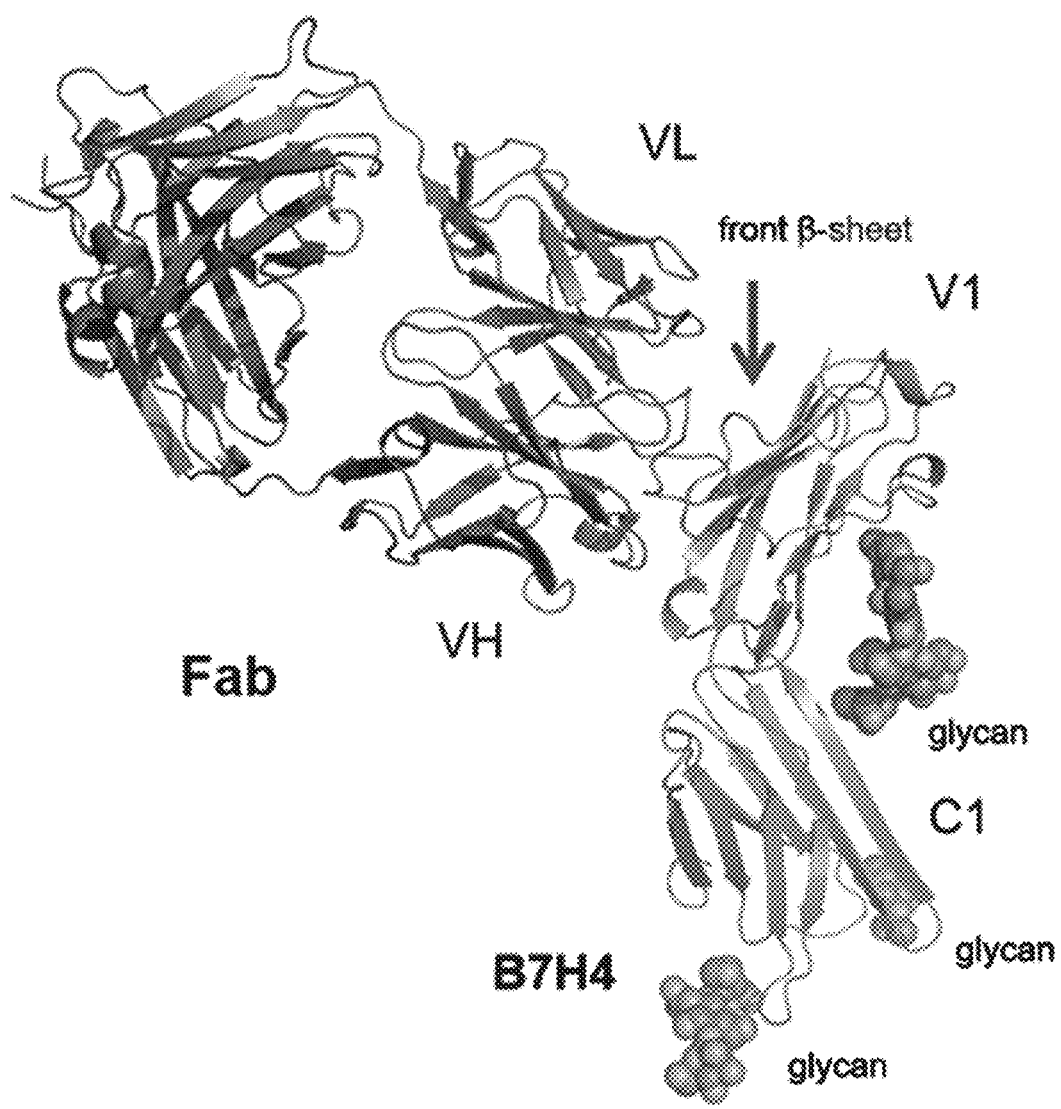
FIG. 2C depicts the co-crystal structure of B7-H4 antibody 1114 Fab and human B7-H4 extracellular domain.

The crystal structure of B7-H4 antibody 1114 Fab complexed with B7-H4 ECD is shown in FIG. 2C. As shown in FIG. 2C, B7-H4 antibody 1114 binds to the B7-H4 ECD at and around the front beta sheet of V1 domain of the B7-H4 ECD.

Epitope amino acid residues on the B7-H4 ECD are identified as amino acid residues having contact with antibody 1114 amino acid residues of 3.8 Angstroms or less. Table 16-B lists the amino acid residues of the B7-H4 ECD involved in the epitope recognized by antibody 1114. Among these, B7-H4 ECD epitope amino acid resides that (1) form hydrogen bonding with the corresponding antibody amino acid residue, or (2) buried upon the target-antibody interaction, are further noted in the Table.

TABLE 16-B

B7-H4 Extra Cellular Domain Epitope Amino Acid Residues with both Antibody 0058 and Antibody 1114

| Amino acid Residue | Position on SEQ ID NO: 1 | Further notes |
|---|---|---|
| L | 44 | Hydrogen bond |
| K | 45 | |
| E | 46 | Hydrogen bond |
| G | 47 | Hydrogen bond |
| V | 48 | |
| L | 49 | Hydrogen bond |
| G | 50 | |
| L | 51 | |
| S | 63 | Only bound to antibody 0058 |
| E | 64 | Hydrogen bond |
| D | 66 | Hydrogen bond |
| M | 68 | |
| T | 99 | Buried in interaction |
| K | 101 | Buried in interaction |

It is claimed:

1. A bispecific antibody that specifically binds to both B7-H4 and CD3, comprising a first heavy chain and a first light chain, and a second heavy chain and a second light chain, wherein the first heavy chain and the first light chain form a first arm which comprises a first antigen binding domain that binds to B7-H4, and the second heavy chain and the second light chain form a second arm which comprises a second antigen binding domain that binds to CD3, wherein
   (a) the first heavy chain comprises a VH CDR1 having the amino acid sequence of SEQ ID NO: 20; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153;
   (b) the first heavy chain comprises a VH CDR1 having the amino acid sequence of SEQ ID NO: 205; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153;
   (c) the first heavy chain comprises a VH CDR1 having the amino acid sequence of SEQ ID NO: 206; a VH CDR2 having the amino acid sequence of SEQ ID NO:207, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153;
   (d) the first heavy chain comprises a VH CDR1 having the amino acid sequence of SEQ ID NO: 5; a VH CDR2 having the amino acid sequence of SEQ ID NO:6, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138;
   (e) the first heavy chain comprises a VH CDR1 having the amino acid sequence of SEQ ID NO: 200; a VH CDR2 having the amino acid sequence of SEQ ID NO:201, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138;
   (f) the first heavy chain comprises a VH CDR1 having the amino acid sequence of SEQ ID NO: 199; a VH CDR2 having the amino acid sequence of SEQ ID NO:6, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138;
   (g) the first heavy chain comprises a VH CDR1 having the amino acid sequence of SEQ ID NO: 20; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 152, a VL CDR2 having the amino acid sequence of SEQ ID NO:41 and a VL CDR3 having the amino acid sequence of SEQ ID NO:153;
   (h) the first heavy chain comprises a VH CDR1 having the amino acid sequence of SEQ ID NO: 5; a VH CDR2 having the amino acid sequence of SEQ ID NO:6, a VH CDR3 having the amino acid sequence of SEQ ID NO:7, a VL CDR1 having the amino acid sequence of SEQ ID NO: 9, and the first light chain comprises a VL CDR2 having the amino acid sequence of SEQ ID NO:10 and a VL CDR3 having the amino acid sequence of SEQ ID NO:138; or (i) the first heavy chain comprises a VH CDR1 having the amino acid sequence of SEQ ID NO: 5; a VH CDR2 having the amino acid sequence of SEQ ID NO:130, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138.

2. The bispecific antibody of claim 1, wherein
(a) the first heavy chain comprises a VH having the amino acid sequence of SEQ ID NO:161, and the first light chain comprises a VL having the amino acid sequence of SEQ ID NO:167;
(b) the first heavy chain comprises a VH having the amino acid sequence of SEQ ID NO:172, and the first light chain comprises a VL having the amino acid sequence of SEQ ID NO:139;
(c) the first heavy chain comprises a VH having the amino acid sequence of SEQ ID NO:155; and the first light chain comprises a VL having the amino acid sequence of SEQ ID NO:139;
(d) the first heavy chain comprises a VH having the amino acid sequence of SEQ ID NO:156; and the first light chain comprises a VL having the amino acid sequence of SEQ ID NO:139;
(e) the first heavy chain comprises a VH having the amino acid sequence of SEQ ID NO:157; and the first light chain comprises a VL having the amino acid sequence of SEQ ID NO:141;
(f) the first heavy chain comprises a VH having the amino acid sequence of SEQ ID NO:155; and the first light chain comprises a VL having the amino acid sequence of SEQ ID NO:141;
(g) the first heavy chain comprises a VH having the amino acid sequence of SEQ ID NO:156; and the first light chain comprises a VL having the amino acid sequence of SEQ ID NO:141;
(h) the first heavy chain comprises a VH having the amino acid sequence of SEQ ID NO:159; and the first light chain comprises a VL having the amino acid sequence of SEQ ID NO:27;
(i) the first heavy chain comprises a VH having the amino acid sequence of SEQ ID NO:161; and the first light chain comprises a VL having the amino acid sequence of SEQ ID NO:27;
(j) the first heavy chain comprises a VH having the amino acid sequence of SEQ ID NO:163; and the first light chain comprises a VL having the amino acid sequence of SEQ ID NO:27;
(k) the first heavy chain comprises a VH having the amino acid sequence of SEQ ID NO:165; and the first light chain comprises a VL having the amino acid sequence of SEQ ID NO:27;
(l) the first heavy chain comprises a VH having the amino acid sequence of SEQ ID NO:23; and the first light chain comprises a VL having the amino acid sequence of SEQ ID NO:167;
(m) the first heavy chain comprises a VH having the amino acid sequence of SEQ ID NO:171; and the first light chain comprises a VL having the amino acid sequence of SEQ ID NO:141;
(n) the first heavy chain comprises a VH having the amino acid sequence of SEQ ID NO:172; and the first light chain comprises a VL having the amino acid sequence of SEQ ID NO:141;
(o) the first heavy chain comprises a VH having the amino acid sequence of SEQ ID NO:171; and the first light chain comprises a VL having the amino acid sequence of SEQ ID NO:139;
(p) the first heavy chain comprises a VH having the amino acid sequence of SEQ ID NO:173; and the first light chain comprises a VL having the amino acid sequence of SEQ ID NO:139;
(q) the first heavy chain comprises a VH having the amino acid sequence of SEQ ID NO:174; and the first light chain comprises a VL having the amino acid sequence of SEQ ID NO:139;
(r) the first heavy chain comprises a VH having the amino acid sequence of SEQ ID NO:175; and the first light chain comprises a VL having the amino acid sequence of SEQ ID NO:139;
(s) the first heavy chain comprises a VH having the amino acid sequence of SEQ ID NO:161; and a VL having the amino acid sequence of SEQ ID NO:168;
(t) the first heavy chain comprises a VH having the amino acid sequence of SEQ ID NO:161; and the first light chain comprises a VL having the amino acid sequence of SEQ ID NO:169;
(u) the first heavy chain comprises a VH having the amino acid sequence of SEQ ID NO:161; and the first light chain comprises a VL having the amino acid sequence of SEQ ID NO:170; or
(v) the first heavy chain comprises a VH having the amino acid sequence of SEQ ID NO:172; and the first light chain comprises a VL having the amino acid sequence of SEQ ID NO:139.

3. The bispecific antibody of claim 1, wherein
(a) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34;
(b) the second heavy chain comprises a VH CDR1 having the amino acid sequence of SEQ ID NO: 202, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34;
(c) the second heavy chain comprises a VH CDR1 having the amino acid sequence of SEQ ID NO: 203, a VH CDR2 having the amino acid sequence of SEQ ID NO:204, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34;
(d) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:116;

(e) the second heavy chain comprises a VH CDR1 having the amino acid sequence of SEQ ID NO: 28, a VH CDR2 having the amino acid sequence of SEQ ID NO:109, a VH CDR3 having the amino acid sequence of SEQ ID NO:30, and the second light chain comprises a VL CDR1 having the amino acid sequence of SEQ ID NO: 111, a VL CDR2 having the amino acid sequence of SEQ ID NO:112 and a VL CDR3 having the amino acid sequence of SEQ ID NO:34; or (f) the second heavy chain comprises a VH CDR1 having the amino acid sequence of SEQ ID NO: 28, a VH CDR2 having the amino acid sequence of SEQ ID NO:29, a VH CDR3 having the amino acid sequence of SEQ ID NO:30, and the second light chain comprises a VL CDR1 having the amino acid sequence of SEQ ID NO: 32, a VL CDR2 having the amino acid sequence of SEQ ID NO:33 and a VL CDR3 having the amino acid sequence of SEQ ID NO:34.

4. The bispecific antibody of claim 1, wherein (a) the second heavy chain comprises a VH having the amino acid sequence of SEQ ID NO: 106, and the second light chain comprises a VL having the amino acid sequence of SEQ ID NO: 108;

(b) the second heavy chain comprises a VH having the amino acid sequence of SEQ ID NO: 115, and the second light chain comprises a VL having the amino acid sequence of SEQ ID NO: 117;

(c) the second heavy chain comprises a VH having the amino acid sequence of SEQ ID NO: 110, and the second light chain comprises a VL having the amino acid sequence of SEQ ID NO: 113; or (d) the second heavy chain comprises a VH having the amino acid sequence of SEQ ID NO: 31, and the second light chain comprises a VL having the amino acid sequence of SEQ ID NO: 35.

5. The bispecific antibody of claim 1, wherein (a) the first heavy chain comprises a VH CDR1 having the amino acid sequence of SEQ ID NO: 20; a VH CDR2 having the amino acid sequence of SEQ ID NO:21, a VH CDR3 having the amino acid sequence of SEQ ID NO:160, and the first light chain comprises a VL CDR1 having the amino acid sequence of SEQ ID NO: 166, a VL CDR2 having the amino acid sequence of SEQ ID NO:25 and a VL CDR3 having the amino acid sequence of SEQ ID NO:153; and (b) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34.

6. The bispecific antibody of claim 1, wherein (a) the first heavy chain comprises a VH CDR1 having the amino acid sequence of SEQ ID NO: 5; a VH CDR2 having the amino acid sequence of SEQ ID NO:6, a VH CDR3 having the amino acid sequence of SEQ ID NO:7, and the first light chain comprises a VL CDR1 having the amino acid sequence of SEQ ID NO: 9, a VL CDR2 having the amino acid sequence of SEQ ID NO:10 and a VL CDR3 having the amino acid sequence of SEQ ID NO:138; and (b) the second heavy chain comprises a VH CDR1 having the amino acid sequence of SEQ ID NO: 28, a VH CDR2 having the amino acid sequence of SEQ ID NO:105, a VH CDR3 having the amino acid sequence of SEQ ID NO:30, and the second light chain comprises a VL CDR1 having the amino acid sequence of SEQ ID NO: 107, a VL CDR2 having the amino acid sequence of SEQ ID NO:33 and a VL CDR3 having the amino acid sequence of SEQ ID NO:34.

7. A bispecific antibody that specifically binds to both B7-H4 and CD3, comprising a first heavy chain and a first light chain, and a second heavy chain and a second light chain, wherein the first heavy chain and the first light chain form a first arm which comprises a first antigen binding domain that binds to B7-H4, and the second heavy chain and the second light chain form a second arm which comprises a second antigen binding domain that binds to CD3, and wherein (a) the first heavy chain comprises a VH having the amino acid sequence of SEQ ID NO:161, and the first light chain comprises a VL having the amino acid sequence of SEQ ID NO:167; and (b) the second heavy chain comprises a VH having the amino acid sequence of SEQ ID NO: 106, and the second light chain comprises a VL having the amino acid sequence of SEQ ID NO:108.

8. The bispecific antibody of claim 1, wherein (c) the first heavy chain comprises a VH having the amino acid sequence of SEQ ID NO:172, and the first light chain comprises a VL having the amino acid sequence of SEQ ID NO:139; and (d) the second heavy chain comprises a VH having the amino acid sequence of SEQ ID NO: 106, and the second light chain comprises a VL having the amino acid sequence of SEQ ID NO:108.

9. The bispecific antibody of claim 1, wherein the first arm further comprises human IgG2ΔA constant region with substitutions D265A, C223E, P228E, and L368E, the second arm further comprises a human IgG2ΔA constant region with substitutions D265A, C223R, E225R, P228R, and K409R, wherein the numbering is according to the human wildtype IgG2 and EU numbering schemes.

10. A bispecific antibody that specifically binds to both B7-H4 and CD3, comprising a first heavy chain and a first light chain, and a second heavy chain and a second light chain, wherein the first heavy chain and the first light chain form a first antibody arm which comprises a first antigen binding domain that binds to B7-H4, and the second heavy chain and the second light chain form a second antigen binding domain that binds to CD3, wherein (a) the first heavy chain having the amino acid sequence of SEQ ID NO: 190; and the first light chain having the amino acid sequence of SEQ ID NO: 191; and (b) the second heavy chain having the amino acid sequence of SEQ ID NO:188, and the second light chain having the amino acid sequence of SEQ ID NO: 189.

11. A bispecific antibody that specifically binds to both B7-H4 and CD3, comprising a first heavy chain and a first light chain, and a second heavy chain and a second light chain, wherein the first heavy chain and the first light chain form a first antibody arm which comprises a first antigen binding domain that binds to B7-H4, and the second heavy chain and the second light chain forms a second antigen binding domain that binds to CD3, wherein
(a) the first heavy chain having the amino acid sequence of SEQ ID NO: 186; and the first light chain having the amino acid sequence of SEQ ID NO: 187; and
(b) the second heavy chain having the amino acid sequence of SEQ ID NO:188, and the second light chain having the amino acid sequence of SEQ ID NO:189.

12. A bispecific antibody that specifically binds to B7-H4 and CD3, comprising a first heavy chain and a first light chain, and a second heavy chain and a second light chain, wherein the first heavy chain and the first light chain form a first antibody arm which comprises a first antigen binding domain that binds to B7-H4, and the second heavy chain and the second light chain form a second antigen binding domain that binds to CD3, wherein
(a) the first heavy chain comprises the amino acid sequence of the full-length polypeptide encoded by the open reading frame (ORF) deposited under ATCC Accession No. PTA-126779, and the first light chain comprises the amino acid sequence of the full-length polypeptide encoded by the open reading frame (ORF) deposited under ATCC Accession No. PTA-126781; and
(b) the second heavy chain comprises the amino acid sequence of the full-length polypeptide encoded by the open reading frame (ORF) deposited under ATCC Accession No. PTA-126780, and the second light chain comprises the amino acid sequence of the full-length polypeptide encoded by the open reading frame (ORF) deposited under ATCC Accession No. PTA-126782.

13. An isolated polynucleotide molecule encoding (i) a heavy chain of the antibody of claim 1 or (ii) a light chain of the antibody of claim 1.

14. A vector comprising the polynucleotide molecule of claim 13.

15. A host cell comprising the vector of claim 14.

16. A method of treating cancer in a subject in need comprising administering to the subject the bispecific antibody claim 1.

17. A pharmaceutical composition comprising the bispecific antibody of claim 1.

18. A method of treating a condition associated with malignant cells expressing B7-H4 in a subject comprising administering to the subject in need thereof a therapeutically effective amount of the pharmaceutical composition of claim 17.

19. The method of claim 18, wherein the condition is a cancer.

20. A method of inhibiting tumor growth or progression in a subject who has malignant cells expressing B7-H4, comprising administering to the subject in need thereof a therapeutically effective amount of the pharmaceutical composition of claim 17.

21. A method of inducing tumor regression in a subject who has malignant cells expressing B7-H4, comprising administering to the subject in need thereof an effective amount of the pharmaceutical composition of claim 17.

\* \* \* \* \*

SEQUENCE LISTING

<160> NUMBER OF SEQ ID NOS: 210

<210> SEQ ID NO 1
<211> LENGTH: 230
<212> TYPE: PRT
<213> ORGANISM: Homo sapiens

<400> SEQUENCE: 1

Phe Gly Ile Ser Gly Arg His Ser Ile Thr Val Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
                35                  40                  45

Leu Gly Leu Val His Glu Phe Lys Glu Gly Lys Asp Glu Leu Ser Glu
50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala
225                 230

<210> SEQ ID NO 2
<211> LENGTH: 230
<212> TYPE: PRT
<213> ORGANISM: Macaca fascicularis

<400> SEQUENCE: 2

Phe Gly Ile Ser Gly Arg His Ser Ile Thr Val Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
                35                  40                  45

Ile Gly Leu Val His Glu Phe Lys Glu Gly Lys Asp Glu Leu Ser Glu
50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp

```
                85                  90                  95
Ala Gly Thr Tyr Lys Cys Tyr Ile Ile Thr Ser Lys Gly Lys Gly Asn
                100                 105                 110

Ala Asn Leu Glu Tyr Lys Thr Gly Ala Phe Ser Met Pro Glu Val Asn
            115                 120                 125

Val Asp Tyr Asn Ala Ser Ser Glu Thr Leu Arg Cys Glu Ala Pro Arg
        130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala
225                 230

<210> SEQ ID NO 3
<211> LENGTH: 230
<212> TYPE: PRT
<213> ORGANISM: Mus musculus

<400> SEQUENCE: 3

Phe Gly Ile Ser Gly Lys His Phe Ile Thr Val Thr Thr Phe Thr Ser
1               5                   10                  15

Ala Gly Asn Ile Gly Glu Asp Gly Thr Leu Ser Cys Thr Phe Glu Pro
            20                  25                  30

Asp Ile Lys Leu Asn Gly Ile Val Ile Gln Trp Leu Lys Glu Gly Ile
        35                  40                  45

Lys Gly Leu Val His Glu Phe Lys Glu Gly Lys Asp Asp Leu Ser Gln
50                  55                  60

Gln His Glu Met Phe Arg Gly Arg Thr Ala Val Phe Ala Asp Gln Val
65                  70                  75                  80

Val Val Gly Asn Ala Ser Leu Arg Leu Lys Asn Val Gln Leu Thr Asp
                85                  90                  95

Ala Gly Thr Tyr Thr Cys Tyr Ile Arg Thr Ser Lys Gly Lys Gly Asn
                100                 105                 110

Ala Asn Leu Glu Tyr Lys Thr Gly Ala Phe Ser Met Pro Glu Ile Asn
            115                 120                 125

Val Asp Tyr Asn Ala Ser Ser Glu Ser Leu Arg Cys Glu Ala Pro Arg
        130                 135                 140

Trp Phe Pro Gln Pro Thr Val Ala Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Asp Ser Glu Val Lys Arg Arg Ser Gln Leu Gln
    210                 215                 220
```

```
Leu Leu Asn Ser Gly Pro
225                 230

<210> SEQ ID NO 4
<211> LENGTH: 229
<212> TYPE: PRT
<213> ORGANISM: Rattus norvegicus

<400> SEQUENCE: 4

Phe Gly Ile Ser Gly Lys His Phe Ile Thr Val Thr Phe Thr Ser
1               5                   10                  15

Ala Gly Asn Ile Gly Glu Asp Gly Thr Leu Ser Cys Thr Phe Glu Pro
            20                  25                  30

Asp Ile Lys Leu Asn Gly Ile Val Ile Gln Trp Leu Lys Glu Gly Ile
        35                  40                  45

Lys Gly Leu Val His Glu Phe Lys Glu Gly Lys Asp Asp Leu Ser Gln
    50                  55                  60

Gln His Glu Met Phe Arg Gly Arg Thr Ala Val Phe Ala Asp Gln Val
65                  70                  75                  80

Val Val Gly Asn Ala Ser Leu Arg Leu Lys Asn Val Gln Leu Thr Asp
                85                  90                  95

Ala Gly Thr Tyr Thr Cys Tyr Ile His Thr Ser Lys Gly Lys Gly Asn
            100                 105                 110

Ala Asn Leu Glu Tyr Lys Thr Gly Ala Phe Ser Met Pro Glu Ile Asn
        115                 120                 125

Val Asp Tyr Asn Ala Ser Ser Glu Ser Leu Arg Cys Glu Ala Pro Arg
    130                 135                 140

Trp Phe Pro Gln Pro Thr Val Ala Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Asp Ser Glu Val Lys Arg Arg Ser Gln Leu Glu
    210                 215                 220

Leu Leu Asn Ser Gly
225

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Gly Ser Phe Ser Gly Tyr Tyr Trp Asn
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6
```

```
Glu Ile Asn His Ser Gly Ser Ala Thr Tyr Asn Pro Ser Leu Lys Ser
1               5                   10                  15
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

```
Gly Leu Tyr Asn Trp Asn Val Asp His
1               5
```

<210> SEQ ID NO 8
<211> LENGTH: 117
<212> TYPE: PRT
<213> ORGANISM: Artificial Sequence
<220> FEATURE:
<223> OTHER INFORMATION: Synthetic Construct

<400> SEQUENCE: 8

```
Gln Val Gln Leu Gln Gln Trp Gly Ala Gly Leu Leu Lys Pro Ser Glu
1               5                   10                  15

Thr Leu Pro Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Phe Cys Ala
                85                  90                  95

Arg Gly Leu Tyr Asn Trp Asn Val Asp His Trp Gly Gln Gly Thr Leu
            100                 105                 110

Val Thr Val Ser Ser
        115
```

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

```
Arg Ala Ser Gln Gly Ile Arg Asn Asp Leu Gly
1               5                   10
```

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

```
Ala Ala Ser Ser Leu Gln Ser
1               5
```

<210> SEQ ID NO 11
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 11

Leu Gln His Asn Ser Tyr Pro Arg Thr
1               5

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gly Gly Thr Lys Val Glu Ile Lys
            100                 105

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct
```

<400> SEQUENCE: 14

Glu Ile Asn His Ser Gly Ser Thr Lys Tyr Asn Pro Ser Leu Lys Ser
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Gly Leu Tyr Asn Trp Asn Val Asp Ser
1               5

<210> SEQ ID NO 16
<211> LENGTH: 117
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Asn Trp Ile Arg Gln Pro Pro Gly Lys Gly Leu Glu Trp Ile
            35                  40                  45

Gly Glu Ile Asn His Ser Gly Ser Thr Lys Tyr Asn Pro Ser Leu Lys
        50                  55                  60

Ser Arg Val Thr Ile Ser Gly Asp Thr Ser Lys Asn Gln Phe Ser Leu
65                  70                  75                  80

Lys Leu Asn Ser Val Thr Ala Ala Asp Thr Ala Val Tyr Tyr Cys Val
                85                  90                  95

Arg Gly Leu Tyr Asn Trp Asn Val Asp Ser Trp Gly Gln Gly Thr Leu
            100                 105                 110

Val Thr Val Ser Ser
        115

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Val Ala Ser Ser Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Leu Gln His Asn Ser Tyr Pro Tyr Thr
1               5

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Gly Phe Thr Phe Ser Ser Tyr Ala Met Ser
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Ala Ile Ser Gly Gly Gly Gly Ser Thr Tyr Tyr Ala Asp Ser Val Lys
1               5                   10                  15

Gly

<210> SEQ ID NO 22
<211> LENGTH: 13
<212> TYPE: PRT
<213> ORGANISM: Artificial Sequence
<220> FEATURE:
<223> OTHER INFORMATION: Synthetic Construct

<400> SEQUENCE: 22

Asp Ile Gln Trp Phe Gly Glu Ser Thr Leu Phe Asp Tyr
1               5                   10

<210> SEQ ID NO 23
<211> LENGTH: 122
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gln Trp Phe Gly Glu Ser Thr Leu Phe Asp Tyr Trp
            100                 105                 110

Gly Gln Gly Thr Leu Val Thr Val Ser Ser
        115                 120

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Arg Ala Ser Gln Ser Ile Arg Ser Trp Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Lys Ala Ser Ser Leu Glu Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Tyr Asn Ser Tyr Ser Arg Thr
1               5

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27

Asp Ile Gln Leu Thr Gln Ser Pro Ser Thr Leu Ser Ala Ser Val Gly
1               5                   10                  15

```
Asp Arg Val Thr Ile Thr Cys Arg Ala Ser Gln Ser Ile Arg Ser Trp
            20                  25                  30

Leu Ala Trp Phe Gln Gln Lys Pro Gly Lys Ala Pro Lys Leu Leu Ile
        35                  40                  45

Tyr Lys Ala Ser Ser Leu Glu Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Gly Phe Thr Phe Ser Asp Tyr Tyr Met Thr
1               5                   10

<210> SEQ ID NO 29
<211> LENGTH: 19
<212> TYPE: PRT
<213> ORGANISM: Artificial Sequence
<220> FEATURE:
<223> OTHER INFORMATION: Synthetic Construct

<400> SEQUENCE: 29

Phe Ile Arg Asn Arg Ala Arg Gly Tyr Thr Ser Asp His Asn Pro Ser
1               5                   10                  15

Val Lys Gly

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Asp Arg Pro Ser Tyr Tyr Val Leu Asp Tyr
1               5                   10

<210> SEQ ID NO 31
<211> LENGTH: 121
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Pro
```

```
            50                  55                  60
Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
                115                 120
```

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

```
Lys Ser Ser Gln Ser Leu Phe Asn Val Arg Ser Arg Lys Asn Tyr Leu
 1               5                  10                  15

Ala
```

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

```
Trp Ala Ser Thr Arg Glu Ser
 1               5
```

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

```
Lys Gln Ser Tyr Asp Leu Phe Thr
 1               5
```

<210> SEQ ID NO 35
<211> LENGTH: 112
<212> TYPE: PRT
<213> ORGANISM: Artificial Sequence
<220> FEATURE:
<223> OTHER INFORMATION: Synthetic Construct

<400> SEQUENCE: 35

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Phe Asn Val
                20                  25                  30

Arg Ser Arg Lys Asn Tyr Leu Ala Trp Tyr Gln Gln Lys Pro Gly Gln
            35                  40                  45

Pro Pro Lys Leu Leu Ile Ser Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80
```

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Phe Thr Phe Ser Ser Tyr Ala Met Lys
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct

<400> SEQUENCE: 37

Thr Thr Ser Gly Ser Gly Gly Thr Thr Tyr Tyr Ala Asp Ser Val Lys
1               5                   10                  15

Gly

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Ala Gly Trp Ala Ala Ala Phe Asp Tyr
1               5

<210> SEQ ID NO 39
<211> LENGTH: 118
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Lys Trp Val Arg Gln Ala Pro Gly Lys Gly Leu Glu Trp Val
        35                  40                  45

Ser Thr Thr Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Trp Ala Ala Ala Phe Asp Tyr Trp Gly Gln Gly Thr
            100                 105                 110

```
Leu Val Thr Val Ser Ser
        115

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Arg Ala Ser Gln Ser Ile Ser Asp Trp Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Lys Ala Ser Ser Leu Glu Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Gln Gln Cys Asn Ser Tyr Trp Thr
1               5

<210> SEQ ID NO 43
<211> LENGTH: 106
<212> TYPE: PRT
<213> ORGANISM: Artificial Sequence
<220> FEATURE:
<223> OTHER INFORMATION: Synthetic Construct

<400> SEQUENCE: 43

Asp Ile Gln Leu Thr Gln Phe Pro Ser Thr Leu Ser Ala Ser Val Gly
1               5                   10                  15

Asp Arg Ile Thr Ile Thr Cys Arg Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Cys Asn Ser Tyr Trp Thr
                85                  90                  95

Phe Gly Gln Gly Thr Lys Val Glu Ile Lys
            100                 105

<210> SEQ ID NO 44
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 44

Ala Ile Ser Gly Ser Gly Gly Ser Thr Tyr Tyr Ala Asp Ser Val Lys
1               5                   10                  15
Gly

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct

<400> SEQUENCE: 45

Asp Ile Gln Trp Phe Gly Glu Ser Val Phe Asp Tyr
1               5                   10

<210> SEQ ID NO 46
<211> LENGTH: 121
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu His Met Asn Ser Leu Arg Ala Glu Asp Thr Ala Val Tyr Tyr Cys
                85                  90                  95

Ala Arg Asp Ile Gln Trp Phe Gly Glu Ser Val Phe Asp Tyr Trp Gly
            100                 105                 110

Gln Gly Thr Leu Val Thr Val Ser Ser
        115                 120

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Arg Ala Ser Gln Ser Ile Ser Ser Trp Leu Ala
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Gln Tyr Tyr Asn Ser Tyr Ser Arg Thr
1               5

<210> SEQ ID NO 49
<211> LENGTH: 107
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Asn Gly Ser Gly Thr Glu Phe Thr Leu Thr Ile Ser Ser Leu Gln Pro
65                  70                  75                  80

Asp Asp Leu Ala Thr Tyr Tyr Cys Gln Tyr Tyr Asn Ser Tyr Ser Arg
                85                  90                  95

Thr Phe Gly Gln Gly Thr Lys Val Glu Ile Lys
            100                 105

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Glu Ile Asn His Ser Gly Ser Ala Asn Tyr Asn Pro Ser Leu Lys Ser
1               5                   10                  15

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Gly Leu Tyr Asn Trp Asn Val Asp Arg
1               5

<210> SEQ ID NO 52
<211> LENGTH: 117
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Gln Gln Trp Gly Ala Gly Leu Leu Lys Pro Ser Glu
1               5                   10                  15

Thr Leu Ser Leu Thr Cys Ala Leu Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Ala Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Gly Leu Tyr Asn Trp Asn Val Asp Arg Trp Gly Gln Gly Thr Leu
            100                 105                 110

Val Thr Val Ser Ser
            115

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Leu Gln His Asn Ser Tyr Pro Leu Thr
1               5

<210> SEQ ID NO 54
<211> LENGTH: 107
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

Ser Ile Ser Gly Asn Gly Gly Ser Thr Tyr Tyr Ala Asp Ser Val Lys
1               5                   10                  15

Gly

<210> SEQ ID NO 56
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 56

Val Gly Trp Arg Thr Gly Asp Tyr
1               5

<210> SEQ ID NO 57
<211> LENGTH: 117
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Val Gly Trp Arg Thr Gly Asp Tyr Trp Gly Gln Gly Thr Leu
            100                 105                 110

Val Thr Val Ser Ser
        115

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Lys Ala Ser Asp Leu Glu Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Gln Tyr Asn Ser Tyr Ser Trp Thr
1               5

<210> SEQ ID NO 60
<211> LENGTH: 107
<212> TYPE: PRT
<213> ORGANISM: Artificial Sequence
<220> FEATURE:
<223> OTHER INFORMATION: Synthetic Construct

<400> SEQUENCE: 60

Asp Ile Gln Leu Thr Gln Ser Pro Ser Thr Leu Ser Ala Ser Val Gly
```

```
                1               5                   10                  15
          Asp Arg Val Thr Ile Thr Cys Arg Ala Ser Gln Ser Ile Ser Ser Trp
                            20                  25                  30

Leu Ala Trp Tyr Gln Gln Lys Ala Gly Lys Ala Pro Lys Leu Leu Ile
                      35                  40                  45

Tyr Lys Ala Ser Asp Leu Glu Ser Gly Val Pro Ser Arg Phe Ser Gly
                      50                  55                  60

Ser Gly Ser Gly Ile Glu Phe Thr Leu Thr Ile Ser Ser Leu Gln Pro
          65                  70                  75                  80

Asp Asp Phe Ala Thr Tyr Tyr Cys Gln Gln Tyr Asn Ser Tyr Ser Trp
                            85                  90                  95

Thr Phe Gly Gln Gly Thr Lys Val Glu Ile Lys
                          100                 105
```

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

```
Gly Gly Pro Phe Ser Gly Tyr Phe Trp Ser
1               5                   10
```

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct

<400> SEQUENCE: 62

```
Glu Ile Asn His Ser Gly Asn Thr Asn Tyr Asn Pro Ser Leu Lys Ser
1               5                   10                  15
```

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

```
Ala Gly Gly Asp Tyr Gly Phe Tyr Tyr Tyr Gly Met Asp Val
1               5                   10                  15
```

<210> SEQ ID NO 64
<211> LENGTH: 123
<212> TYPE: PRT
<213> ORGANISM: Artificial Sequence
<220> FEATURE:
<223> OTHER INFORMATION: Synthetic Construct

<400> SEQUENCE: 64

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Pro Phe Ser Gly Tyr
                    20                  25                  30

Phe Trp Ser Trp Ile Arg Gln Pro Pro Gly Lys Gly Leu Glu Trp Ile
              35                  40                  45

Gly Glu Ile Asn His Ser Gly Asn Thr Asn Tyr Asn Pro Ser Leu Lys
```

50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Gly Gly Asp Tyr Gly Phe Tyr Tyr Tyr Gly Met Asp Val
                100                 105                 110

Trp Gly Gln Gly Thr Thr Val Thr Val Ser Ser
        115                 120

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Lys Ala Ser Arg Leu Glu Ser
 1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Construct

<400> SEQUENCE: 66

Gln Gln Tyr Asn Ser Tyr
 1               5

<210> SEQ ID NO 67
<211> LENGTH: 104
<212> TYPE: PRT
<213> ORGANISM: Artificial Sequence
<220> FEATURE:
<223> OTHER INFORMATION: Synthetic Construct

<400> SEQUENCE: 67

Asp Ile Gln Leu Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Glu Leu Leu Val
             35                  40                  45

Tyr Lys Ala Ser Arg Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Phe Gly
                 85                  90                  95

Gly Gly Thr Lys Val Glu Ile Lys
                100

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 68

Gly Leu Tyr Asn Trp Asn Val Asp Cys
1               5

<210> SEQ ID NO 69
<211> LENGTH: 117
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Asn Ser Val Thr Ala Ala Gly Thr Ala Val Tyr Phe Cys Ala
                85                  90                  95

Arg Gly Leu Tyr Asn Trp Asn Val Asp Cys Trp Gly Gln Gly Thr Leu
            100                 105                 110

Val Thr Val Ser Ser
        115

<210> SEQ ID NO 70
<211> LENGTH: 107
<212> TYPE: PRT
<213> ORGANISM: Artificial Sequence
<220> FEATURE:
<223> OTHER INFORMATION: Synthetic Construct

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gly Gly Thr Lys Val Glu Ile Lys
            100                 105

<210> SEQ ID NO 71
<211> LENGTH: 12
<212> TYPE: PRT
<213> ORGANISM: Artificial Sequence
<220> FEATURE:
<223> OTHER INFORMATION: Synthetic Construct

<400> SEQUENCE: 71
```

```
Gly Gly Ser Ile Ser Ser Ser Tyr Tyr Trp Gly
1               5                   10
```

<210> SEQ ID NO 72
<211> LENGTH: 16
<212> TYPE: PRT
<213> ORGANISM: Artificial Sequence
<220> FEATURE:
<223> OTHER INFORMATION: Synthetic Construct

<400> SEQUENCE: 72

```
Thr Ile Tyr Phe Ser Gly Asn Thr Tyr Tyr Asn Pro Ser Leu Lys Ser
1               5                   10                  15
```

<210> SEQ ID NO 73
<211> LENGTH: 16
<212> TYPE: PRT
<213> ORGANISM: Artificial Sequence
<220> FEATURE:
<223> OTHER INFORMATION: Synthetic Construct

<400> SEQUENCE: 73

```
Leu Arg Val Thr Met Val Arg Gly Val Ile Ile Gly Val Phe Asp Tyr
1               5                   10                  15
```

<210> SEQ ID NO 74
<211> LENGTH: 126
<212> TYPE: PRT
<213> ORGANISM: Artificial Sequence
<220> FEATURE:
<223> OTHER INFORMATION: Synthetic Construct

<400> SEQUENCE: 74

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Thr Ile Tyr Phe Ser Gly Asn Thr Tyr Tyr Asn Pro Ser
        50                  55                  60

Leu Lys Ser Arg Val Thr Ile Ser Val Asp Thr Ser Lys Ser Gln Leu
65                  70                  75                  80

Ser Leu Lys Leu Asn Ser Val Thr Ala Ala Asp Thr Ala Val Tyr Tyr
                85                  90                  95

Cys Ala Arg Leu Arg Val Thr Met Val Arg Gly Val Ile Ile Gly Val
                100                 105                 110

Phe Asp Tyr Trp Gly Gln Gly Thr Leu Val Thr Val Ser Ser
            115                 120                 125
```

<210> SEQ ID NO 75
<211> LENGTH: 17
<212> TYPE: PRT
<213> ORGANISM: Artificial Sequence
<220> FEATURE:
<223> OTHER INFORMATION: Synthetic Construct

<400> SEQUENCE: 75

```
Lys Ser Ser Gln Ser Val Leu Tyr Ser Ser Asn Asn Lys Asn Tyr Leu
1               5                   10                  15

Ala
```

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Gln Gln Tyr Tyr Ser Thr Pro Pro Thr
1               5

<210> SEQ ID NO 77
<211> LENGTH: 113
<212> TYPE: PRT
<213> ORGANISM: Artificial Sequence
<220> FEATURE:
<223> OTHER INFORMATION: Synthetic Construct

<400> SEQUENCE: 77

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys

<210> SEQ ID NO 78
<211> LENGTH: 10
<212> TYPE: PRT
<213> ORGANISM: Artificial Sequence
<220> FEATURE:
<223> OTHER INFORMATION: Synthetic Construct

<400> SEQUENCE: 78

Gly Phe Thr Phe Ser Thr Tyr Ala Met Asn
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic Construct

<400> SEQUENCE: 79

Val Asp Val Val Ala Arg Tyr Tyr Gly Met Asp Val
1               5                   10

<210> SEQ ID NO 80
<211> LENGTH: 121
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Ala Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asp Val Val Ala Arg Tyr Tyr Gly Met Asp Val Trp Gly
            100                 105                 110

Gln Gly Thr Thr Val Thr Val Ser Ser
        115                 120

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Arg Ala Ser Gln Ser Ile Ser Gly Trp Leu Ala
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Glu Ala Ser Ser Leu Glu Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

Gln Gln Tyr Lys Ser Tyr Ser Trp Thr
1               5

<210> SEQ ID NO 84
<211> LENGTH: 107
<212> TYPE: PRT
<213> ORGANISM: Artificial Sequence
<220> FEATURE:
<223> OTHER INFORMATION: Synthetic Construct

<400> SEQUENCE: 84

Asp Ile Gln Met Thr Gln Ser Pro Ser Thr Leu Ser Ala Ser Val Gly
1               5                   10                  15

```
Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ser Trp
                85                  90                  95

Thr Phe Gly Gln Gly Thr Lys Val Glu Ile Lys
            100                 105

<210> SEQ ID NO 85
<211> LENGTH: 17
<212> TYPE: PRT
<213> ORGANISM: Artificial Sequence
<220> FEATURE:
<223> OTHER INFORMATION: Synthetic Construct

<400> SEQUENCE: 85

Ala Ile Ser Gly Arg Gly Gly Ser Thr Tyr Tyr Thr Asp Ser Val Lys
1               5                   10                  15

Gly

<210> SEQ ID NO 86
<211> LENGTH: 13
<212> TYPE: PRT
<213> ORGANISM: Artificial Sequence
<220> FEATURE:
<223> OTHER INFORMATION: Synthetic Construct

<400> SEQUENCE: 86

Asp Leu Gln Trp Phe Gly Glu Ser Thr Leu Phe Asp Tyr
1               5                   10

<210> SEQ ID NO 87
<211> LENGTH: 122
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Ser Thr Tyr Tyr Thr Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ile Leu Arg Ala Glu Asp Thr Ala Val Tyr Tyr Cys
                85                  90                  95

Ala Arg Asp Leu Gln Trp Phe Gly Glu Ser Thr Leu Phe Asp Tyr Trp
            100                 105                 110

Gly Gln Gly Thr Leu Val Thr Val Ser Ser
            115                 120
```

<210> SEQ ID NO 88
<211> LENGTH: 11
<212> TYPE: PRT
<213> ORGANISM: Artificial Sequence
<220> FEATURE:
<223> OTHER INFORMATION: Synthetic Construct

<400> SEQUENCE: 88

Arg Ala Ser Gln Ser Ile Ser Ala Trp Leu Ala
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Gln Gln Tyr Asn Ser Tyr Ser Arg Ser
1               5

<210> SEQ ID NO 90
<211> LENGTH: 107
<212> TYPE: PRT
<213> ORGANISM: Artificial Sequence
<220> FEATURE:
<223> OTHER INFORMATION: Synthetic Construct

<400> SEQUENCE: 90

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ala Trp
            20                  25                  30

Leu Ala Trp Phe Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Ser Phe Gly Gln Gly Thr Lys Leu Glu Ile Lys
            100                 105

<210> SEQ ID NO 91
<211> LENGTH: 10
<212> TYPE: PRT
<213> ORGANISM: Artificial Sequence
<220> FEATURE:
<223> OTHER INFORMATION: Synthetic Construct

<400> SEQUENCE: 91

Gly Phe Thr Phe Ser Ser Tyr Ala Leu Ser
1               5                   10

<210> SEQ ID NO 92
<211> LENGTH: 17
<212> TYPE: PRT
<213> ORGANISM: Artificial Sequence
<220> FEATURE:
<223> OTHER INFORMATION: Synthetic Construct -continued

<400> SEQUENCE: 92

Thr Ile Asn Val Gly Gly Val Asp Thr Asn Tyr Ala Gly Ser Val Lys
1               5                   10                  15

Gly

<210> SEQ ID NO 93
<211> LENGTH: 16
<212> TYPE: PRT
<213> ORGANISM: Artificial Sequence
<220> FEATURE:
<223> OTHER INFORMATION: Synthetic Construct

<400> SEQUENCE: 93

Ala Arg Ile Thr Met Val Arg Gly Val Ile Ile Pro Leu Phe Asp Tyr
1               5                   10                  15

<210> SEQ ID NO 94
<211> LENGTH: 125
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Ser Thr Ile Asn Val Gly Gly Val Asp Thr Asn Tyr Ala Gly Ser Val
    50                  55                  60

Lys Gly Arg Phe Thr Ile Ser Arg Asp Asn Pro Lys Asn Thr Leu Cys
65                  70                  75                  80

Leu Gln Met Asn Ser Leu Arg Ala Glu Asp Thr Ala Val Tyr His Cys
                85                  90                  95

Ala Lys Ala Arg Ile Thr Met Val Arg Gly Val Ile Ile Pro Leu Phe
            100                 105                 110

Asp Tyr Trp Gly Gln Gly Thr Leu Val Thr Val Ala Ser
        115                 120                 125

<210> SEQ ID NO 95
<211> LENGTH: 9
<212> TYPE: PRT
<213> ORGANISM: Artificial Sequence
<220> FEATURE:
<223> OTHER INFORMATION: Synthetic Construct

<400> SEQUENCE: 95

Gln Gln Phe Tyr Ser Thr Pro Val Thr
1               5

<210> SEQ ID NO 96
<211> LENGTH: 113
<212> TYPE: PRT
<213> ORGANISM: Artificial Sequence
<220> FEATURE:
<223> OTHER INFORMATION: Synthetic Construct

<400> SEQUENCE: 96

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Thr Pro Val Thr Phe Gly Gly Gly Thr Lys Val Glu Ile
            100                 105                 110

Lys

<210> SEQ ID NO 97
<211> LENGTH: 12
<212> TYPE: PRT
<213> ORGANISM: Artificial Sequence
<220> FEATURE:
<223> OTHER INFORMATION: Synthetic Construct

<400> SEQUENCE: 97

Thr Gly Ser Ile Ser Ser Ser Ser Tyr Tyr Trp Gly
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Synthetic Construct

<400> SEQUENCE: 98

Thr Ile Tyr Phe Ser Gly Ser Thr Tyr Tyr Asn Pro Ser Leu Lys Ser
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic Construct

<400> SEQUENCE: 99

Leu Arg Val Thr Met Val Arg Gly Val Ile Ile Gly Val Phe Asp Phe
1               5                   10                  15

<210> SEQ ID NO 100
<211> LENGTH: 126
<212> TYPE: PRT
<213> ORGANISM: Artificial Sequence
<220> FEATURE:
<223> OTHER INFORMATION: Synthetic Construct

<400> SEQUENCE: 100

Gln Val Gln Leu Gln Glu Ser Gly Pro Gly Leu Val Lys Pro Ser Glu
1               5                   10                  15

Thr Leu Ser Leu Thr Cys Thr Val Ser Thr Gly Ser Ile Ser Ser Ser
            20                  25                  30

Ser Tyr Tyr Trp Gly Trp Ile Arg Gln Pro Pro Gly Lys Gly Leu Glu
        35                  40                  45
```

```
Trp Ile Gly Thr Ile Tyr Phe Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Thr Ser Val Thr Ala Ala Asp Thr Ala Val Tyr Tyr
                 85                  90                  95

Cys Ala Arg Leu Arg Val Thr Met Val Arg Gly Val Ile Ile Gly Val
            100                 105                 110

Phe Asp Phe Trp Gly Gln Gly Thr Leu Val Thr Val Ser Ser
            115                 120                 125

<210> SEQ ID NO 101
<211> LENGTH: 10
<212> TYPE: PRT
<213> ORGANISM: Artificial Sequence
<220> FEATURE:
<223> OTHER INFORMATION: Synthetic Construct

<400> SEQUENCE: 101

Gly Gly Ser Phe Ser Gly Tyr Phe Trp Ser
 1               5                  10

<210> SEQ ID NO 102
<211> LENGTH: 16
<212> TYPE: PRT
<213> ORGANISM: Artificial Sequence
<220> FEATURE:
<223> OTHER INFORMATION: Synthetic Construct

<400> SEQUENCE: 102

Glu Phe Asn His Ser Gly Gly Thr Asn Ser Asn Pro Ser Leu Lys Ser
 1               5                  10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Construct

<400> SEQUENCE: 103

Ala Gly Gly Asp Tyr Gly Phe Tyr Tyr Tyr Gly Leu Asp Val
 1               5                  10                  15

<210> SEQ ID NO 104
<211> LENGTH: 123
<212> TYPE: PRT
<213> ORGANISM: Artificial Sequence
<220> FEATURE:
<223> OTHER INFORMATION: Synthetic Construct

<400> SEQUENCE: 104

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Phe Trp Ser Trp Ile Arg Gln Pro Pro Gly Lys Gly Leu Glu Trp Ile
             35                  40                  45

Gly Glu Phe Asn His Ser Gly Gly Thr Asn Ser Asn Pro Ser Leu Lys
         50                  55                  60

Ser Arg Val Thr Met Ser Val Asp Thr Ser Lys Asn Gln Phe Ser Leu
 65                  70                  75                  80
```

```
Lys Leu Ser Ser Val Thr Ala Ala Asp Thr Ala Val Tyr Phe Cys Ala
            85                  90                  95

Arg Ala Gly Gly Asp Tyr Gly Phe Tyr Tyr Tyr Tyr Gly Leu Asp Val
        100                 105                 110

Trp Gly Gln Gly Thr Thr Val Thr Val Ser Ser
        115                 120
```

<210> SEQ ID NO 105
<211> LENGTH: 19
<212> TYPE: PRT
<213> ORGANISM: Artificial Sequence
<220> FEATURE:
<223> OTHER INFORMATION: Synthetic Construct

<400> SEQUENCE: 105

```
Phe Ile Arg Asn Gln Ala Arg Gly Tyr Thr Ser Asp His Asn Pro Ser
1               5                   10                  15

Val Lys Gly
```

<210> SEQ ID NO 106
<211> LENGTH: 121
<212> TYPE: PRT
<213> ORGANISM: Artificial Sequence
<220> FEATURE:
<223> OTHER INFORMATION: Synthetic Construct

<400> SEQUENCE: 106

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120
```

<210> SEQ ID NO 107
<211> LENGTH: 17
<212> TYPE: PRT
<213> ORGANISM: Artificial Sequence
<220> FEATURE:
<223> OTHER INFORMATION: Synthetic Construct

<400> SEQUENCE: 107

```
Thr Ser Ser Gln Ser Leu Phe Asn Val Arg Ser Gln Lys Asn Tyr Leu
1               5                   10                  15

Ala
```

<210> SEQ ID NO 108
<211> LENGTH: 112
<212> TYPE: PRT
<213> ORGANISM: Artificial Sequence
<220> FEATURE:

<223> OTHER INFORMATION: Synthetic Construct

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 109
<211> LENGTH: 19
<212> TYPE: PRT
<213> ORGANISM: Artificial Sequence
<220> FEATURE:
<223> OTHER INFORMATION: Synthetic Construct

<400> SEQUENCE: 109

Phe Ile Arg Asn Gln Asp Arg Gly Tyr Thr Ser Asp His Gln Pro Ser
1               5                   10                  15

Val Lys Gly

<210> SEQ ID NO 110
<211> LENGTH: 121
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Asp Arg Gly Tyr Thr Ser Asp His Gln Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 111
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 111

Thr Ser Asp Gln Ser Leu Phe Asn Val Arg Ser Gly Lys Asn Tyr Leu
1               5                   10                  15

Ala

<210> SEQ ID NO 112
<211> LENGTH: 7
<212> TYPE: PRT
<213> ORGANISM: Artificial Sequence
<220> FEATURE:
<223> OTHER INFORMATION: Synthetic Construct

<400> SEQUENCE: 112

Trp Ala Ser Asp Arg Glu Ser
1               5

<210> SEQ ID NO 113
<211> LENGTH: 112
<212> TYPE: PRT
<213> ORGANISM: Artificial Sequence
<220> FEATURE:
<223> OTHER INFORMATION: Synthetic Construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Thr Ser Asp Gln Ser Leu Phe Asn Val
                20                  25                  30

Arg Ser Gly Lys Asn Tyr Leu Ala Trp Tyr Gln Gln Lys Pro Gly Lys
            35                  40                  45

Ala Pro Lys Leu Leu Ile Tyr Trp Ala Ser Asp Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Asp Arg His Ser Tyr Tyr Val Leu Asp Tyr
1               5                   10

<210> SEQ ID NO 115
<211> LENGTH: 121
<212> TYPE: PRT
<213> ORGANISM: Artificial Sequence
<220> FEATURE:
<223> OTHER INFORMATION: Synthetic Construct

<400> SEQUENCE: 115

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg His Ser Tyr Tyr Val Leu Asp Tyr Trp Gly
            100                 105                 110

Gln Gly Thr Thr Val Thr Val Ser Ser
        115                 120

<210> SEQ ID NO 116
<211> LENGTH: 8
<212> TYPE: PRT
<213> ORGANISM: Artificial Sequence
<220> FEATURE:
<223> OTHER INFORMATION: Synthetic Construct

<400> SEQUENCE: 116

Lys Gln Ser Tyr Tyr Leu Phe Thr
1               5

<210> SEQ ID NO 117
<211> LENGTH: 112
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
            20                  25                  30

Arg Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Tyr Leu Phe Thr Phe Gly Gly Gly Thr Lys Val Glu Ile Lys
            100                 105                 110

<210> SEQ ID NO 118
<211> LENGTH: 107
<212> TYPE: PRT
<213> ORGANISM: Artificial Sequence
<220> FEATURE:
<223> OTHER INFORMATION: Synthetic Construct

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 120
<211> LENGTH: 117
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asn His Ser Gly Ser Thr Lys Tyr Asn Pro Ser Leu Lys
    50                  55                  60

Ser Arg Phe Thr Ile Ser Gly Asp Asn Ala Lys Asn Ser Phe Tyr Leu
65                  70                  75                  80

Gln Met Asn Ser Leu Arg Ala Glu Asp Thr Ala Val Tyr Tyr Cys Val
                85                  90                  95

Arg Gly Leu Tyr Asn Trp Asn Val Asp Ser Trp Gly Gln Gly Thr Leu
            100                 105                 110

```
Val Thr Val Ser Ser
        115

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 122
<211> LENGTH: 107
<212> TYPE: PRT
<213> ORGANISM: Artificial Sequence
<220> FEATURE:
<223> OTHER INFORMATION: Synthetic Construct

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Arg Ser Trp
            20                  25                  30

Leu Ala Trp Phe Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 124
<211> LENGTH: 117
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Val Arg Gln Ala Pro Gly Lys Gly Leu Glu Trp Val
        35                  40                  45

Ala Glu Ile Asn His Ser Gly Ser Ala Thr Tyr Asn Pro Ser Leu Lys
50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
        115

<210> SEQ ID NO 125
<211> LENGTH: 117
<212> TYPE: PRT
<213> ORGANISM: Artificial Sequence
<220> FEATURE:
<223> OTHER INFORMATION: Synthetic Construct

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asn His Ser Gly Ser Ala Thr Tyr Asn Pro Ser Leu Lys
50                  55                  60

Ser Arg Phe Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
                100                 105                 110

Val Thr Val Ser Ser
        115

<210> SEQ ID NO 126
<211> LENGTH: 107
<212> TYPE: PRT
<213> ORGANISM: Artificial Sequence
<220> FEATURE:
<223> OTHER INFORMATION: Synthetic Construct

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gly Gly Thr Lys Val Glu Ile Lys
            100                 105

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct

<400> SEQUENCE: 127

Gly Gly Ser Phe Ser Gly Tyr Tyr Trp Ser
1               5                   10

<210> SEQ ID NO 128
<211> LENGTH: 117
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Phe Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gln Gly Thr Leu
            100                 105                 110

Val Thr Val Ser Ser
        115

<210> SEQ ID NO 129
<211> LENGTH: 117
<212> TYPE: PRT
<213> ORGANISM: Artificial Sequence
<220> FEATURE:
<223> OTHER INFORMATION: Synthetic Construct

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Phe Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gln Gly Thr Leu
            100                 105                 110

Val Thr Val Ser Ser
        115

<210> SEQ ID NO 130
<211> LENGTH: 16
<212> TYPE: PRT
<213> ORGANISM: Artificial Sequence
<220> FEATURE:
<223> OTHER INFORMATION: Synthetic Construct

<400> SEQUENCE: 130

Glu Ile Asp His Gln Gly Ser Thr Lys Tyr Asn Pro Ser Leu Lys Ser
1               5                   10                  15

<210> SEQ ID NO 131
<211> LENGTH: 117
<212> TYPE: PRT
<213> ORGANISM: Artificial Sequence
<220> FEATURE:
<223> OTHER INFORMATION: Synthetic Construct

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asp His Gln Gly Ser Thr Lys Tyr Asn Pro Ser Leu Lys
    50                  55                  60

Ser Arg Phe Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala

```
                85                  90                  95
Arg Gly Leu Tyr Asn Trp Asn Val Asp His Trp Gly Gln Gly Thr Leu
            100                 105                 110

Val Thr Val Ser Ser
        115

<210> SEQ ID NO 132
<211> LENGTH: 117
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
        115

<210> SEQ ID NO 133
<211> LENGTH: 117
<212> TYPE: PRT
<213> ORGANISM: Artificial Sequence
<220> FEATURE:
<223> OTHER INFORMATION: Synthetic Construct

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Val Arg Gln Ala Pro Gly Lys Gly Leu Glu Trp Val
        35                  40                  45

Ala Glu Ile Asn His Ser Gly Ser Ala Thr Tyr Asn Pro Ser Leu Lys
    50                  55                  60

Ser Arg Phe Thr Ile Ser Arg Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
        115

<210> SEQ ID NO 134
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 134

Glu Ile Asn His Ser Gly Ser Ala Thr Tyr Val Asp Ser Val Lys Gly
1               5                   10                  15

<210> SEQ ID NO 135
<211> LENGTH: 117
<212> TYPE: PRT
<213> ORGANISM: Artificial Sequence
<220> FEATURE:
<223> OTHER INFORMATION: Synthetic Construct

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asn His Ser Gly Ser Ala Thr Tyr Val Asp Ser Val Lys
    50                  55                  60

Gly Arg Phe Thr Ile Ser Arg Asp Thr Ala Lys Asn Ser Phe Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
        115

<210> SEQ ID NO 136
<211> LENGTH: 9
<212> TYPE: PRT
<213> ORGANISM: Artificial Sequence
<220> FEATURE:
<223> OTHER INFORMATION: Synthetic Construct

<400> SEQUENCE: 136

Glu Leu Tyr Asn Trp Asn Val Asp His
1               5

<210> SEQ ID NO 137
<211> LENGTH: 117
<212> TYPE: PRT
<213> ORGANISM: Artificial Sequence
<220> FEATURE:
<223> OTHER INFORMATION: Synthetic Construct

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60
```

Ser Arg Phe Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
            85                  90                  95

Arg Glu Leu Tyr Asn Trp Asn Val Asp His Trp Gly Gln Gly Thr Leu
        100                 105                 110

Val Thr Val Ser Ser
        115

<210> SEQ ID NO 138
<211> LENGTH: 9
<212> TYPE: PRT
<213> ORGANISM: Artificial Sequence
<220> FEATURE:
<223> OTHER INFORMATION: Synthetic Construct

<400> SEQUENCE: 138

Leu Gln His Asn Ala Tyr Pro Arg Thr
1               5

<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ala Tyr Pro Arg
            85                  90                  95

Thr Phe Gly Gly Gly Thr Lys Val Glu Ile Lys
        100                 105

<210> SEQ ID NO 140
<211> LENGTH: 9
<212> TYPE: PRT
<213> ORGANISM: Artificial Sequence
<220> FEATURE:
<223> OTHER INFORMATION: Synthetic Construct

<400> SEQUENCE: 140

Leu Gln His Ser Ser Tyr Pro Arg Thr
1               5

<210> SEQ ID NO 141
<211> LENGTH: 107
<212> TYPE: PRT
<213> ORGANISM: Artificial Sequence
<220> FEATURE:
<223> OTHER INFORMATION: Synthetic Construct

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Leu Gln His Ser Ser Tyr Pro Arg
                85                  90                  95

Thr Phe Gly Gly Gly Thr Lys Val Glu Ile Lys
            100                 105
```

<210> SEQ ID NO 142
<211> LENGTH: 9
<212> TYPE: PRT
<213> ORGANISM: Artificial Sequence
<220> FEATURE:
<223> OTHER INFORMATION: Synthetic Construct

<400> SEQUENCE: 142

```
Leu Gln His Gln Ser Tyr Pro Arg Thr
1               5
```

<210> SEQ ID NO 143
<211> LENGTH: 107
<212> TYPE: PRT
<213> ORGANISM: Artificial Sequence
<220> FEATURE:
<223> OTHER INFORMATION: Synthetic Construct

<400> SEQUENCE: 143

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Leu Gln His Gln Ser Tyr Pro Arg
                85                  90                  95

Thr Phe Gly Gly Gly Thr Lys Val Glu Ile Lys
            100                 105
```

<210> SEQ ID NO 144
<211> LENGTH: 9
<212> TYPE: PRT
<213> ORGANISM: Artificial Sequence
<220> FEATURE:
<223> OTHER INFORMATION: Synthetic Construct

<400> SEQUENCE: 144

```
Leu Gln His Ala Ser Tyr Pro Arg Thr
1               5
```

<210> SEQ ID NO 145
<211> LENGTH: 107
<212> TYPE: PRT
<213> ORGANISM: Artificial Sequence
<220> FEATURE:
<223> OTHER INFORMATION: Synthetic Construct

<400> SEQUENCE: 145

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Ala Ser Tyr Pro Arg
                85                  90                  95

Thr Phe Gly Gly Gly Thr Lys Val Glu Ile Lys
            100                 105
```

<210> SEQ ID NO 146
<211> LENGTH: 9
<212> TYPE: PRT
<213> ORGANISM: Artificial Sequence
<220> FEATURE:
<223> OTHER INFORMATION: Synthetic Construct

<400> SEQUENCE: 146

```
Leu Gln His Asn Ala Tyr Pro Tyr Thr
1               5
```

<210> SEQ ID NO 147
<211> LENGTH: 107
<212> TYPE: PRT
<213> ORGANISM: Artificial Sequence
<220> FEATURE:
<223> OTHER INFORMATION: Synthetic Construct

<400> SEQUENCE: 147

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ala Tyr Pro Tyr
                85                  90                  95

Thr Phe Gly Gln Gly Thr Lys Leu Glu Ile Lys
            100                 105
```

<210> SEQ ID NO 148
<211> LENGTH: 9
<212> TYPE: PRT
<213> ORGANISM: Artificial Sequence
<220> FEATURE:
<223> OTHER INFORMATION: Synthetic Construct

<400> SEQUENCE: 148

Leu Gln His Gln Ser Tyr Pro Tyr Thr
1               5

<210> SEQ ID NO 149
<211> LENGTH: 107
<212> TYPE: PRT
<213> ORGANISM: Artificial Sequence
<220> FEATURE:
<223> OTHER INFORMATION: Synthetic Construct

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Gln Ser Tyr Pro Tyr
                85                  90                  95

Thr Phe Gly Gln Gly Thr Lys Leu Glu Ile Lys
            100                 105

<210> SEQ ID NO 150
<211> LENGTH: 9
<212> TYPE: PRT
<213> ORGANISM: Artificial Sequence
<220> FEATURE:
<223> OTHER INFORMATION: Synthetic Construct

<400> SEQUENCE: 150

Leu Gln His Ala Ser Tyr Pro Tyr Thr
1               5

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Ala Ser Tyr Pro Tyr
                85                  90                  95

```
Thr Phe Gly Gln Gly Thr Lys Leu Glu Ile Lys
            100                 105

<210> SEQ ID NO 152
<211> LENGTH: 11
<212> TYPE: PRT
<213> ORGANISM: Artificial Sequence
<220> FEATURE:
<223> OTHER INFORMATION: Synthetic Construct

<400> SEQUENCE: 152

Arg Ala Ser Gln Ser Thr Arg Ser Trp Leu Ala
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Gln Gln Tyr Gly Ser Tyr Ser Arg Thr
1               5

<210> SEQ ID NO 154
<211> LENGTH: 107
<212> TYPE: PRT
<213> ORGANISM: Artificial Sequence
<220> FEATURE:
<223> OTHER INFORMATION: Synthetic Construct

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Ser Arg
                85                  90                  95

Thr Phe Gly Gln Gly Thr Lys Val Glu Ile Lys
            100                 105

<210> SEQ ID NO 155
<211> LENGTH: 117
<212> TYPE: PRT
<213> ORGANISM: Artificial Sequence
<220> FEATURE:
<223> OTHER INFORMATION: Synthetic Construct

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45
```

Gly Glu Ile Asp His Gln Gly Ser Thr Lys Tyr Asn Pro Ser Leu Lys
            50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
            115

<210> SEQ ID NO 156
<211> LENGTH: 117
<212> TYPE: PRT
<213> ORGANISM: Artificial Sequence
<220> FEATURE:
<223> OTHER INFORMATION: Synthetic Construct

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Ile Arg Gln Pro Pro Gly Lys Gly Leu Glu Trp Ile
            35                  40                  45

Gly Glu Ile Asp His Gln Gly Ser Thr Lys Tyr Asn Pro Ser Leu Lys
            50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Glu Leu Tyr Asn Trp Asn Val Asp His Trp Gly Gln Gly Thr Leu
            100                 105                 110

Val Thr Val Ser Ser
            115

<210> SEQ ID NO 157
<211> LENGTH: 117
<212> TYPE: PRT
<213> ORGANISM: Artificial Sequence
<220> FEATURE:
<223> OTHER INFORMATION: Synthetic Construct

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Ile Arg Gln Pro Pro Gly Lys Gly Leu Glu Trp Ile
            35                  40                  45

Gly Glu Ile Asp His Gln Gly Ser Thr Lys Tyr Asn Pro Ser Leu Lys
            50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Glu Leu Tyr Asn Trp Asn Val Asp His Trp Gly Gln Gly Thr Leu

```
                100                 105                 110

Val Thr Val Ser Ser
        115

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

Ala Ile Ser Gly Gly Gly Gly Ser Thr Gln Tyr Ala Asp Ser Val Lys
1               5                   10                  15

Gly

<210> SEQ ID NO 159
<211> LENGTH: 122
<212> TYPE: PRT
<213> ORGANISM: Artificial Sequence
<220> FEATURE:
<223> OTHER INFORMATION: Synthetic Construct

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Gly Ser Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gln Trp Phe Gly Glu Ser Thr Leu Phe Asp Tyr Trp
            100                 105                 110

Gly Gln Gly Thr Leu Val Thr Val Ser Ser
        115                 120

<210> SEQ ID NO 160
<211> LENGTH: 13
<212> TYPE: PRT
<213> ORGANISM: Artificial Sequence
<220> FEATURE:
<223> OTHER INFORMATION: Synthetic Construct

<400> SEQUENCE: 160

Asp Ile Gln Trp Tyr Gly Glu Ser Thr Leu Phe Asp Tyr
1               5                   10

<210> SEQ ID NO 161
<211> LENGTH: 122
<212> TYPE: PRT
<213> ORGANISM: Artificial Sequence
<220> FEATURE:
<223> OTHER INFORMATION: Synthetic Construct

<400> SEQUENCE: 161

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Ser Gly Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Ile Gln Trp Tyr Gly Glu Ser Thr Leu Phe Asp Tyr Trp
            100                 105                 110

Gly Gln Gly Thr Leu Val Thr Val Ser Ser
        115                 120

<210> SEQ ID NO 162
<211> LENGTH: 13
<212> TYPE: PRT
<213> ORGANISM: Artificial Sequence
<220> FEATURE:
<223> OTHER INFORMATION: Synthetic Construct

<400> SEQUENCE: 162

Asp Ile Gln Trp His Gly Glu Ser Thr Leu Phe Asp Tyr
 1               5                  10

<210> SEQ ID NO 163
<211> LENGTH: 122
<212> TYPE: PRT
<213> ORGANISM: Artificial Sequence
<220> FEATURE:
<223> OTHER INFORMATION: Synthetic Construct

<400> SEQUENCE: 163

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Ser Gly Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Ile Gln Trp His Gly Glu Ser Thr Leu Phe Asp Tyr Trp
            100                 105                 110

Gly Gln Gly Thr Leu Val Thr Val Ser Ser
        115                 120

<210> SEQ ID NO 164
<211> LENGTH: 13
<212> TYPE: PRT
<213> ORGANISM: Artificial Sequence
<220> FEATURE:
<223> OTHER INFORMATION: Synthetic Construct

<400> SEQUENCE: 164
```

Asp Ile Gln Trp Phe Gly Arg Ser Thr Leu Phe Asp Tyr
1               5                   10

<210> SEQ ID NO 165
<211> LENGTH: 122
<212> TYPE: PRT
<213> ORGANISM: Artificial Sequence
<220> FEATURE:
<223> OTHER INFORMATION: Synthetic Construct

<400> SEQUENCE: 165

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gln Trp Phe Gly Arg Ser Thr Leu Phe Asp Tyr Trp
            100                 105                 110

Gly Gln Gly Thr Leu Val Thr Val Ser Ser
        115                 120

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Arg Ala Ser Gln Ser Thr Arg Ser His Leu Ala
1               5                   10

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Arg Ser His
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Ser Arg
                85                  90                  95

Thr Phe Gly Gln Gly Thr Lys Val Glu Ile Lys

<210> SEQ ID NO 168
<211> LENGTH: 107
<212> TYPE: PRT
<213> ORGANISM: Artificial Sequence
<220> FEATURE:
<223> OTHER INFORMATION: Synthetic Construct

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Ser Arg
                85                  90                  95

Thr Phe Gly Gln Gly Thr Lys Val Glu Ile Lys
            100                 105

<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Arg Ser Trp
            20                  25                  30

Leu Ala Trp His Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Ser Arg
                85                  90                  95

Thr Phe Gly Gln Gly Thr Lys Val Glu Ile Lys
            100                 105

<210> SEQ ID NO 170
<211> LENGTH: 107
<212> TYPE: PRT
<213> ORGANISM: Artificial Sequence
<220> FEATURE:
<223> OTHER INFORMATION: Synthetic Construct

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Arg Ser Trp
            20                  25                  30

Leu Ala Trp Leu Gln Gln Lys Pro Gly Lys Ala Pro Lys Leu Leu Ile
          35                  40                  45

Tyr Lys Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Ser Arg
                 85                  90                  95

Thr Phe Gly Gln Gly Thr Lys Val Glu Ile Lys
                100                 105

<210> SEQ ID NO 171
<211> LENGTH: 117
<212> TYPE: PRT
<213> ORGANISM: Artificial Sequence
<220> FEATURE:
<223> OTHER INFORMATION: Synthetic Construct

<400> SEQUENCE: 171

Glu Val Gln Leu Val Glu Ser Gly Gly Gly Leu Val Gln Pro Gly Gly
1                5                  10                  15

Ser Leu Arg Leu Ser Cys Ala Val Ser Gly Gly Ser Phe Ser Gly Tyr
                 20                  25                  30

Tyr Trp Asn Trp Ile Arg Gln Pro Pro Gly Lys Gly Leu Glu Trp Ile
             35                  40                  45

Gly Glu Ile Asn His Ser Gly Ser Ala Thr Tyr Asn Pro Ser Leu Lys
     50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                 85                  90                  95

Arg Gly Leu Tyr Asn Trp Asn Val Asp His Trp Gly Gln Gly Thr Leu
            100                 105                 110

Val Thr Val Ser Ser
            115

<210> SEQ ID NO 172
<211> LENGTH: 117
<212> TYPE: PRT
<213> ORGANISM: Artificial Sequence
<220> FEATURE:
<223> OTHER INFORMATION: Synthetic Construct

<400> SEQUENCE: 172

Glu Val Gln Leu Val Glu Ser Gly Gly Gly Leu Val Gln Pro Gly Gly
1                5                  10                  15

Ser Leu Arg Leu Ser Cys Ala Val Ser Gly Gly Ser Phe Ser Gly Tyr
                 20                  25                  30

Tyr Trp Asn Trp Val Arg Gln Ala Pro Gly Lys Gly Leu Glu Trp Ile
             35                  40                  45

Gly Glu Ile Asn His Ser Gly Ser Ala Thr Tyr Asn Pro Ser Leu Lys
     50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                 85                  90                  95

Arg Gly Leu Tyr Asn Trp Asn Val Asp His Trp Gly Gln Gly Thr Leu

Val Thr Val Ser Ser
        115

<210> SEQ ID NO 173
<211> LENGTH: 117
<212> TYPE: PRT
<213> ORGANISM: Artificial Sequence
<220> FEATURE:
<223> OTHER INFORMATION: Synthetic Construct

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asp His Gln Gly Ser Thr Lys Tyr Asn Pro Ser Leu Lys
    50                  55                  60

Ser Arg Val Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
            85                  90                  95

Arg Gly Leu Tyr Asn Trp Asn Val Asp His Trp Gly Gln Gly Thr Leu
        100                 105                 110

Val Thr Val Ser Ser
        115

<210> SEQ ID NO 174
<211> LENGTH: 117
<212> TYPE: PRT
<213> ORGANISM: Artificial Sequence
<220> FEATURE:
<223> OTHER INFORMATION: Synthetic Construct

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Val Arg Gln Ala Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Gly Leu Tyr Asn Trp Asn Val Asp His Trp Gly Gln Gly Thr Leu
        100                 105                 110

Val Thr Val Ser Ser
        115

<210> SEQ ID NO 175
<211> LENGTH: 117
<212> TYPE: PRT
<213> ORGANISM: Artificial Sequence
<220> FEATURE:

-continued

<223> OTHER INFORMATION: Synthetic Construct

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ala Lys Asn Ser Phe Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
        115

<210> SEQ ID NO 176
<211> LENGTH: 117
<212> TYPE: PRT
<213> ORGANISM: Artificial Sequence
<220> FEATURE:
<223> OTHER INFORMATION: Synthetic Construct

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Leu Tyr Asn Trp Asn Val Asp His Trp Gly Gln Gly Thr Leu
            100                 105                 110

Val Thr Val Ser Ser
        115

<210> SEQ ID NO 177
<211> LENGTH: 326
<212> TYPE: PRT
<213> ORGANISM: Artificial Sequence
<220> FEATURE:
<223> OTHER INFORMATION: Synthetic Construct

<400> SEQUENCE: 177

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Glu Val Glu Cys Pro Glu Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Glu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 178
<211> LENGTH: 326
<212> TYPE: PRT
<213> ORGANISM: Artificial Sequence
<220> FEATURE:
<223> OTHER INFORMATION: Synthetic Construct

<400> SEQUENCE: 178

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
```

```
            65                  70                  75                  80
Tyr Thr Cys Asn Val Asp His Lys Pro Ser Asn Thr Lys Val Asp Lys
                85                  90                  95

Thr Val Glu Arg Lys Cys Arg Val Arg Cys Pro Arg Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Ala
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 179
<211> LENGTH: 329
<212> TYPE: PRT
<213> ORGANISM: Artificial Sequence
<220> FEATURE:
<223> OTHER INFORMATION: Synthetic Construct

<400> SEQUENCE: 179

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110
Pro Ala Pro Glu Ala Ala Gly Ala Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 180
<211> LENGTH: 325
<212> TYPE: PRT
<213> ORGANISM: Artificial Sequence
<220> FEATURE:
<223> OTHER INFORMATION: Synthetic Construct

<400> SEQUENCE: 180

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Arg Val Arg Cys Pro Arg Cys Pro Ala Pro
            100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Ala
```

```
            130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 181
<211> LENGTH: 325
<212> TYPE: PRT
<213> ORGANISM: Artificial Sequence
<220> FEATURE:
<223> OTHER INFORMATION: Synthetic Construct

<400> SEQUENCE: 181

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Glu Val Glu Cys Pro Glu Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Glu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 182
<211> LENGTH: 329
<212> TYPE: PRT
<213> ORGANISM: Artificial Sequence
<220> FEATURE:
<223> OTHER INFORMATION: Synthetic Construct

<400> SEQUENCE: 182

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Arg Lys Thr His Thr Cys Pro Arg Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 183
<211> LENGTH: 329
<212> TYPE: PRT
<213> ORGANISM: Artificial Sequence
<220> FEATURE:
<223> OTHER INFORMATION: Synthetic Construct

<400> SEQUENCE: 183

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Glu Lys Thr His Thr Cys Pro Glu Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

```
                  225                 230                 235                 240

Met Thr Lys Asn Gln Val Ser Leu Thr Cys Glu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 184
<211> LENGTH: 329
<212> TYPE: PRT
<213> ORGANISM: Artificial Sequence
<220> FEATURE:
<223> OTHER INFORMATION: Synthetic Construct

<400> SEQUENCE: 184

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
            260                 265                 270
Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 185
<211> LENGTH: 329
<212> TYPE: PRT
<213> ORGANISM: Artificial Sequence
<220> FEATURE:
<223> OTHER INFORMATION: Synthetic Construct

<400> SEQUENCE: 185

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Glu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                  290             295             300
    Val Phe Ser Cys Ser Val Met His Glu Ala Leu His Asn His Tyr Thr
    305                 310                 315                 320

Gln Lys Ser Leu Ser Leu Ser Pro Gly
                        325

<210> SEQ ID NO 186
<211> LENGTH: 443
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Glu Ser Gly Gly Gly Leu Val Gln Pro Gly Gly
    1               5                   10                  15

Ser Leu Arg Leu Ser Cys Ala Val Ser Gly Gly Ser Phe Ser Gly Tyr
                20                  25                  30

Tyr Trp Asn Trp Val Arg Gln Ala Pro Gly Lys Gly Leu Glu Trp Ile
                35                  40                  45

Gly Glu Ile Asn His Ser Gly Ser Ala Thr Tyr Asn Pro Ser Leu Lys
    50                  55                  60

Ser Arg Val Thr Ile Ser Val Asp Thr Ala Lys Asn Ser Leu Tyr Leu
    65                  70                  75                  80

Gln Met Asn Ser Leu Arg Ala Glu Asp Thr Ala Val Tyr Tyr Cys Ala
                    85                  90                  95

Arg Gly Leu Tyr Asn Trp Asn Val Asp His Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
    145                 150                 155                 160

Gly Ala Leu Thr Ser Gly Val His Thr Phe Pro Ala Val Leu Gln Ser
                    165                 170                 175

Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
                195                 200                 205

Thr Lys Val Asp Lys Thr Val Glu Arg Lys Cys Glu Val Glu Cys Pro
    210                 215                 220

Glu Cys Pro Ala Pro Pro Val Ala Gly Pro Ser Val Phe Leu Phe Pro
    225                 230                 235                 240

Pro Lys Pro Lys Asp Thr Leu Met Ile Ser Arg Thr Pro Glu Val Thr
                    245                 250                 255

Cys Val Val Val Ala Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
                290                 295                 300

Val His Gln Asp Trp Leu Asn Gly Lys Glu Tyr Lys Cys Lys Val Ser
    305                 310                 315                 320

Asn Lys Gly Leu Pro Ser Ser Ile Glu Lys Thr Ile Ser Lys Thr Lys
```

325                 330                 335
Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Glu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
                435                 440

<210> SEQ ID NO 187
<211> LENGTH: 214
<212> TYPE: PRT
<213> ORGANISM: Artificial Sequence
<220> FEATURE:
<223> OTHER INFORMATION: Synthetic Construct

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ala Tyr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 188
<211> LENGTH: 447
<212> TYPE: PRT

<213> ORGANISM: Artificial Sequence
<220> FEATURE:
<223> OTHER INFORMATION: Synthetic Construct

<400> SEQUENCE: 188

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Gln Ala Arg Gly Tyr Thr Ser Asp His Asn Pro
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Arg
210                 215                 220

Val Arg Cys Pro Arg Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
```

```
                385                 390                 395                 400
Asp Gly Ser Phe Phe Leu Tyr Ser Arg Leu Thr Val Asp Lys Ser Arg
                    405                 410                 415

Trp Gln Gln Gly Asn Val Phe Ser Cys Ser Val Met His Glu Ala Leu
                    420                 425                 430

His Asn His Tyr Thr Gln Lys Ser Leu Ser Leu Ser Pro Gly Lys
                    435                 440                 445

<210> SEQ ID NO 189
<211> LENGTH: 219
<212> TYPE: PRT
<213> ORGANISM: Artificial Sequence
<220> FEATURE:
<223> OTHER INFORMATION: Synthetic Construct

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Thr Ser Ser Gln Ser Leu Phe Asn Val
                20                  25                  30

Arg Ser Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asp Leu Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 190
<211> LENGTH: 448
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30
```

-continued

Ala Met Ser Trp Val Arg Gln Ala Pro Gly Lys Gly Leu Glu Trp Val
            35                  40                  45
Ser Ala Ile Ser Gly Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Asp Ile Gln Trp Tyr Gly Glu Ser Thr Leu Phe Asp Tyr Trp
                    100                 105                 110
Gly Gln Gly Thr Leu Val Thr Val Ser Ser Ala Ser Thr Lys Gly Pro
            115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Asn Phe Gly Thr Gln Thr Tyr Thr Cys Asn Val Asp
        195                 200                 205
His Lys Pro Ser Asn Thr Lys Val Asp Lys Thr Val Glu Arg Lys Cys
    210                 215                 220
Glu Val Glu Cys Pro Glu Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Ala Val Ser His Glu Asp Pro
                260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Phe Arg Val Val
290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Glu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 191
<211> LENGTH: 214
<212> TYPE: PRT
<213> ORGANISM: Artificial Sequence
<220> FEATURE:
<223> OTHER INFORMATION: Synthetic Construct

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Arg Ser His
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Tyr Ser Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 192
<211> LENGTH: 1329
<212> TYPE: DNA
<213> ORGANISM: Artificial Sequence
<220> FEATURE:
<223> OTHER INFORMATION: Synthetic Construct

<400> SEQUENCE: 192
gaggtgcagc tggtggagtc tgggggaggc ttggtccagc ctggggggtc cctgagactc      60
tcctgtgcag tgtctggagg gtcctttagt ggttattact ggaactgggt cgccaggcc     120 ccagggaagg ggctggagtg gattggggaa ataaaccact ccggaagcgc acctataac     180 ccgtctctca agagtcgagt gaccatctcc gtagacacgg ccaagaactc actgtatctg     240
caaatgaaca gcctgagagc cgaggacacg gctgtgtatt actgtgcgag aggcctttac     300
aactggaacg tggaccactg gggccagggc accctggtca ccgtctcctc agcgtcgacc     360
aagggcccat cggtcttccc cctggcgccc tgctccagga gcacctccga gagcacagcg     420
gccctgggct gcctggtcaa ggactacttc cccgaaccgg tgacggtgtc gtggaactca     480
ggcgctctga ccagcggcgt gcacaccttc ccggctgtcc tacagtcctc aggactctac     540

```
tccctcagca gcgtagtgac cgtgccctcc agcaacttcg gcacccagac ctacacctgc    600
aacgtagatc acaagcccag caacaccaag gtggacaaga cagttgagcg caaatgtgag    660
gtcgagtgcc cagagtgccc agcaccacct gtggcaggac cgtcagtctt cctcttcccc    720
ccaaaaccca aggacacccct catgatctcc cggacccctg aggtcacgtg cgtggtggtg    780
gccgtgagcc acgaagaccc cgaggtccag ttcaactggt acgtggacgg cgtggaggtg    840
cataatgcca agacaaagcc acgggaggag cagttcaaca gcacgttccg tgtggtcagc    900
gtcctcaccg tcgtgcacca ggactggctg aacggcaagg agtacaagtg caaggtctcc    960
aacaaaggcc tcccatcctc catcgagaaa accatctcca aaccaaagg gcagccccga   1020 gaaccacagg tgtacaccct gcccccatcc cgggaggaga tgaccaagaa ccaggtcagc   1080
ctgacctgcg aggtcaaagg cttctacccc agcgacatcg ccgtggagtg ggagagcaat   1140
gggcagccgg agaacaacta caagaccaca cctcccatgc tggactccga cggctccttc   1200
ttcctctaca gcaagctcac cgtggacaag agcaggtggc agcaggggaa cgtcttctca   1260
tgctccgtga tgcatgaggc tctgcacaac cactacacac agaagagcct ctccctgtcc   1320
cccggaaaa                                                          1329

<210> SEQ ID NO 193
<211> LENGTH: 642
<212> TYPE: DNA
<213> ORGANISM: Artificial Sequence
<220> FEATURE:
<223> OTHER INFORMATION: Synthetic Construct

<400> SEQUENCE: 193
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtctacag cataatgcct acctcgcac tttcggcgga    300 gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 194
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 194
gaagtgcagc ttgtggagtc cggtggcgga ctcgtgcagc cgggcggatc cctgagactg     60
tcgtgtgccg catcaggatt caccttttcc gactattaca tgacctgggt ccgccaagct    120
cccgggaagg gcctggaatg ggtggccttc atccgcaacc aggcccgggg ctacacttcc    180
gatcacaacc ctagcgtgaa gggaaggttc accattcgc gggacaacgc gaagaattcc    240
ctgtacctcc aaatgaacag cctgcgggcc gaggacactg ccgtctacta ctgcgcccgc    300
```

```
gatagaccaa gctactacgt gttggactac tggggacagg ggaccacggt caccgtctcc    360
tcagcctcca ccaagggccc atcggtcttc ccctggcgc cctgctccag gagcacctcc     420
gagagcacag cggccctggg ctgcctggtc aaggactact ccccgaacc ggtgacggtg     480
tcgtggaact caggcgctct gaccagcggc gtgcacacct cccggctgt cctacagtcc     540
tcaggactct actccctcag cagcgtagtg accgtgccct ccagcaactt cggcacccag    600
acctacacct gcaacgtaga tcacaagccc agcaacacca aggtggacaa gacagttgag    660
cgcaaatgtc gtgtcaggtg cccaaggtgc ccagcaccac ctgtggcagg accgtcagtc    720
ttcctcttcc ccccaaaacc caaggacacc ctcatgatct cccggacccc tgaggtcacg    780
tgcgtggtgg tggccgtgag ccacgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgtcgtgcac caggactggc tgaacggcaa ggagtacaag    960
tgcaaggtct ccaacaaagg cctcccatcc tccatcgaga aaaccatctc caaaaccaaa    1020
gggcagcccc gagaaccaca ggtgtacacc ctgcccccat cccgggagga gatgaccaag    1080
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaggctc accgtggaca agagcaggtg gcagcagggg    1260
aacgtcttct catgctccgt gatgcatgag gctctgcaca accactacac acagaagagc    1320
ctctcccctgt ctccgggtaa a                                             1341
```

<210> SEQ ID NO 195
<211> LENGTH: 657
<212> TYPE: DNA
<213> ORGANISM: Artificial Sequence
<220> FEATURE:
<223> OTHER INFORMATION: Synthetic Construct

<400> SEQUENCE: 195

```
gacatccaaa tgacccagtc accgtcatcg ctctcggctt ccgtgggcga tagagtgacc     60
attacttgca cgagctccca gtccctgttc aacgtgcgca gccagaagaa ctacctcgcc    120
tggtaccagc agaagcctgg aaaagccccg aagcttctga tctactgggc ctcgacccgg    180
gagtctggtg tcccatcccg gttctccgga tccggctccg ggaccgactt cactctgacc    240
attagcagcc tgcagcccga agatttcgcg acctattact gcaagcaatc ctacgacttg    300
ttcacttttg gcgggggaac caaggtcgag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657
```

<210> SEQ ID NO 196
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 196

| | |
|---|---|
| gaggtgcagc tgttggagtc tggggggagg cttggtacagc ctgggggggtc cctgagactc | 60 |
| tcctgtgcag cctctggatt caccttagc agctatgcca tgagctgggt ccgccaggct | 120 |
| ccagggaagg ggctggaatg ggtctcagct attagtggtg gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtat attactgtgc gagggacata | 300 |
| cagtggtacg gggagtcaac cctctttgac tactggggcc agggaaccct ggtcaccgtc | 360 |
| tcctcagcgt cgaccaaggg cccatcggtc ttccccctgg cgccctgctc caggagcacc | 420 |
| tccgagagca cagcggccct gggctgcctg gtcaaggact acttccccga accggtgacg | 480 |
| gtgtcgtgga actcaggcgc tctgaccagc ggcgtgcaca ccttcccggc tgtcctacag | 540 |
| tcctcaggac tctactccct cagcagcgta gtgaccgtgc cctccagcaa cttcggcacc | 600 |
| cagacctaca cctgcaacgt agatcacaag cccagcaaca ccaaggtgga caagacagtt | 660 |
| gagcgcaaat gtgaggtcga gtgcccagag tgcccagcac cacctgtggc aggaccgtca | 720 |
| gtcttcctct tccccccaaa acccaaggac accctcatga tctcccggac ccctgaggtc | 780 |
| acgtgcgtgg tggtggccgt gagccacgaa gaccccgagg tccagttcaa ctggtacgtg | 840 |
| gacggcgtgg aggtgcataa tgccaagaca aagccacggg aggagcagtt caacagcacg | 900 |
| ttccgtgtgg tcagcgtcct caccgtcgtg caccaggact ggctgaacgg caaggagtac | 960 |
| aagtgcaagg tctccaacaa aggcctccca tcctccatcg agaaaaccat ctccaaaacc | 1020 |
| aaagggcagc cccgagaacc acaggtgtac accctgcccc catcccggga ggagatgacc | 1080 |
| aagaaccagg tcagcctgac ctgcgaggtc aaaggcttct accccagcga catcgccgtg | 1140 |
| gagtgggaga gcaatgggca gccggagaac aactacaaga ccacacctcc catgctggac | 1200 |
| tccgacggct ccttcttcct ctacagcaag ctcaccgtgg acaagagcag gtggcagcag | 1260 |
| gggaacgtct tctcatgctc cgtgatgcat gaggctctgc acaaccacta cacacagaag | 1320 |
| agcctctccc tgtcccccgg aaaa | 1344 |

<210> SEQ ID NO 197
<211> LENGTH: 642
<212> TYPE: DNA
<213> ORGANISM: Artificial Sequence
<220> FEATURE:
<223> OTHER INFORMATION: Synthetic Construct

<400> SEQUENCE: 197

| | |
|---|---|
| gacatccaga tgacccagtc tccatcctcc ctgtctgcat ctgtaggaga cagagtcacc | 60 |
| atcacttgcc gggcaagtca gagcacccgt agccacttag cctggtatca gcagaaacca | 120 |
| gggaaagccc ctaagctcct gatctataag gcatccagtt tggaaggtgg ggtcccatca | 180 |
| aggttcagtg gcagtggatc tgggacagat ttcactctca ccatcagcag tctgcaacct | 240 |
| gaagattttg caacttacta ctgtcaacag tatggcagtt attctcggac gttcggccaa | 300 |
| gggaccaagg tggaaatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

```
<210> SEQ ID NO 198
<211> LENGTH: 15
<212> TYPE: PRT
<213> ORGANISM: Artificial Sequence
<220> FEATURE:
<223> OTHER INFORMATION: Synthetic Construct

<400> SEQUENCE: 198

Gly Gly Gly Gly Ser Gly Gly Gly Ser Gly Gly Gly Gly Ser
1               5                   10                  15

<210> SEQ ID NO 199
<211> LENGTH: 5
<212> TYPE: PRT
<213> ORGANISM: Artificial Sequence
<220> FEATURE:
<223> OTHER INFORMATION: Synthetic Construct

<400> SEQUENCE: 199

Gly Tyr Tyr Trp Asn
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic Construct

<400> SEQUENCE: 200

Gly Gly Ser Phe Ser Gly Tyr
1               5

<210> SEQ ID NO 201
<211> LENGTH: 5
<212> TYPE: PRT
<213> ORGANISM: Artificial Sequence
<220> FEATURE:
<223> OTHER INFORMATION: Synthetic Construct

<400> SEQUENCE: 201

Asn His Ser Gly Ser
1               5

<210> SEQ ID NO 202
<211> LENGTH: 5
<212> TYPE: PRT
<213> ORGANISM: Artificial Sequence
<220> FEATURE:
<223> OTHER INFORMATION: Synthetic Construct

<400> SEQUENCE: 202

Asp Tyr Tyr Met Thr
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic Construct

<400> SEQUENCE: 203

Gly Phe Thr Phe Ser Asp Tyr
1               5

<210> SEQ ID NO 204
```

-continued

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 204

Arg Asn Gln Ala Arg Gly Tyr Thr
1               5

<210> SEQ ID NO 205
<211> LENGTH: 5
<212> TYPE: PRT
<213> ORGANISM: Artificial Sequence
<220> FEATURE:
<223> OTHER INFORMATION: Synthetic Construct

<400> SEQUENCE: 205

Ser Tyr Ala Met Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic Construct

<400> SEQUENCE: 206

Gly Phe Thr Phe Ser Ser Tyr
1               5

<210> SEQ ID NO 207
<211> LENGTH: 6
<212> TYPE: PRT
<213> ORGANISM: Artificial Sequence
<220> FEATURE:
<223> OTHER INFORMATION: Synthetic Construct

<400> SEQUENCE: 207

Ser Gly Gly Gly Gly Ser
1               5

<210> SEQ ID NO 208
<211> LENGTH: 326
<212> TYPE: PRT
<213> ORGANISM: Artificial Sequence
<220> FEATURE:
<223> OTHER INFORMATION: Synthetic Construct

<400> SEQUENCE: 208

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
```

```
            100                 105                 110
Pro Val Ala Gly Pro Ser Val Phe Leu Phe Pro Lys Pro Lys Asp
            115                 120                 125

Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 209
<211> LENGTH: 330
<212> TYPE: PRT
<213> ORGANISM: Artificial Sequence
<220> FEATURE:
<223> OTHER INFORMATION: Synthetic Construct

<400> SEQUENCE: 209

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 210
<211> LENGTH: 326
<212> TYPE: PRT
<213> ORGANISM: Artificial Sequence
<220> FEATURE:
<223> OTHER INFORMATION: Synthetic Construct

<400> SEQUENCE: 210

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

-continued

```
                165                 170                 175
Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325
```